(12) United States Patent
Link et al.

(10) Patent No.: US 9,233,974 B2
(45) Date of Patent: Jan. 12, 2016

(54) ANTIVIRAL COMPOUNDS

(71) Applicant: Gilead Sciences, Inc., Foster City, CA (US)

(72) Inventors: John O. Link, San Francisco, CA (US); Jeromy J. Cottell, Redwood City, CA (US); Teresa Alejandra Trejo Martin, Union City, CA (US); Elizabeth M. Bacon, Burlingame, CA (US)

(73) Assignee: Gilead Sciences, Inc., Foster City, CA (US)

( * ) Notice: Subject to any disclaimer, the term of this patent is extended or adjusted under 35 U.S.C. 154(b) by 201 days.

(21) Appl. No.: 13/830,346

(22) Filed: Mar. 14, 2013

(65) Prior Publication Data
US 2014/0178336 A1    Jun. 26, 2014

Related U.S. Application Data

(60) Provisional application No. 61/745,452, filed on Dec. 21, 2012.

(51) Int. Cl.
| | | |
|---|---|---|
| *C07D 491/052* | (2006.01) |
| *A61K 31/352* | (2006.01) |
| *A61K 31/4188* | (2006.01) |
| *A61K 31/7056* | (2006.01) |
| *A61K 31/7068* | (2006.01) |
| *A61K 31/7072* | (2006.01) |
| *A61K 38/21* | (2006.01) |
| *C07D 491/04* | (2006.01) |

(52) U.S. Cl.
CPC .......... *C07D 491/052* (2013.01); *A61K 31/352* (2013.01); *A61K 31/4188* (2013.01); *A61K 31/7056* (2013.01); *A61K 31/7068* (2013.01); *A61K 31/7072* (2013.01); *A61K 38/21* (2013.01); *C07D 491/04* (2013.01)

(58) Field of Classification Search
None
See application file for complete search history.

(56) References Cited

FOREIGN PATENT DOCUMENTS

WO    WO 2012/068234    5/2012

OTHER PUBLICATIONS

International Search Report and Written Opinion from PCT/US2013/076734, mailed Feb. 19, 2014.

*Primary Examiner* — Bong-Sook Baek

(57) ABSTRACT

The disclosure is related to anti-viral compounds, compositions containing such compounds, and therapeutic methods that include the administration of such compounds, as well as to processes and intermediates useful for preparing such compounds.

6 Claims, No Drawings

ANTIVIRAL COMPOUNDS

CROSS REFERENCE TO RELATED APPLICATIONS

This application claims the benefit under 35 U.S.C. §119(e) to U.S. Provisional Application Ser. No. 61/745,452, filed on Dec. 21, 2012, the entirety of which is incorporated herein by reference.

BACKGROUND

Hepatitis C is recognized as a chronic viral disease of the liver which is characterized by liver disease. Although drugs targeting the liver are in wide use and have shown effectiveness, toxicity and other side effects have limited their usefulness. Inhibitors of hepatitis C virus (HCV) are useful to limit the establishment and progression of infection by HCV as well as in diagnostic assays for HCV.

There is a need for new HCV therapeutic agents. In particular, there is a need for HCV therapeutic agents that have broad activity against HCV genotypes (e.g. genotypes 1a, 1b, 2a, 3a, 4a). There is also a particular need for agents that are less susceptible to viral resistance. Resistance mutations to inhibitors have been described for HCV NS5A for genotypes 1a and 1b in Antimicrobial Agents and Chemotherapy, September 2010, Volume 54, p. 3641-3650.

SUMMARY

The present disclosure provides compounds for use in pharmaceutical compositions and methods for treating hepatitis C(HCV). In particular, provided herein are compounds having a polycyclic core and at least one 2,6-dimethyltetrahydro-2H-pyran-4-yl, 4-methyltetrahydro-2H-pyran-4-yl, or tetrahydro-2H-pyran-3-yl capping group, which compounds exhibit beneficial properties, such as, for example, enhanced bioavailability and/or enhanced activity against certain HCV genotypes, including but not limited to, known resistant mutations thereof (see, e.g., Tables 1, 2A and 2B).

In one embodiment the disclosure provides a compound of formula (I):

$$E^{1a}-V^{1a}-C(=O)-P^{1a}-W^{1a}-P^{1b}-C(=O)-V^{1b}-E^{1b}$$ (I)

wherein:

$W^{1a}$ is

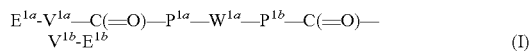

and $W^{1a}$ is optionally substituted with one or more halo, alkyl, haloalkyl, optionally substituted aryl, optionally substituted heterocycle, or cyano;

$Y^5$ is $-O-CH_2-$, $-CH_2-O-$, $-O-C(=O)-$, or $-C(=O)-O-$;

$X^5$ is $-CH_2-CH_2-$, or $-CH=CH-$;

$P^{1a}$ and $P^{1b}$ are each independently:

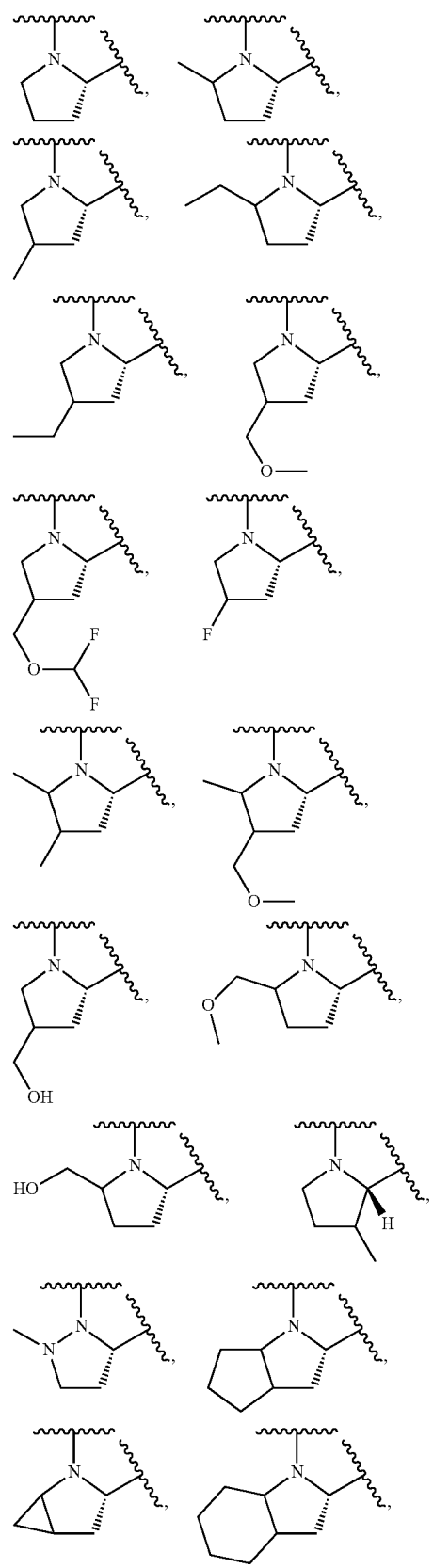

-continued

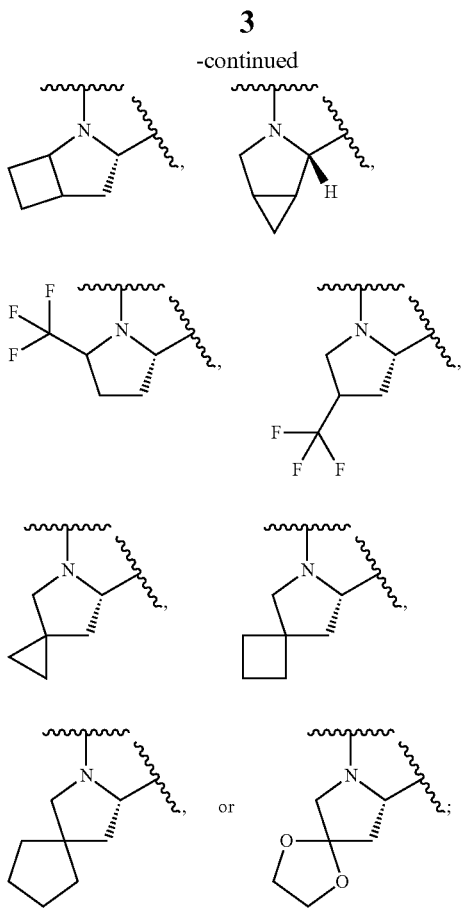

$V^{1a}$ and $V^{1b}$ are each independently:

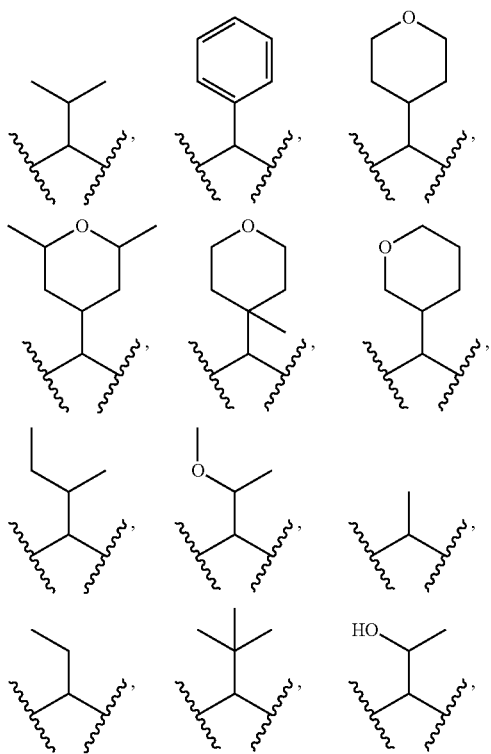

-continued

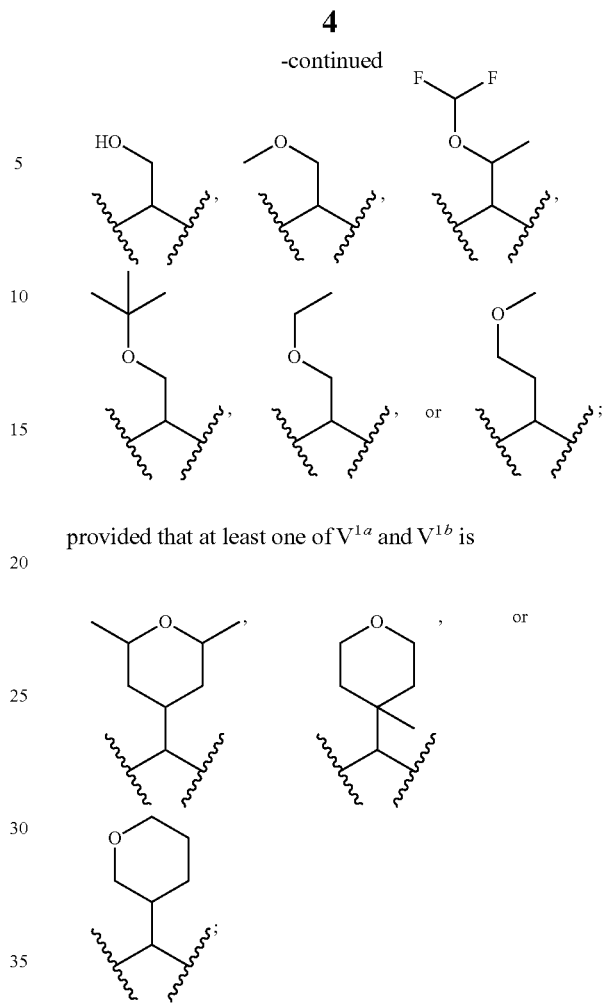

provided that at least one of $V^{1a}$ and $V^{1b}$ is

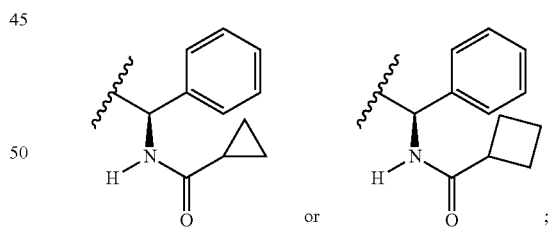

$E^{1a}$ and $E^{1b}$ are each independently —N(H)(alkoxycarbonyl), —N(H)(cycloalkylcarbonyl), or —N(H)(cycloalkyloxycarbonyl); or $E^{1a}$-$V^{1a}$ taken together are $R^{9a}$; or $E^{1b}$-$V^{1b}$ taken together are $R^{9b}$; and $R^{9a}$ and $R^{9b}$ are each independently:

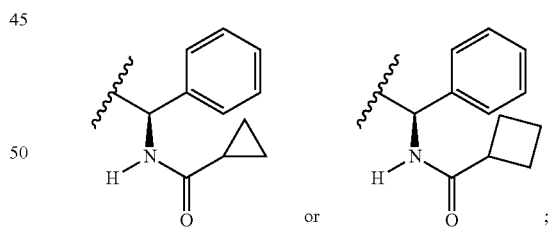

or a pharmaceutically acceptable salt or prodrug thereof.

The disclosure also provides isotopically enriched compounds that are compounds of the disclosure that comprise an enriched isotope at one or more positions in the compound.

The present disclosure also provides a pharmaceutical composition comprising a compound of the disclosure or a pharmaceutically acceptable salt or prodrug thereof and at least one pharmaceutically acceptable carrier.

The present disclosure also provides a pharmaceutical composition for use in treating hepatitis C(HCV). In one embodiment the composition comprises at least one additional therapeutic agent for treating HCV. In one embodiment, the therapeutic agent is selected from ribavirin, an NS3 protease inhibitor, a nucleoside or nucleotide inhibitor of HCV NS5B polymerase, an alpha-glucosidase 1 inhibitor, a hepatoprotectant, a non-nucleoside inhibitor of HCV polymerase, or combinations thereof. In one embodiment, the composition further comprises a nucleoside or nucleotide inhibitor of HCV NS5B polymerase. In one embodiment, the nucleoside or nucleotide inhibitor of HCV NS5B polymerase is selected from ribavirin, viramidine, levovirin, a L-nucleoside, or isatoribine.

In one embodiment, provided is a pharmaceutical composition comprising a compound as described herein and at least one nucleoside or nucleotide inhibitor of HCV NS5B polymerase, and at least one pharmaceutically acceptable carrier. In one embodiment, the composition further comprises an interferon, a pegylated interferon, ribavirin or combinations thereof. In one embodiment, the nucleoside or nucleotide inhibitor of HCV NS5B polymerase is sofosbuvir. In one embodiment, provided is a pharmaceutical composition comprising a compound as described herein and at least one NS3 protease inhibitor, and at least one pharmaceutically acceptable carrier. In one embodiment, the composition further comprises sofosbuvir.

The present disclosure also provides a pharmaceutical composition further comprising an interferon or pegylated interferon.

The present disclosure also provides a pharmaceutical composition further comprising a nucleoside analog.

The present disclosure also provides for a pharmaceutical composition wherein said nucleoside analogue is selected from ribavirin, viramidine, levovirin, an L-nucleoside, and isatoribine and said interferon is α-interferon or pegylated α-interferon.

The present disclosure also provides for a method of treating hepatitis C, said method comprising administering to a human patient a pharmaceutical composition which comprises a therapeutically effective amount of a compound of the disclosure.

The present disclosure also provides a method of inhibiting HCV, comprising administering to a mammal afflicted with a condition associated with HCV activity, an amount of a compound of the disclosure, effective to inhibit HCV.

The present disclosure also provides a compound of the disclosure for use in medical therapy (e.g. for use in inhibiting HCV activity or treating a condition associated with HCV activity), as well as the use of a compound of the disclosure for the manufacture of a medicament useful for inhibiting HCV or the treatment of a condition associated with HCV activity in a mammal.

The present disclosure also provides synthetic processes and novel intermediates disclosed herein which are useful for preparing compounds of the disclosure. Some of the compounds of the disclosure are useful to prepare other compounds of the disclosure.

In another aspect the disclosure provides a compound of the disclosure, or a pharmaceutically acceptable salt or prodrug thereof, for use in the prophylactic or therapeutic treatment of hepatitis C or a hepatitis C associated disorder.

In another aspect the disclosure provides a method of inhibiting HCV activity in a sample comprising treating the sample with a compound of the disclosure.

Compounds of formula (I) have been found to possess useful activity against several HCV genotypes. Additionally certain compounds of formula (I) exhibit significant potency against resistant variants in, e.g., GT1.

DETAILED DESCRIPTION

Reference will now be made in detail to certain embodiments of the disclosure, examples of which are illustrated in the accompanying structures and formulas. While the disclosure will be described in conjunction with the enumerated embodiments, it will be understood that they are not intended to limit the disclosure to those embodiments. On the contrary, the disclosure is intended to cover all alternatives, modifications, and equivalents, which may be included within the scope of the present disclosure as defined by the embodiments.

Compounds

The "P" groups (e.g. $P^{1a}$ and $P^{1b}$) defined for formula (I) herein have one bond to a —C(=O)— of formula (I) and one bond to a $W^{1a}$ group. It is to be understood that a nitrogen of the P group is connected to the —C(=O)— group of formula (I) and that a carbon of the P group is connected to the $W^{1a}$ group.

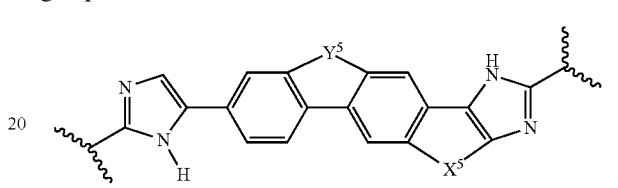

In the $W^{1a}$ group a $Y^5$ group is present. When that $Y^5$ group is defined as —O—$CH_2$—, or —$CH_2$—O— group, those $Y^5$ groups have a directionality. The $Y^5$ group is connected to the $W^{1a}$ group in the same left to right directionality that each is drawn. So for example, when $Y^5$ is —O—$CH_2$—, the directly following structure is intended:

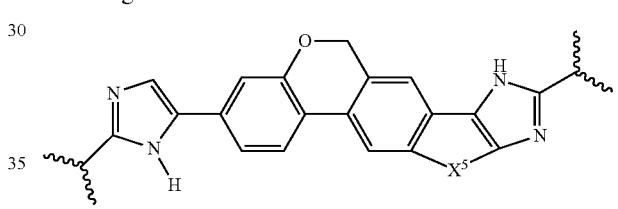

For example, when $Y^5$ is —$CH_2$—O—, the directly following structure is intended:

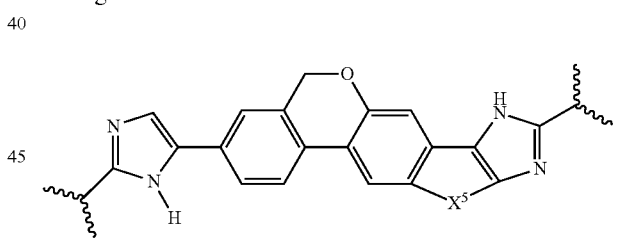

In the structure I, the $W^{1a}$ group has a left-to-right directionality as depicted in I and $W^{1a}$ as they drawn.

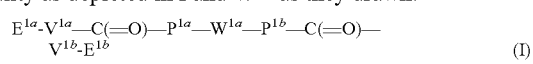

$$E^{1a}-V^{1a}-C(=O)-P^{1a}-W^{1a}-P^{1b}-C(=O)-V^{1b}-E^{1b} \tag{I}$$

wherein:
$W^{1a}$ is

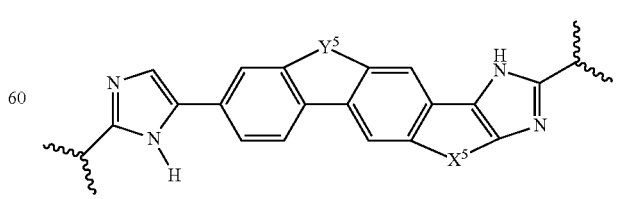

For example, the $P^{1a}$ group is connected to the imidazole group of $W^{1a}$, and the P1b group is connected to the pentacyclic ring system of $W^{1a}$.

"Alkyl" is $C_1$-$C_{18}$ hydrocarbon containing normal, secondary, tertiary or cyclic carbon atoms. Examples are methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, and cyclopropylmethyl

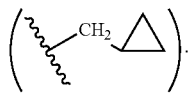

"Alkenyl" is $C_2$-$C_{18}$ hydrocarbon containing normal, secondary, tertiary or cyclic carbon atoms with at least one site of unsaturation, i.e. a carbon-carbon, sp$^2$ double bond. Examples include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to, acetylenic (—C≡CH) and propargyl (—CH$_2$C≡CH).

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to, methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to, 1,2-ethylene (—CH═CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to, acetylene (—C≡C—), propargyl (—CH$_2$C≡C—), and 4-pentynyl (—CH$_2$CH$_2$CH$_2$C≡CH).

The term "alkoxy" or "alkyloxy," as used herein, refers to an alkyl group attached to the parent molecular moiety through an oxygen atom.

The term "alkoxycarbonyl," as used herein, refers to an alkoxy group attached to the parent molecular moiety through a carbonyl group.

The term "cycloalkyl," as used herein, refers to a saturated monocyclic, hydrocarbon ring system having three to seven carbon atoms and zero heteroatoms. Representative examples of cycloalkyl groups include, but are not limited to, cyclopropyl, cyclopentyl, and cyclohexyl. The cycloalkyl groups of the present disclosure are optionally substituted with one, two, three, four, or five substituents independently selected from alkoxy, alkyl, aryl, cyano, halo, haloalkoxy, haloalkyl, heterocyclyl, hydroxy, hydroxyalkyl, nitro, and —NR$^x$R$^y$ wherein the aryl and the heterocyclyl are further optionally substituted with one, two, or three substituents independently selected from alkoxy, alkyl, cyano, halo, haloalkoxy, haloalkyl, hydroxy, and nitro.

The term "cycloalkylcarbonyl," as used herein, refers to a cycloalkyl group attached to the parent molecular moiety through a carbonyl group.

The term "cycloalkyloxy," as used herein, refers to a cycloalkyl group attached to the parent molecular moiety through an oxygen atom.

The term "cycloalkyloxycarbonyl," as used herein, refers to a cycloalkyloxy group attached to the parent molecular moiety through a carbonyl group.

"Aryl" means a monovalent aromatic hydrocarbon radical of 6-20 carbon atoms derived by the removal of one hydrogen atom from a single carbon atom of a parent aromatic ring system. Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group comprises 6 to 20 carbon atoms, e.g., the alkyl moiety, including alkanyl, alkenyl or alkynyl groups, of the arylalkyl group is 1 to 6 carbon atoms and the aryl moiety is 5 to 14 carbon atoms.

"Substituted alkyl", "substituted aryl", and "substituted arylalkyl" mean alkyl, aryl, and arylalkyl respectively, in which one or more hydrogen atoms are each independently replaced with a non-hydrogen substituent. Typical substituents include, but are not limited to: halo (e.g. F, Cl, Br, I), —R, —OR, —SR, —NR$_2$, —CF$_3$, —CCl$_3$, —OCF$_3$, —CN, —NO$_2$, —N(R)C(═O)R, —C(═O)R, —OC(═O)R, —C(O)OR, —C(═O)NRR, —S(═O)R, —S(═O)$_2$OR, —S(═O)$_2$R, —OS(═O)$_2$OR, —S(═O)$_2$NRR, and each R is independently —H, alkyl, aryl, arylalkyl, or heterocycle. Alkylene, alkenylene, and alkynylene groups may also be similarly substituted.

The term "optionally substituted" in reference to a particular moiety of the compound of formula (I), (e.g., an optionally substituted aryl group) refers to a moiety having 0, 1, 2, or more substituents.

The symbol ----- in a ring structure means that a bond is a single or double bond. In a non-limiting example,

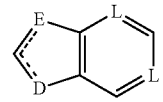

can be

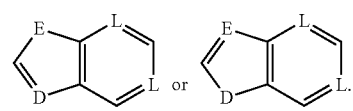

"Haloalkyl" as used herein includes an alkyl group substituted with one or more halogens (e.g. F, Cl, Br, or I). Representative examples of haloalkyl include trifluoromethyl, 2,2, 2-trifluoroethyl, and 2,2,2-trifluoro-1-(trifluoromethyl)ethyl.

"Heterocycle" or "heterocyclyl" as used herein includes by way of example and not limitation these heterocycles described in Paquette, Leo A.; Principles of Modern Heterocyclic Chemistry (W.A. Benjamin, N.Y., 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and J. Am. Chem. Soc. (1960) 82:5566. In one specific embodiment, "heterocycle" includes a "carbocycle" as defined herein, wherein one or more (e.g. 1, 2, 3, or 4) carbon atoms have been replaced with a heteroatom (e.g. O, N, or S). The term heterocycle also includes "heteroaryl" which is a heterocycle wherein at least one heterocyclic rings is aromatic.

Examples of heterocycles include by way of example and not limitation pyridyl, dihydropyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

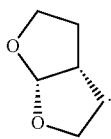

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" refers to a saturated, unsaturated or aromatic ring having up to about 25 carbon atoms. Typically, a carbocycle has about 3 to 7 carbon atoms as a monocycle, about 7 to 12 carbon atoms as a bicycle, and up to about 25 carbon atoms as a polycycle. Monocyclic carbocycles typically have 3 to 6 ring atoms, still more typically 5 or 6 ring atoms. Bicyclic carbocycles typically have 7 to 12 ring atoms, e.g., arranged as a bicyclo[4,5], [5,5], [5,6] or [6,6] system, or 9 or 10 ring atoms arranged as a bicyclo[5,6] or [6,6] system. The term carbocycle includes "cycloalkyl" which is a saturated or unsaturated carbocycle. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl.

The term "amino," as used herein, refers to —NH$_2$.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as, for example, electrophoresis and chromatography.

"Enantiomers" refer to two stereoisomers of a compound which are non-superimposable mirror images of one another.

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes (D and L) or (R and S) are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. The disclosure includes all stereoisomers of the compounds described herein.

Prodrugs

The term "prodrug" as used herein refers to any compound that when administered to a biological system generates a compound of the disclosure that inhibits HCV activity ("the active inhibitory compound"). The compound may be formed from the prodrug as a result of: (i) spontaneous chemical reaction(s), (ii) enzyme catalyzed chemical reaction(s), (iii) photolysis, and/or (iv) metabolic chemical reaction(s).

"Prodrug moiety" refers to a labile functional group which separates from the active inhibitory compound during metabolism, systemically, inside a cell, by hydrolysis, enzymatic cleavage, or by some other process (Bundgaard, Hans, "Design and Application of Prodrugs" in A Textbook of Drug Design and Development (1991), P. Krogsgaard-Larsen and H. Bundgaard, Eds. Harwood Academic Publishers, pp. 113-191). Enzymes which are capable of an enzymatic activation mechanism with the prodrug compounds of the disclosure include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2OC(=O)R^{99}$ and acyloxymethyl carbonates —$CH_2C(=O)OR^{99}$ where $R^{99}$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5,792,756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the disclosure. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC) —$CH_2C(=O)OC(CH_3)_3$.

Protecting Groups

In the context of the present disclosure, protecting groups include prodrug moieties and chemical protecting groups.

"Protecting group" refers to a moiety of a compound that masks or alters the properties of a functional group or the properties of the compound as a whole. Chemical protecting groups and strategies for protection/deprotection are well known in the art. See e.g., Protective Groups in Organic Chemistry, Theodora W. Greene, John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as, for example, the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as, for example, passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g., alcohols, be physiologically acceptable, although in general it is more desirable if the products are pharmacologically innocuous.

Protecting groups are available, commonly known and used, and are optionally used to prevent side reactions with the protected group during synthetic procedures, i.e. routes or methods to prepare the compounds of the disclosure. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as, for example, carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Various functional groups of the compounds of the disclosure may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in Protective Groups in Organic Synthesis, Theodora W. Greene (John Wiley & Sons, Inc., New York, 1991, ISBN 0-471-62301-6) ("Greene"). See also Kocienski, Philip J.; Protecting Groups (Georg Thieme Verlag Stuttgart, N.Y., 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below.

Stereoisomers

The compounds of the disclosure may have chiral centers, e.g., chiral carbon or phosphorus atoms. The compounds of the disclosure thus include all stereoisomers, including enantiomers, diastereomers, and atropisomers. In addition, the compounds of the disclosure include enriched or resolved optical isomers at any or all asymmetric, chiral atoms. In other words, the chiral centers apparent from the depictions are provided as the non-racemic or racemic mixtures. Both racemic and diastereomeric mixtures, as well as the individual optical isomers isolated or synthesized, substantially free of their enantiomeric or diastereomeric partners, are all within the scope of the disclosure. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material or through enantioselective reactions.

The compounds of the disclosure can also exist as tautomeric isomers in certain cases. Although only one tautomer may be depicted, all such forms are contemplated within the scope of the disclosure. For example, ene-amine tautomers can exist for purine, pyrimidine, imidazole, guanidine, amidine, and tetrazole systems and all their possible tautomeric forms are within the scope of the disclosure.

Salts and Hydrates

Examples of physiologically or pharmaceutically acceptable salts of the compounds of the disclosure include salts derived from an appropriate base, such as, for example, an alkali metal (for example, sodium), an alkaline earth metal (for example, magnesium), ammonium and $NX_4^+$ (wherein X is $C_1$-$C_4$ alkyl). Physiologically acceptable salts of a hydrogen atom or an amino group include salts of organic carboxylic acids such as, for example, acetic, benzoic, lactic, fumaric, tartaric, maleic, malonic, malic, isethionic, lactobionic and succinic acids; organic sulfonic acids, such as, for example, methanesulfonic, ethanesulfonic, benzenesulfonic and p-toluenesulfonic acids; and inorganic acids, such as, for example, hydrochloric, sulfuric, phosphoric and sulfamic acids. Physiologically acceptable salts of a compound of a hydroxy group include the anion of said compound in combination with a suitable cation such as, for example, $Na^+$ and $NX_4^+$ (wherein X is independently selected from H or a $C_1$-$C_4$ alkyl group).

For therapeutic use, salts of active ingredients of the compounds of the disclosure will typically be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present disclosure.

Metal salts typically are prepared by reacting the metal hydroxide with a compound of this disclosure. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines, or to acidic groups. Finally, it is to be understood that the compositions herein comprise compounds of the disclosure in their un-ionized, as well as zwitterionic form, and combinations with stoichiometric amounts of water as in hydrates.

Also included within the scope of this disclosure are the salts of the parental compounds with one or more amino acids. Any of the natural or unnatural amino acids are suitable, especially the naturally-occurring amino acids found as protein components, although the amino acid typically is one bearing a side chain with a basic or acidic group, e.g., lysine, arginine or glutamic acid, or a neutral group such as, for example, glycine, serine, threonine, alanine, isoleucine, or leucine.

Methods of Inhibition of HCV

Another aspect of the disclosure relates to methods of inhibiting the activity of HCV comprising the step of treating a sample suspected of containing HCV with a compound or composition of the disclosure.

The treating step of the disclosure comprises adding the compound of the disclosure to the sample or it comprises adding a precursor of the composition to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as, for example, observation of the physiological properties of a living organism are also applicable.

Many organisms contain HCV. The compounds of this disclosure are useful in the treatment or prophylaxis of conditions associated with HCV activation in animals or in man.

However, in screening compounds capable of inhibiting HCV activity it should be kept in mind that the results of enzyme assays may not always correlate with cell culture assays. Thus, a cell based assay should typically be the primary screening tool.

Pharmaceutical Formulations

The compounds of this disclosure are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as, for example, those set forth in the Handbook of Pharmaceutical Excipients (1986). Excipients include ascorbic acid and other antioxidants, chelating agents such as, for example, EDTA, carbohydrates such as, for example, dextrin, hydroxyalkylcellulose, hydroxyalkylmethylcellulose, stearic acid and the like. The pH of the formulations ranges from about 3 to about 11, but is ordinarily about 7 to 10. Typically, the compound will be administered in a dose from 0.01 milligrams to 2 grams. In one embodiment, the dose will be from about 10 milligrams to 450 milligrams. It is contemplated that the compound may be administered once, twice or three times a day.

While it is possible for the active ingredients to be administered alone it may be preferable to present them as pharmaceutical formulations. The formulations, both for veterinary and for human use, of the disclosure comprise at least one active ingredient, as above defined, together with one or more acceptable carriers therefore and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present disclosure suitable for oral administration may be presented as discrete units such as, for example, capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as, for example, a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as, for example, 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as, for example, propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this disclosure may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the disclosure include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as, for example, di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as, for example, white soft paraffin and/or liquid paraffin or other mineral oils are used.

Pharmaceutical formulations according to the present disclosure comprise one or more compounds of the disclosure together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as, for example, calcium or sodium carbonate, lactose, lactose monohydrate, croscarmellose sodium, povidone, calcium or sodium phosphate; granulating and disintegrating agents, such as, for example, maize starch, or alginic acid; binding agents, such as, for example, cellulose, microcrystalline cellulose, starch, gelatin or acacia; and lubricating agents, such as, for example, magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as, for example, glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as, for example, peanut oil, liquid paraffin or olive oil.

Aqueous suspensions of the disclosure contain the active materials in admixture with excipients suitable for the manufacture of aqueous suspensions. Such excipients include a suspending agent, such as, for example, sodium carboxymethylcellulose, methylcellulose, hydroxypropyl methylcellulose, sodium alginate, polyvinylpyrrolidone, gum tragacanth and gum acacia, and dispersing or wetting agents such as, for example, a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as, for example, ethyl or n-propyl p-hydroxy-benzoate, one or more coloring agents, one or more flavoring agents and one or more sweetening agents, such as, for example, sucrose or saccharin.

Oil suspensions may be formulated by suspending the active ingredient in a vegetable oil, such as, for example, arachis oil, olive oil, sesame oil or coconut oil, or in a mineral oil such as, for example, liquid paraffin. The oral suspensions may contain a thickening agent, such as, for example, beeswax, hard paraffin or cetyl alcohol. Sweetening agents, such as, for example, those set forth above, and flavoring agents may be added to provide a palatable oral preparation. These compositions may be preserved by the addition of an antioxidant such as, for example, ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as, for example, olive oil or arachis oil, a mineral oil, such as, for example, liquid paraffin, or a mixture of these. Suitable emulsifying agents include naturally-occurring gums, such as, for example, gum acacia and gum tragacanth, naturally occurring phosphatides, such as, for example, soybean lecithin, esters or partial esters derived from fatty acids and hexitol anhydrides, such as, for example, sorbitan monooleate, and condensation products of these partial esters with ethylene oxide, such as, for example, polyoxyethylene sorbitan monooleate. The emulsion may also contain sweetening and flavoring agents. Syrups and elixirs may be formulated with sweetening agents, such as, for example, glycerol, sorbitol or sucrose. Such formulations may also contain a demulcent, a preservative, a flavoring or a coloring agent.

The pharmaceutical compositions of the disclosure may be in the form of a sterile injectable preparation, such as, for example, a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as, for example, a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as, for example, oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as, for example, gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as, for example, 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as, for example, compounds heretofore used in the treatment or prophylaxis of conditions associated with HCV activity.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this disclosure may include other agents conventional in the art having regard to the type of formulation in question, for example those suitable for oral administration may include flavoring agents.

The disclosure further provides veterinary compositions comprising at least one active ingredient as above defined together with a veterinary carrier therefore.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the disclosure can also be formulated to provide controlled release of the active ingredient to allow less frequent dosing or to improve the pharmacokinetic or toxicity profile of the active ingredient. Accordingly, the disclosure also provides compositions comprising one or more compounds of the disclosure formulated for sustained or controlled release.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of the disclosure (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this disclosure is that they are orally bioavailable and can be dosed orally.

HCV Combination Therapy

In another embodiment, non-limiting examples of suitable combinations include combinations of one or more compounds of formula (I) and (A1-A4) with one or more interferons, ribavirin or its analogs, HCV NS3 protease inhibitors, alpha-glucosidase 1 inhibitors, hepatoprotectants, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs or therapeutic agents for treating HCV.

More specifically, one or more compounds of the present as described herein may be combined with one or more compounds selected from the group consisting of 1) interferons, e.g., pegylated rIFN-alpha 2b (PEG-Intron®), pegylated rIFN-alpha 2a (Pegasys®), rIFN-alpha 2b (Intron® A), rIFN-alpha 2a (Roferon®-A), interferon alpha (MOR-22, OPC-18, Alfaferone®, Alfanative®, Multiferon®, subalin), interferon alfacon-1 (Infergen®), interferon alpha-n1 (Wellferon), interferon alpha-n3 (Alferon®), interferon-beta (Avonex®, DL-8234), interferon-omega (omega DUROS®, Biomed® 510), albinterferon alpha-2b (Albuferon®), IFN alpha-2b XL, BLX-883 (Locteron®), DA-3021, glycosylated interferon alpha-2b (AVI-005), PEG-Infergen, PEGylated interferon lambda-1 (PEGylated IL-29), and Belerofon®;

2) ribavirin and its analogs, e.g., ribavirin (Rebetol®, Copegus®), and taribavirin (Viramidine®);

3) HCV NS3 protease inhibitors, e.g., boceprevir (SCH-503034, SCH-7), telaprevir (VX-950), TMC435350, BI-1335, BI-1230, MK-7009, VBY-376, VX-500, GS-9256, GS-9451, BMS-605339, PHX-1766, AS-101, YH-5258, YH5530, YH5531, ABT-450, ACH-1625, ITMN-191, AT26893, MK5172, MK6325, and MK2748;

4) alpha-glucosidase 1 inhibitors, e.g., celgosivir (MX-3253), Miglitol, and UT-231B;

5) hepatoprotectants, e.g., emericasan (IDN-6556), ME-3738, GS-9450 (LB-84451), silibilin, and MitoQ;

6) nucleoside or nucleotide inhibitors of HCV NS5B polymerase, e.g., R1626, R7128 (R4048), IDX184, IDX-102, BCX-4678, valopicitabine (NM-283), MK-0608, sofosbuvir (GS-7977 (formerly PSI-7977)), VLX-135 (formerly ALS-2200), and INX-189 (now BMS986094);

7) non-nucleoside inhibitors of HCV NS5B polymerase, e.g., PF-868554, VCH-759, VCH-916, JTK-652, MK-3281, GS-9190, VBY-708, VCH-222, A848837, ANA-598, GL60667, GL59728, A-63890, A-48773, A-48547, BC-2329, VCH-796 (nesbuvir), GSK625433, BILN-1941, XTL-2125, ABT-072, ABT-333, GS-9669, PSI-7792, and GS-9190;

8) HCV NS5A inhibitors, e.g., AZD-2836 (A-831), BMS-790052, ACH-3102, ACH-2928, MK8325, MK4882, MK8742, PSI-461, IDX719, GS-5885, and A-689;

9) TLR-7 agonists, e.g., imiquimod, 852A, GS-9524, ANA-773, ANA-975 (isatoribine), AZD-8848 (DSP-3025), and SM-360320;

10) cyclophillin inhibitors, e.g., DEBIO-025, SCY-635, and NIM811;

11) HCV IRES inhibitors, e.g., MCI-067;

12) pharmacokinetic enhancers, e.g., BAS-100, SPI-452, PF-4194477, TMC-41629, GS-9350 (cobicistat), GS-9585, and roxythromycin; and 13) other drugs for treating HCV, e.g., thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, BMS-791325, Bavituximab, MDX-1106 (ONO-4538), Oglufanide, and VX-497 (merimepodib).

In yet another embodiment, the present application discloses pharmaceutical compositions comprising a compound as described herein, or a pharmaceutically acceptable salt, solvate, and/or ester thereof, in combination with at least one additional therapeutic agent, and a pharmaceutically acceptable carrier or excipient.

In another embodiment is provided a pharmaceutical composition comprising a compound of formula (I) as described herein and sofosbuvir and/or GS-5885 and optionally an interferon or ribavirin.

It is contemplated that additional therapeutic agents will be administered in a manner that is known in the art and the dosage may be selected by someone of skill in the art. For example, additional therapeutic agents may be administered in a dose from about 0.01 milligrams to about 2 grams per day.

Metabolites of the Compounds

Also falling within the scope of this disclosure are the in vivo metabolic products of the compounds described herein. Such products may result for example from the oxidation, reduction, hydrolysis, amidation, esterification and the like of the administered compound, primarily due to enzymatic processes. Accordingly, the disclosure includes compounds produced by a process comprising contacting a compound of this disclosure with a mammal for a period of time sufficient to yield a metabolic product thereof. Such products typically are identified by preparing a radiolabelled (e.g., $C^{14}$ or $H^3$) compound of the disclosure, administering it parenterally in a detectable dose (e.g., greater than about 0.5 mg/kg) to an animal such as, for example, rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the disclosure even if they possess no HCV— inhibitory activity of their own.

Methods for determining stability of compounds in surrogate gastrointestinal secretions are known.

Exemplary Methods of Making the Compounds

The disclosure also relates to methods of making the compositions of the disclosure. The compositions are prepared by any of the applicable techniques of organic synthesis. Many such techniques are well known in the art. However, many of the known techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., Advanced Organic Chemistry, Third Edition, (John Wiley & Sons, New York, 1985), Comprehensive Organic Synthesis. Selectivity, Strategy & Efficiency in Modern Organic Chemistry. In 9 Volumes, Barry M. Trost, Editor-in-Chief (Pergamon Press, New York, 1993 printing). Other methods suitable for preparing compounds of the disclosure are described in International Patent Application Publication Number WO 2006/020276.

A number of exemplary methods for the preparation of the compositions of the disclosure are provided in the schemes and examples below. These methods are intended to illustrate the nature of such preparations and are not intended to limit the scope of applicable methods.

Generally, the reaction conditions such as, for example, temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Work-up typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as, for example, azeotropic removal of reaction by-products and use of anhydrous reaction conditions (e.g., inert gas environments) are common in the art and will be applied when applicable.

The terms "treated", "treating", "treatment", and the like, when used in connection with a chemical synthetic operation, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two. For example, treating indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic synthesis selects conditions and apparatus reasonably expected to successfully carry out the chemical reactions of the described processes based on the knowledge in the art.

Modifications of each of the exemplary schemes and in the Examples (hereafter "exemplary schemes") leads to various analogs of the specific exemplary materials produce. The above-cited citations describing suitable methods of organic synthesis are applicable to such modifications.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as, for example, activated carbon, molecular sieves, ion exchange media, or the like. Alternatively, the reagents can be acids in the case of a basic material, bases in the case of an acidic material, binding reagents such as, for example, antibodies, binding proteins, selective chelators such as, for example, crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as, for example, formation of diastereomers using optically active resolving agents (Stereochemistry of Carbon Compounds, (1962) by E. L. Eliel, McGraw Hill; Lochmuller, C. H., (1975) *J. Chromatogr.*, 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as, for example, brucine, quinine, ephedrine, strychnine, α-methyl-β-phenylethylamine (amphetamine), and the like with asymmetric compounds bearing acidic functionality, such as, for example, carboxylic acid and sulfonic acid. The diastereomeric salts may be induced to separate by fractional crystallization or ionic chromatography. For separation of the optical isomers of amino compounds, addition of chiral carboxylic or sulfonic acids, such as, for example, camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as, for example, menthyl derivatives, followed by separation of the diastereomers and hydrolysis to yield the free, enantiomerically enriched substrate. A method of determining optical purity involves making chiral esters, such as, for example, a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as, for example, optical rotation and circular dichroism.

Schemes and Examples

General aspects of these exemplary methods are described below and in the Examples. Each of the products of the following processes is optionally separated, isolated, and/or purified prior to its use in subsequent processes.

A number of exemplary methods for the preparation of compounds of the disclosure are provided herein, for example, in the Examples below. These methods are intended to illustrate the nature of such preparations and are not intended to limit the scope of applicable methods. Certain compounds of the disclosure can be used as intermediates for the preparation of other compounds of the disclosure. In the exemplary methods described herein, the fragment E-V- can also be written as R9-. PG represents a protecting group common for the given functional group that it is attached. The installation and removal of the protecting group can be accomplished using standard techniques, such as those described in Wuts, P. G. M., Greene, T. *Protective Groups in Organic Synthesis*, 4th ed.; John Wiley & Sons, Inc.: Hoboken, N.J., 2007.

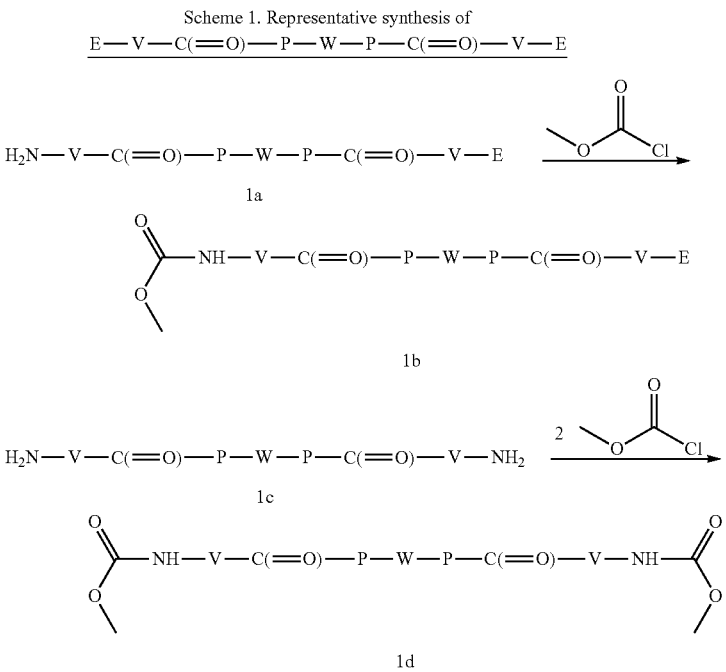

Scheme 1 shows a general synthesis of an E-V—C(=O)—P—W—P—C(=O)—V-E molecule of the disclosure wherein, for illustrative purposes, E is methoxycarbonylamino. The treatment of either 1a or 1c with one or two equivalents respectively of methyl chloroformate under basic conditions (e.g. sodium hydroxide) provides the molecule 1b or 1d.

with two equivalents of 2b' directly to provide 2e where E' is a leaving group such as hydroxybenztriazole, para-nitrophenol or the like making the structure 2b' an activated ester.

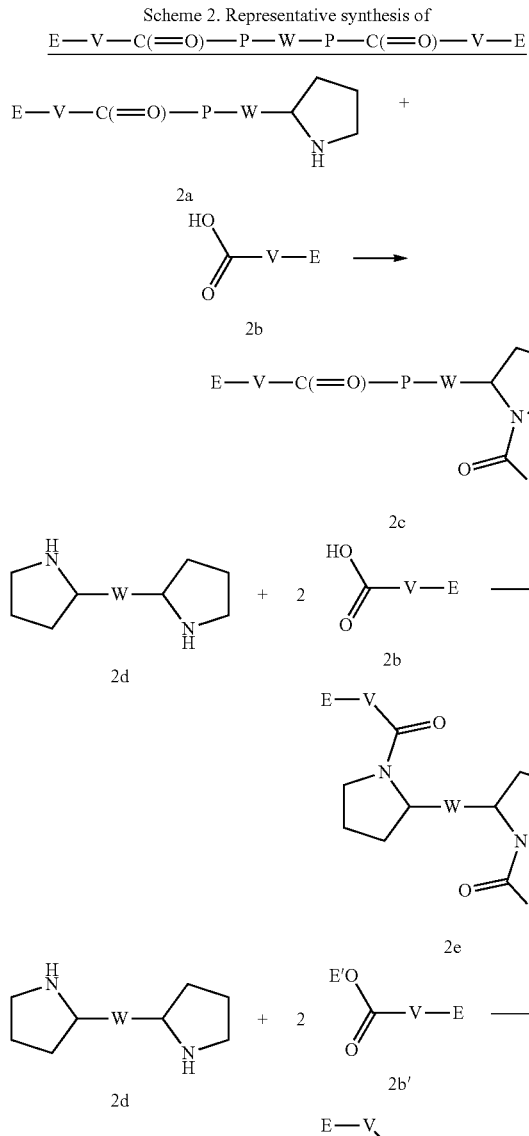

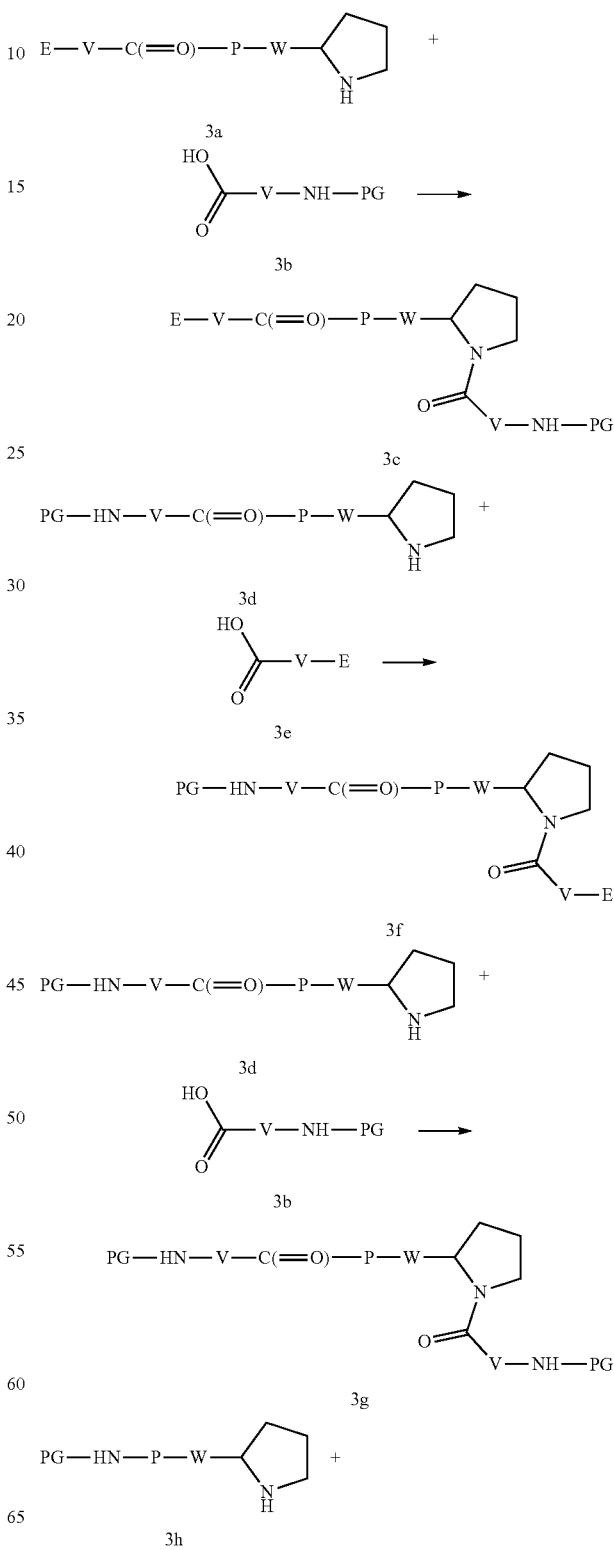

Scheme 2 shows a general synthesis of an E—V—C(=O)—P—W—P—C(=O)—V-E molecule of the disclosure wherein, for illustrative purposes, P is pyrrolidine. Coupling of amine 2a with acid 2b is accomplished using a peptide coupling reagent (e.g. HATU) to afford 2c. Alternatively, amine 2d is coupled with two equivalents of 2b under similar conditions to provide 2e. Alternatively, amine 2d is reacted

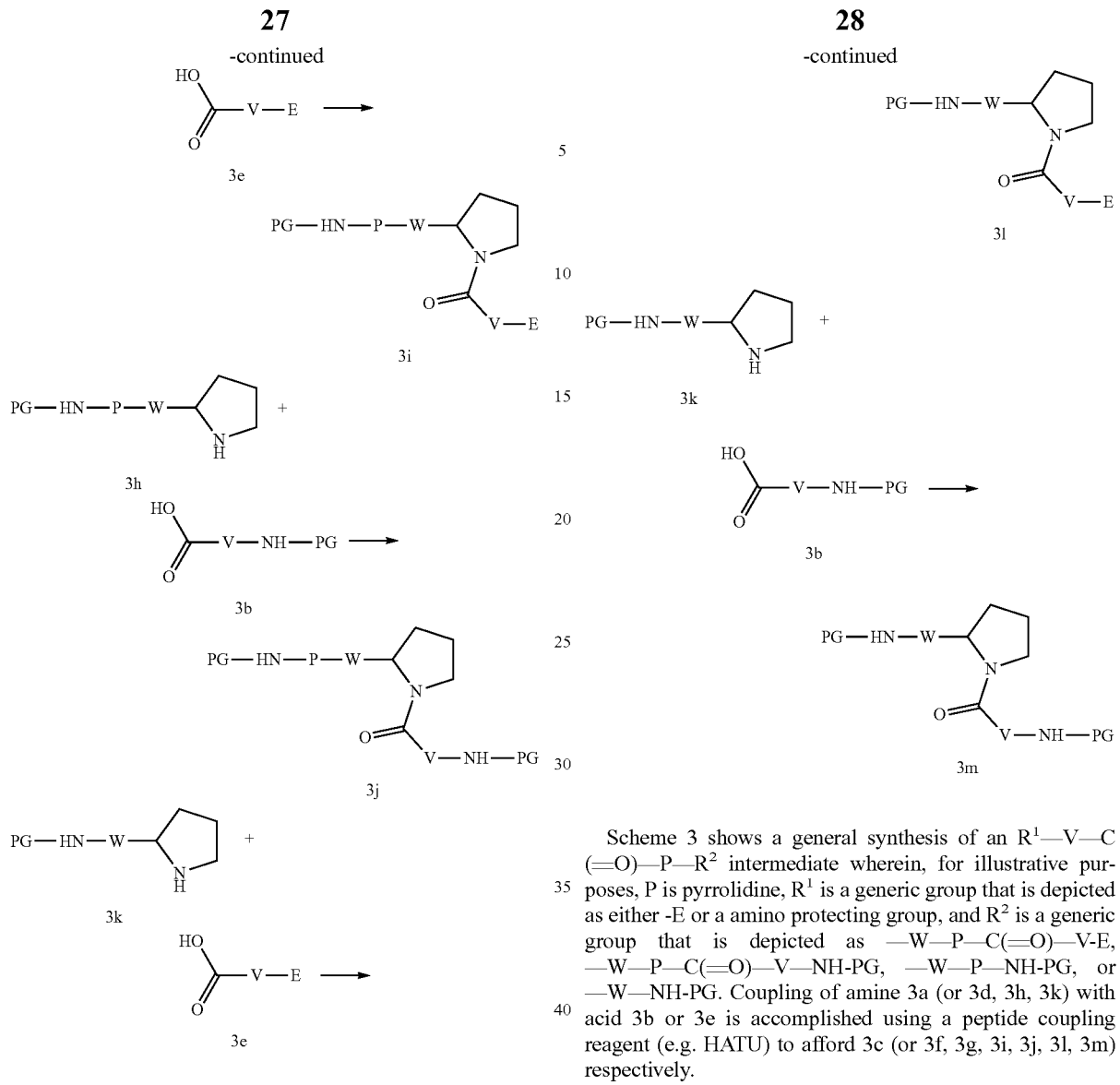

Scheme 3 shows a general synthesis of an $R^1$—V—C(=O)—P—$R^2$ intermediate wherein, for illustrative purposes, P is pyrrolidine, $R^1$ is a generic group that is depicted as either -E or a amino protecting group, and $R^2$ is a generic group that is depicted as —W—P—C(=O)—V-E, —W—P—C(=O)—V—NH-PG, —W—P—NH-PG, or —W—NH-PG. Coupling of amine 3a (or 3d, 3h, 3k) with acid 3b or 3e is accomplished using a peptide coupling reagent (e.g. HATU) to afford 3c (or 3f, 3g, 3i, 3j, 3l, 3m) respectively.

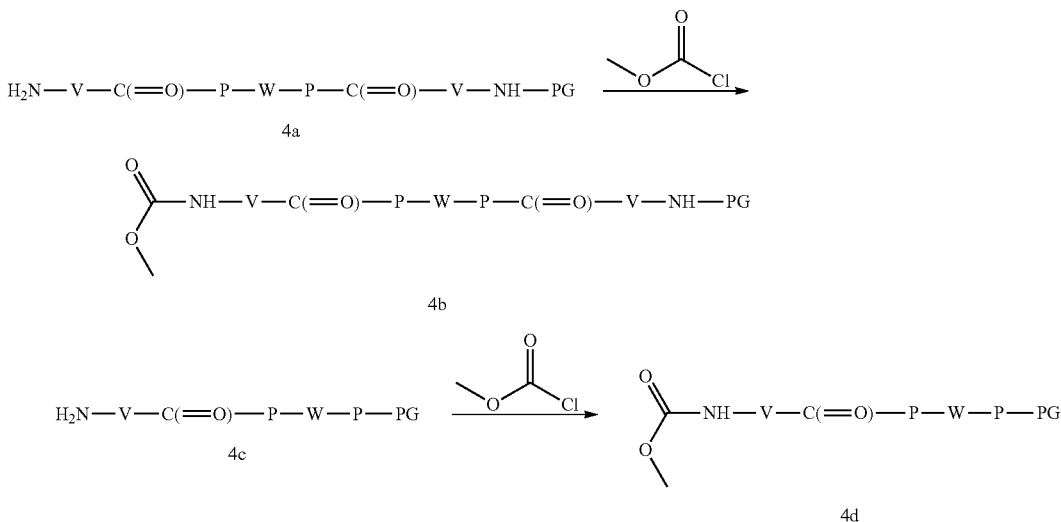

Scheme 4. Representative synethesis of E—V—C(=O)—$R^1$

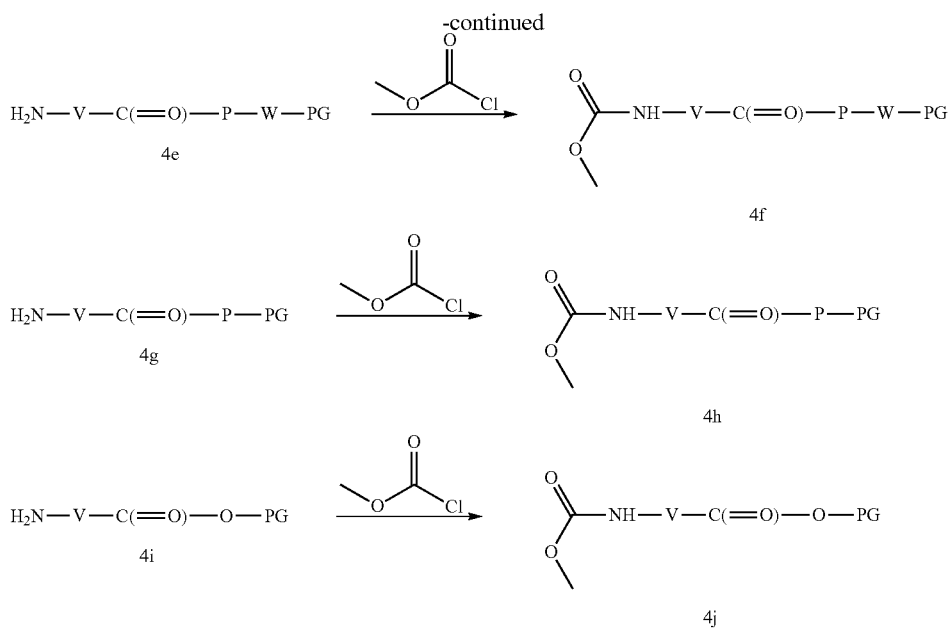
Scheme 4 shows a general synthesis of an E-V—C(=O)—R' intermediate wherein, for illustrative purposes, E is methoxycarbonylamino and $R^1$ is a generic group that is depicted as either —P—W—P—C(=O)—V—NH-PG, —P—W—P-PG, —P—W-PG, —P-PG, or —O-PG. Treatment of 4a (or 4c, 4e, 4g, 4i) with methyl chloroformate under basic conditions (e.g. sodium hydroxide) provides the molecule 4b (or 4d, 4f, 4h, 4j).
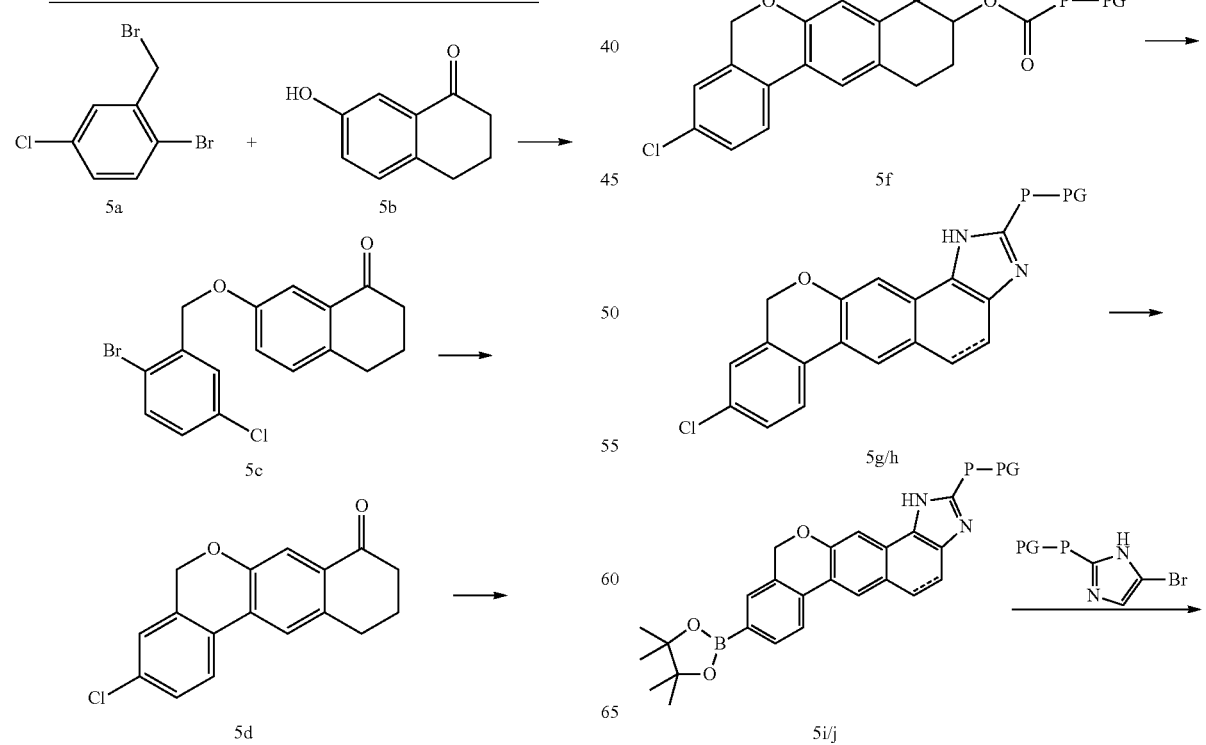

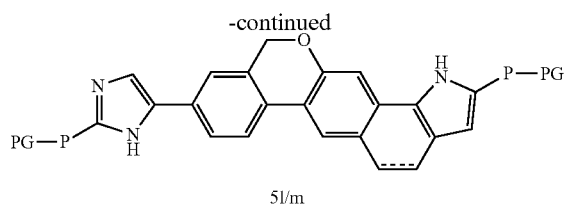

5l/m

Scheme 5 shows a general synthesis of an R¹—P—W—P—R² intermediate of the disclosure wherein, for illustrative purposes, R¹ and R² are independent protecting groups and W is a two aromatic ring unit constructed via a transition metal mediated cyclization. Alkylation of phenol 5b with an alkyl bromide, such as 5a, provides the ether 5c. Cyclization of the aromatic rings in the presence of a palladium catalyst provides the compound 5d. Treatment of 5d with CuBr$_2$ provides the α-haloketone 5e, which provides 5f upon addition of an acid under basic conditions (e.g. Et$_3$N). Reaction of 5f with an amine or amine salt (e.g. ammonium acetate) affords the imidazole containing molecule 5g. Oxidation of 5g, 5i, or 5l can be accomplished by heating in the presence of MnO$_2$ to provide 5h, 5j, or 5m, respectively. Conversion of 5g or 5h with a palladium catalyst, such as Pd$_2$dba$_3$ and X-Phos, and a boron source such as bis(pinacolato)diboron provides the boronic ester 5i or 5j. The boronic ester is coupled with an appropriate coupling partner (e.g. 5k) using a palladium catalyst, such as Pd(PPh$_3$)$_4$ or PdCl$_2$(dppf), to afford 5l or 5m. For each transition metal mediated cross-coupling reaction, the roles of the nucleophile and electrophile can be reversed to provide the same coupling product. Other transition metal mediated cross couplings that enable the construction of W, but employ alternative coupling partners and reagents, include, but are not limited to, the Negishi, Kumada, Stille, and Ullman couplings. For the preparation of alternate two aromatic ring containing W groups, this general scheme can be applied through the appropriate choice of the starting reagents.

Scheme 6. Representative synthesis of R¹—P—W—P—R²

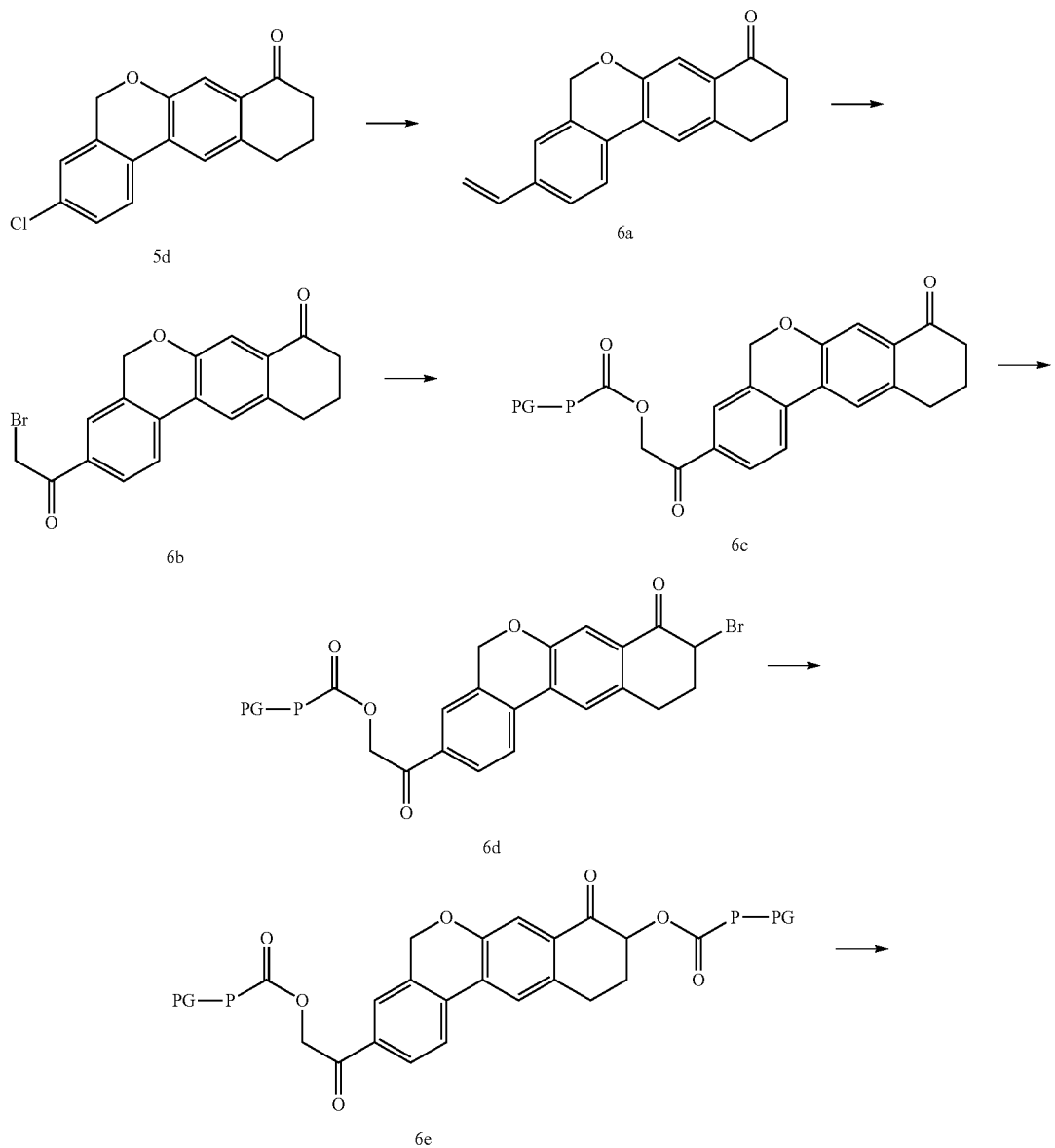

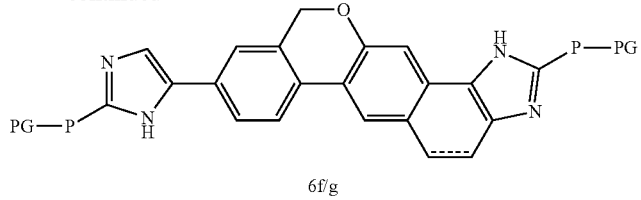

6f/g

Scheme 6 shows a general synthesis of an R¹—P—W—P—R² intermediate of the disclosure wherein, for illustrative purposes, R¹ and R² are independent protecting groups and W is a two aromatic ring unit constructed via a transition metal mediated cyclization. Treatment of 5d with an activated vinyl reagent (e.g. potassium vinyltrifluoroborate) in the presence of a palladium catalyst (e.g. palladium acetate and S-Phos) provides the vinyl compound 6a. Conversion to the corresponding α-halo ketone can be accomplished by bromination with N-bromosuccinimide, followed by oxidation with $MnO_2$. Displacement of the α-halo ketone proceeds by the addition of an acid under basic conditions (e.g. $Et_3N$). Bromination of 6d proceeds upon treatment with pyridinium tribromide, and is followed by the addition of a second acid under basic conditions to provide the diester 6e. Reaction of 6e with an amine or amine salt (e.g. ammonium acetate) affords the imidazole containing molecule 6f. Oxidation of 6f can be accomplished in the presence of $MnO_2$ to provide 6g.

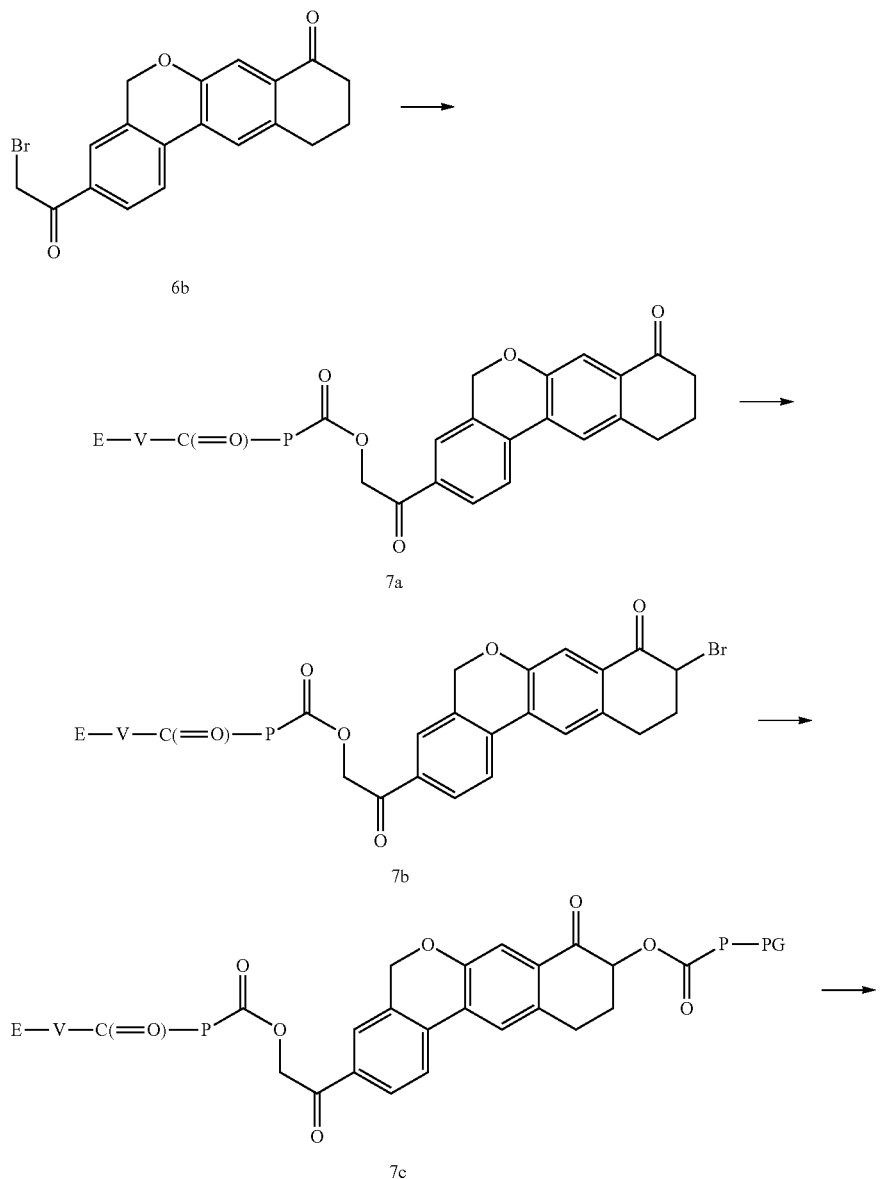

Scheme 7. Representative synthesis of E—V—C(=O)—P—W—P—R

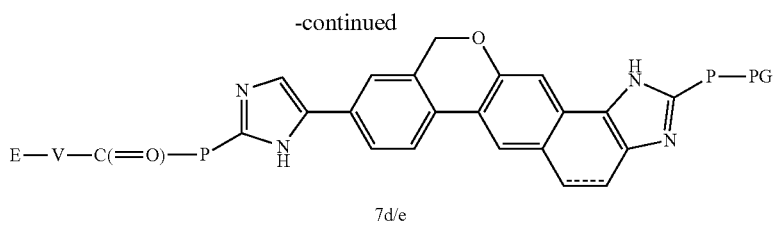

7d/e

Scheme 7 shows a general synthesis of an E-V—C(=O)—P—W—P—R intermediate of the disclosure wherein, for illustrative purposes, R is a protecting group and W is a two aromatic ring unit. Displacement of the α-halo ketone 6b proceeds by the addition of an acid under basic conditions (e.g. Et₃N). Bromination of 7b proceeds upon treatment with pyridinium tribromide, and is followed by the addition of a second acid under basic conditions to provide the diester 7c. Reaction of 7c with an amine or amine salt (e.g. ammonium acetate) affords the imidazole containing molecule 7d. Oxidation of 7d can be accomplished in the presence of MnO₂ to provide 7e.

Scheme 8 shows a general synthesis of an E-V—C(=O)—P—W—P—R intermediate of the disclosure wherein, for illustrative purposes, R is a protecting group and W is a two aromatic ring unit. Displacement of the α-halo ketone 6d proceeds by the addition of an acid under basic conditions (e.g. Et₃N). Reaction of 8a with an amine or amine salt (e.g. ammonium acetate) affords the imidazole containing molecule 8b. Oxidation of 8b can be accomplished in the presence of MnO₂ to provide 8c.

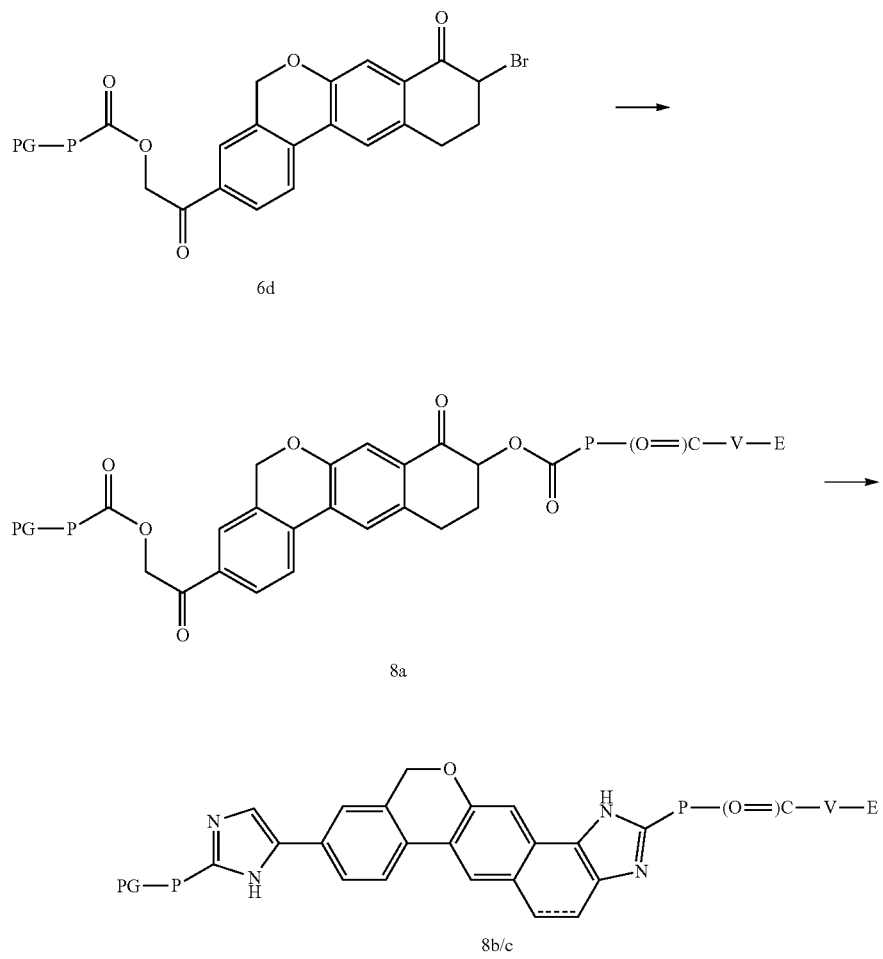

Scheme 8. Representative synthesis of R—P—W—P—C(=O)—V—E

Scheme 9. Representative synthesis of
E—V—C(=O)—P—W—P—C(=O)—V—E

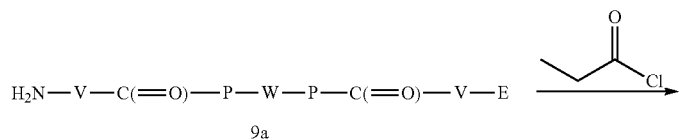

9a

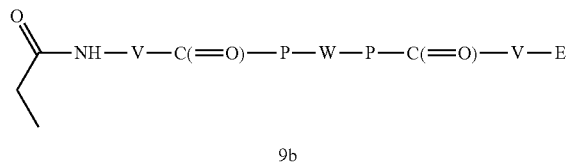

9b

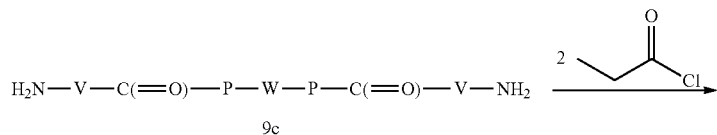

9c

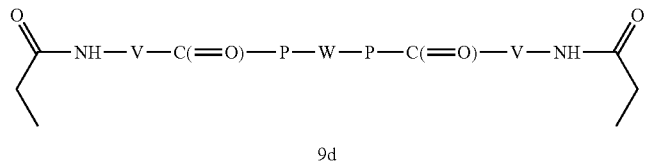

9d

Scheme 9 shows a general synthesis of an E-V—C(=O)—P—W—P—C(=O)—V-E molecule of the disclosure wherein, for illustrative purposes, E is ethylcarbonylamino. The treatment of either 9a or 9c with one or two equivalents respectively of propionyl chloride under basic conditions (e.g. sodium hydroxide) provides the molecule 9b or 9d.

Scheme 10. Representative synthesis of
$R^1$—P—W—P—$R^2$

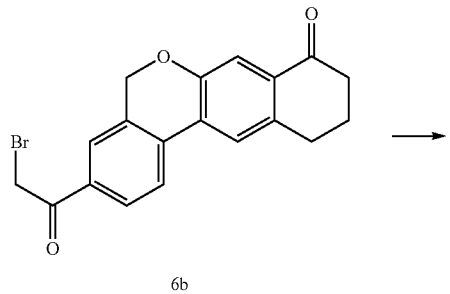

6b

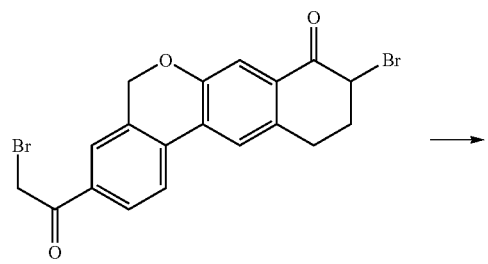

10a

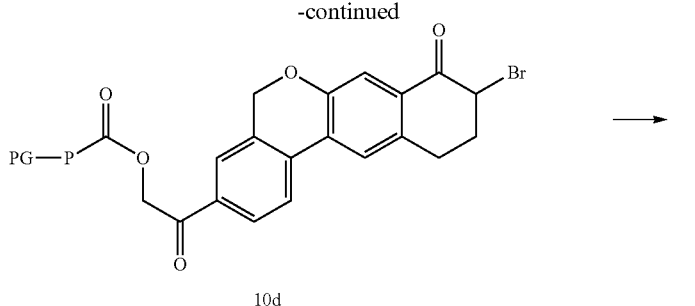

10d

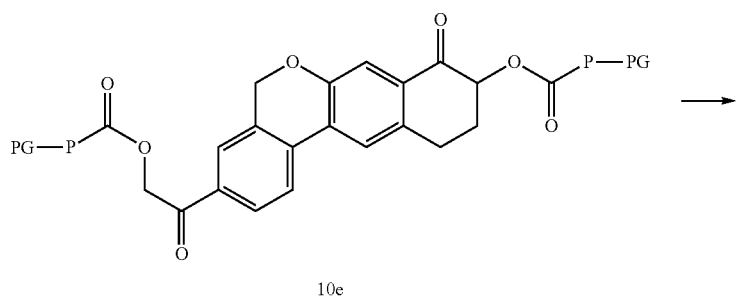

10e

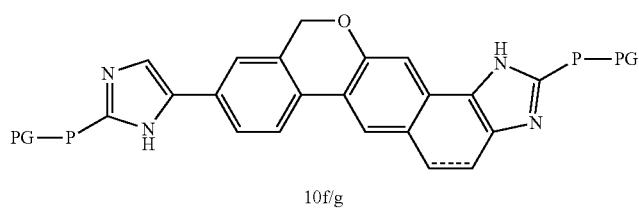

10f/g

Scheme 10 shows an alternate general synthesis of an R$^1$—P—W—P—R$^2$ intermediate of the invention wherein, for illustrative purposes, R$^1$ and R$^2$ are independent protecting groups and W is a two aromatic ring unit constructed via a transition metal mediated cyclization. Bromination of 6b with a brominating agent (i.e. pyridinium tribromide) provides the dibromide 10a. Displacement of the primary bromide then proceeds by the addition of an acid under basic conditions (e.g. K$_2$CO$_3$) to provide 10d. Conversion to 10f or 10g can be accomplished following methods described in Scheme 8.

Scheme 11. Representative synthesis of E—V—C(=O)—P—W—P—R

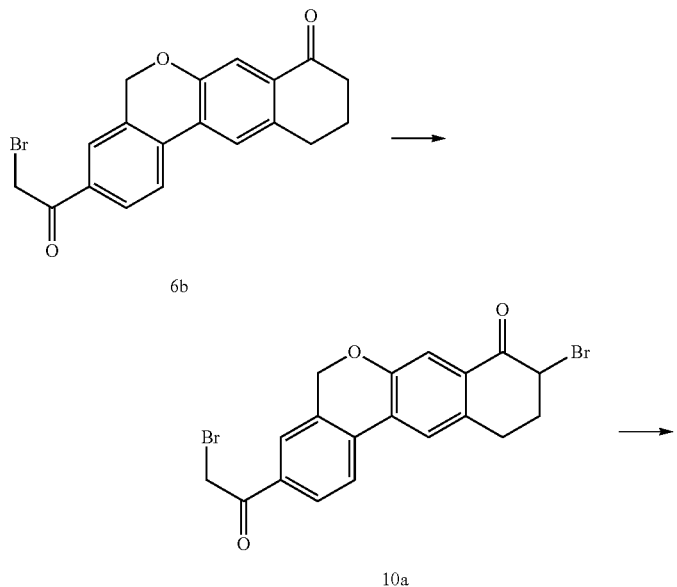

6b

10a

-continued

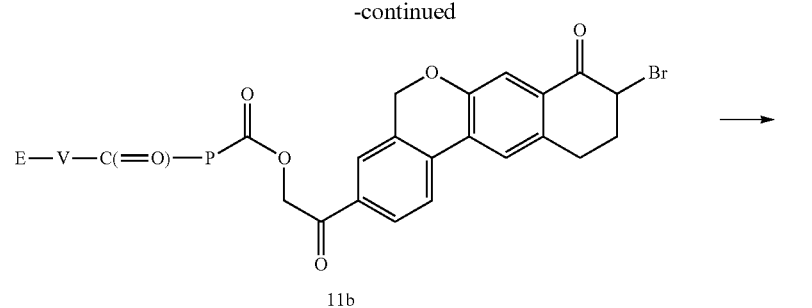

11b

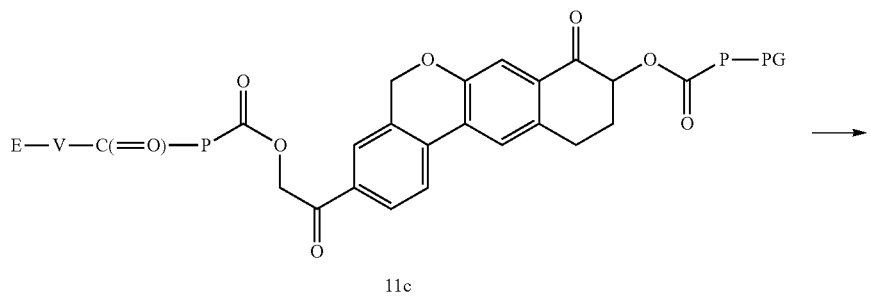

11c

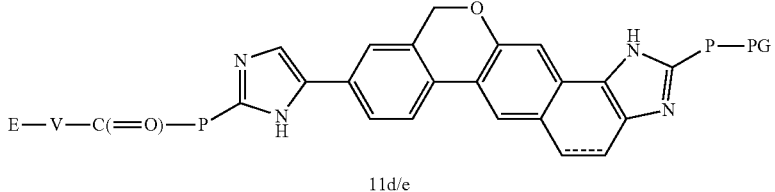

11d/e

Scheme 11 shows an alternate general synthesis of an E-V—C(=O)—P—W—P—R intermediate of the invention wherein, for illustrative purposes, R is a protecting group and W is a two aromatic ring unit. Bromination of 6b with a brominating agent (i.e. pyridinium tribromide) provides the dibromide 10a. Displacement of the primary bromide then proceeds by the addition of an acid under basic conditions (e.g. K₂CO₃) to provide 11b. Conversion to 11d or 11e can be accomplished following methods described in Scheme 8.

Scheme 12. Representative synthesis of
R¹—V—C(=O)—P—R²

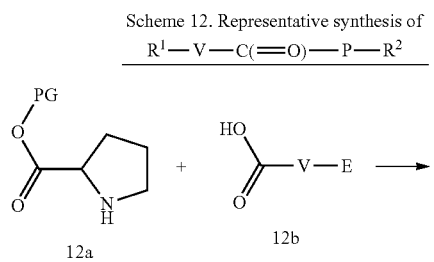

12a + 12b

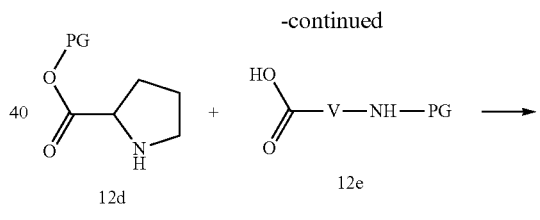

12d + 12e

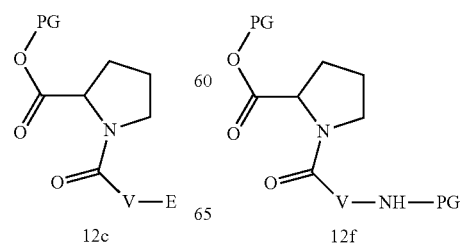

12c    12f

-continued

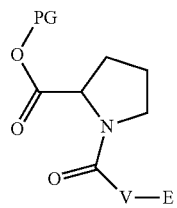

12c

Scheme 12 shows a general synthesis of an $R^1$—V—C(=O)—P—$R^2$ intermediate wherein, for illustrative purposes, P is pyrrolidine, $R^1$ is a generic group that is depicted as either -E or a amino protecting group, and $R^2$ is a generic group that is depicted as —C(=O)—O-PG. Coupling of amine 12a (or 12d) with acid 12b or 12e is accomplished using a peptide coupling reagent (e.g. HATU) to afford 12c (or 12f) respectively. The conversion of 12f to 12c can be accomplished by removal of the appropriate protecting group, followed by treatment with methyl chloroformate under basic conditions (e.g. sodium hydroxide).

$K_2CO_3$) to provide 11c. Conversion to 11d or 11e can be accomplished following methods described in Scheme 8.

Specific Embodiments

In one embodiment, provided is a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b} \quad (I)$$

wherein:
$W^{1a}$ is

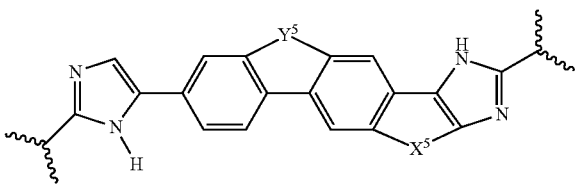

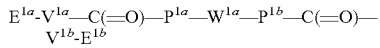

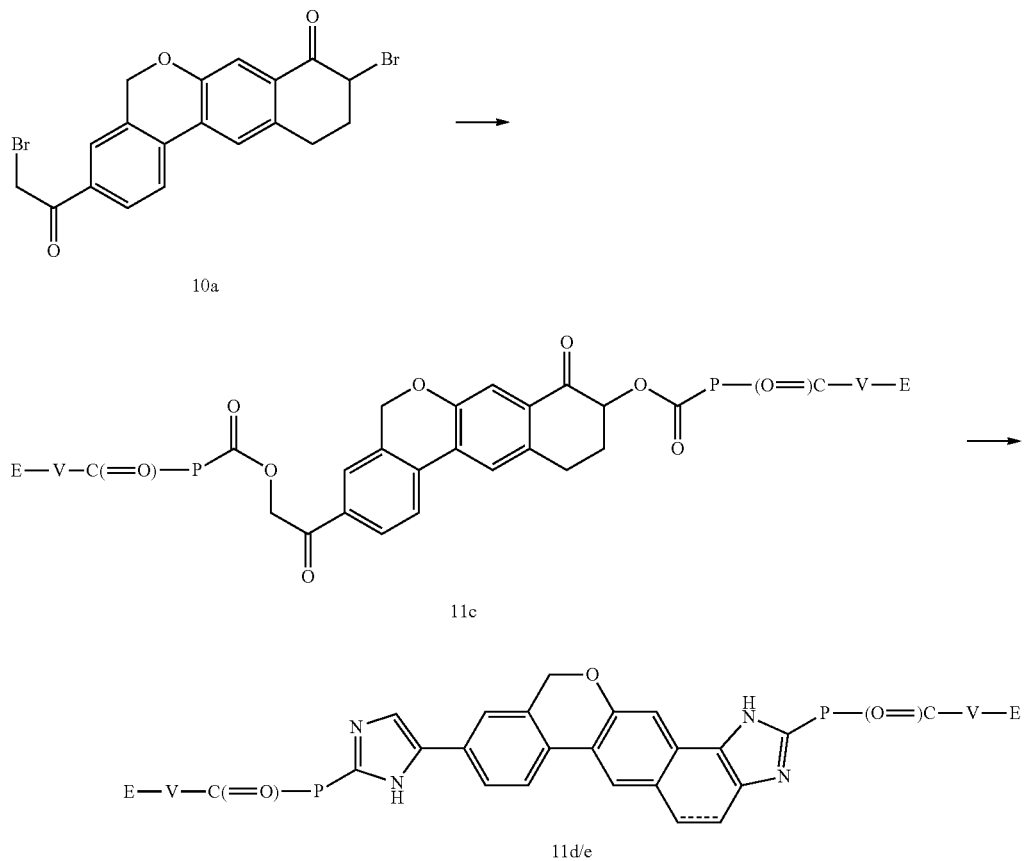

Scheme 13 shows an alternate general synthesis of an E-V—C(=O)—P—W—P—C(=O)—V-E intermediate of the invention wherein, for illustrative purposes, W is a two aromatic ring unit. Displacement of the both bromides proceeds by the addition of an acid under basic conditions (e.g.

and $W^{1a}$ is optionally substituted with one or more halo, alkyl, haloalkyl, optionally substituted aryl, optionally substituted heterocycle, or cyano;
$Y^5$ is -O—$CH_2$—, —$CH_2$—O—, —O—C(=O)—, or —C(=O)—O—;
$X^5$ is —$CH_2$—$CH_2$—, or —CH=CH—;

$P^{1a}$ and $P^{1b}$ are each independently:
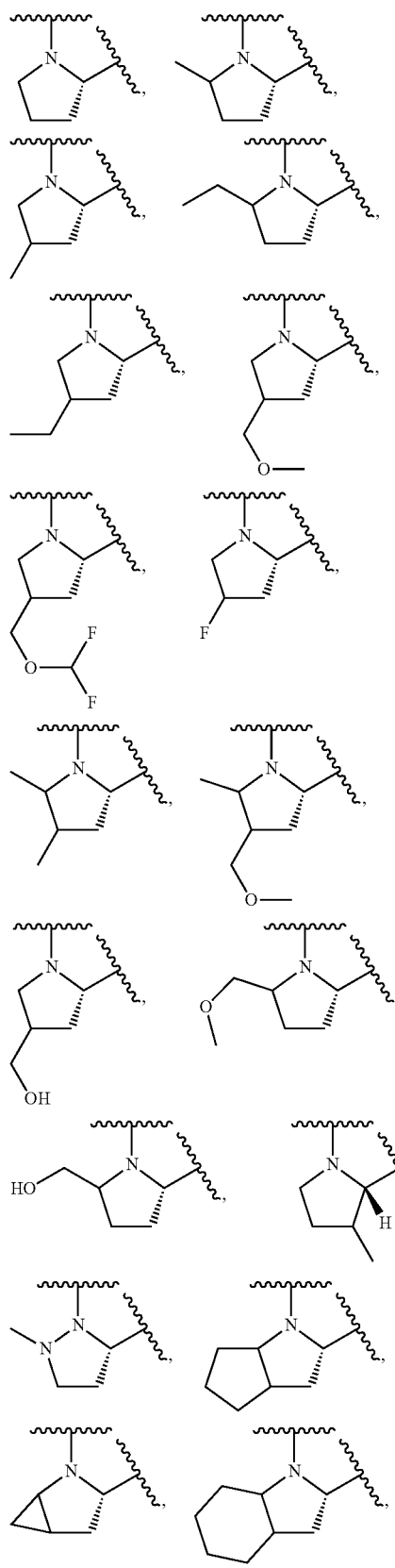
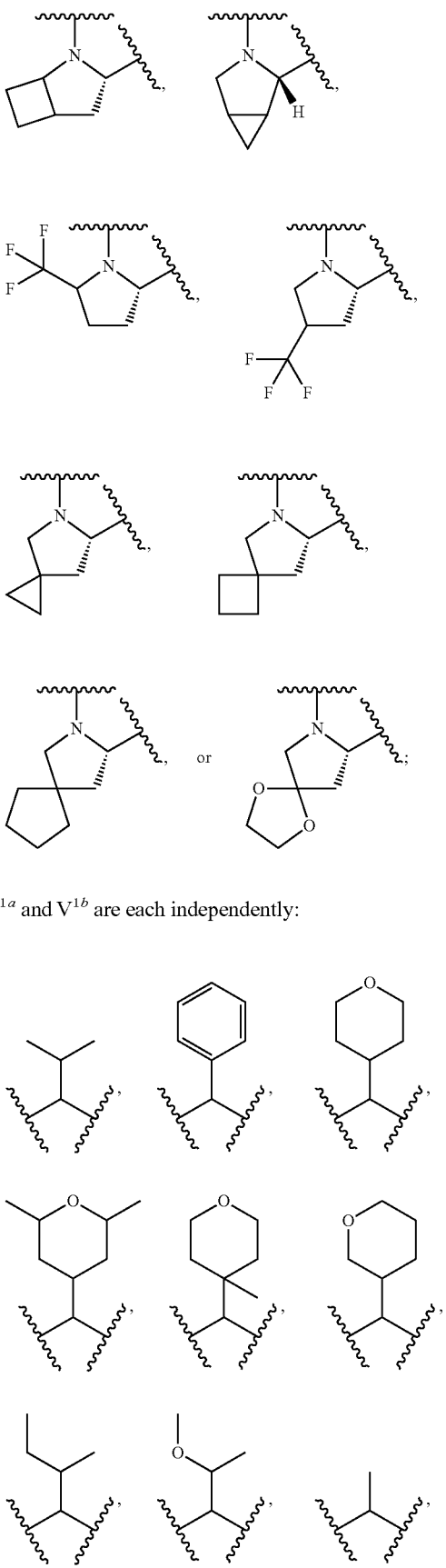
$V^{1a}$ and $V^{1b}$ are each independently:

-continued

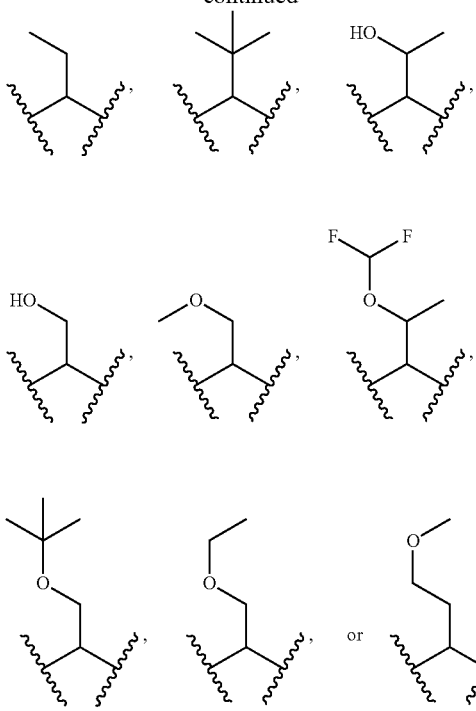

provided that at least one of $V^{1a}$ and $V^{1b}$ is

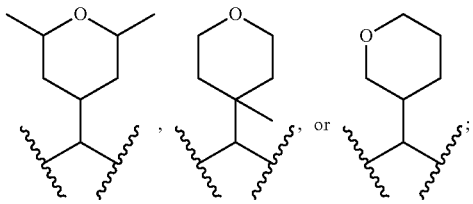

$E^{1a}$ and $E^{1b}$ are each independently —N(H)(alkoxycarbonyl), —N(H)(cycloalkylcarbonyl), or —N(H)(cycloalkyloxycarbonyl); or $E^{1a}$-$V^{1a}$ taken together are $R^{9a}$; or $E^{1b}$-$V^{1b}$ taken together are $R^{9b}$; and $R^{9a}$ and $R^{9b}$ are each independently:

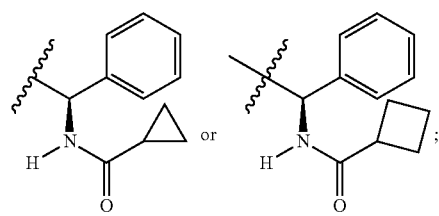 [SMILES: *[C@H](NC(=O)C1CC1)c1ccccc1 ; *[C@H](NC(=O)C1CCC1)c1ccccc1]

or a pharmaceutically acceptable salt or prodrug thereof.

In one embodiment the disclosure provides a compound which has formula:

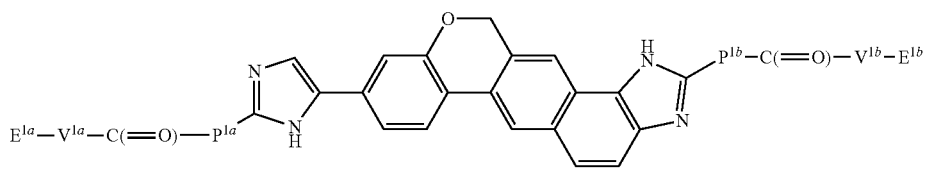

(A1)

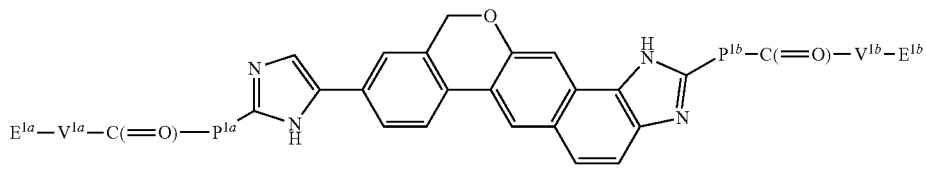

(A2)

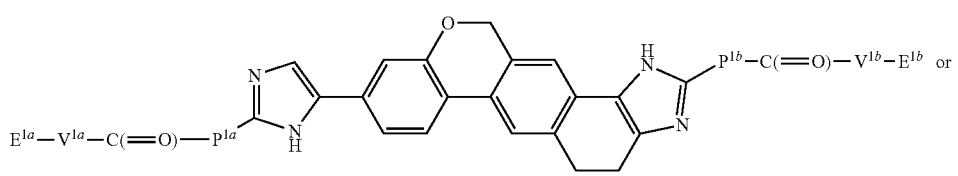

(A3) or

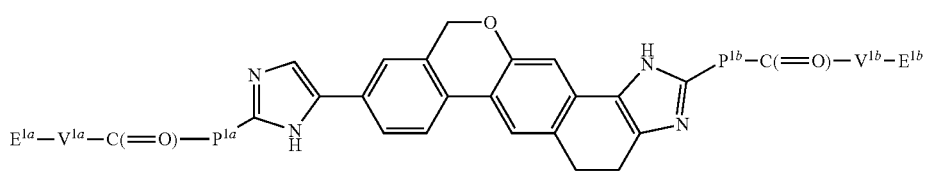

(A4)

wherein the imidazole ring shown in formula A1, A2, A3, and A4 is optionally substituted with one or more halo, haloalkyl, cyano, or alkyl;

or a pharmaceutically acceptable salt or prodrug thereof.

In one embodiment the disclosure provides a compound which has formula:

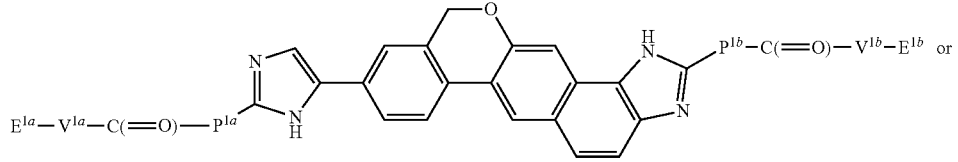
(A2)

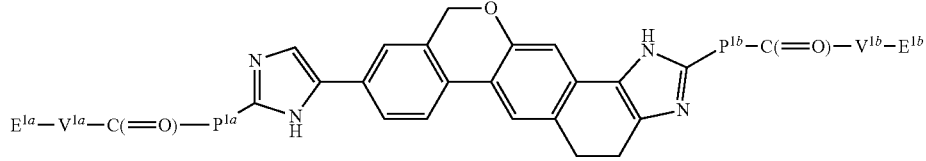
(A4)

wherein the imidazole ring shown in formula A2 and A4 is optionally substituted with one or more halo, haloalkyl, cyano, or alkyl;

or a pharmaceutically acceptable salt or prodrug thereof.

In one embodiment $P^{1a}$ and $P^{1b}$ are each independently:

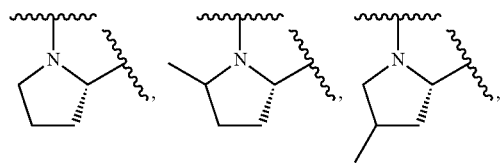

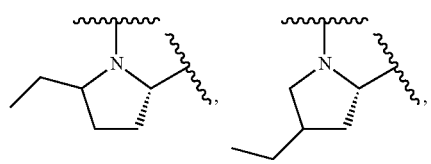

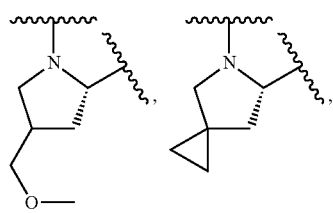

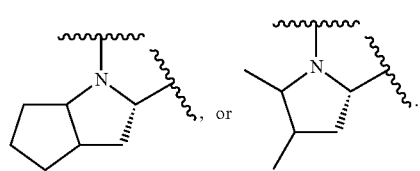

In one embodiment $V^{1a}$ and $V^{1b}$ are each independently:

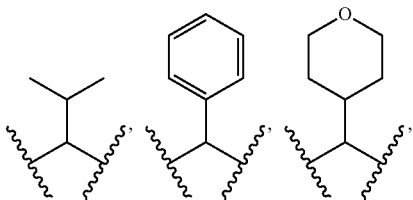

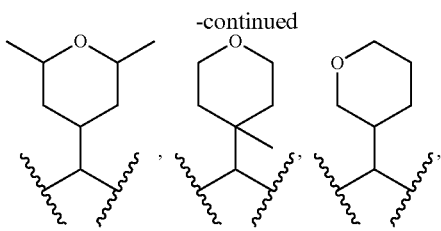
-continued

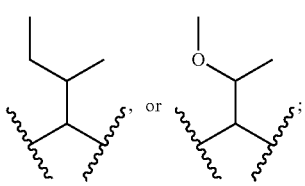

provided that at least one of $V^{1a}$ and $V^{1b}$ is

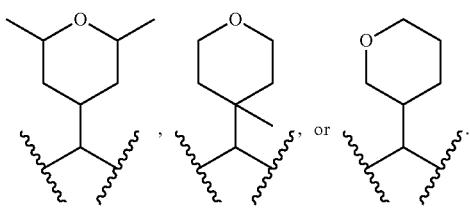

In one embodiment, provided is a compound of formula (I):

$$E^{1a}\text{-}V^{1a}\text{—}C(=O)\text{—}P^{1a}\text{—}W^{1a}\text{—}P^{1b}\text{—}C(=O)\text{—}V^{1b}\text{-}E^{1b}$$ (I)

wherein:

$W^{1a}$ is

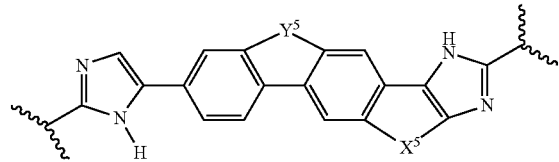

and $W^{1a}$ is optionally substituted with one or more halo, alkyl, haloalkyl, or cyano;

$Y^5$ is —O—CH$_2$—, or —CH$_2$—O—;

$X^5$ is —CH$_2$—CH$_2$—, or —CH═CH—;

$P^{1a}$ and $P^{1b}$ are each independently:

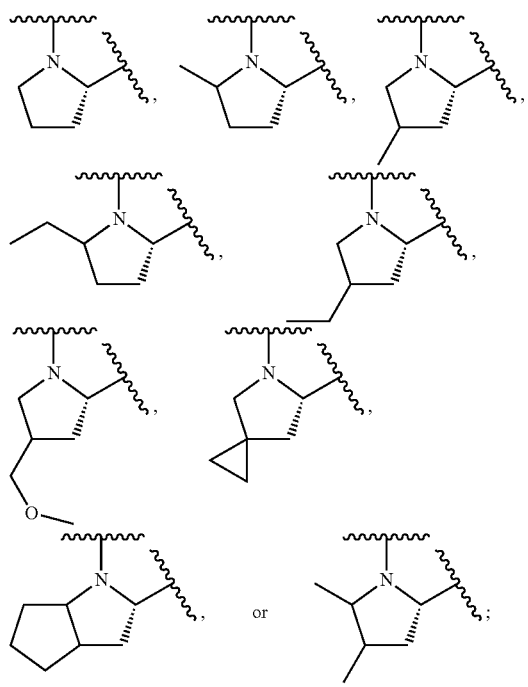

$V^{1a}$ and $V^{1b}$ are each independently:

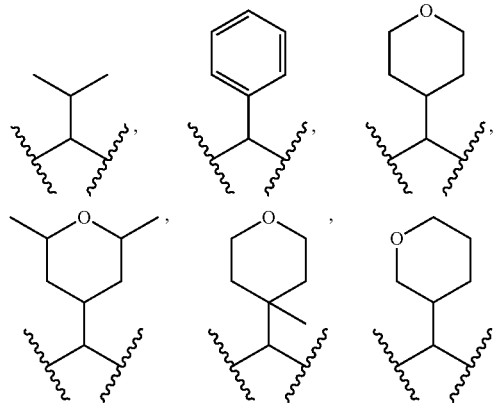

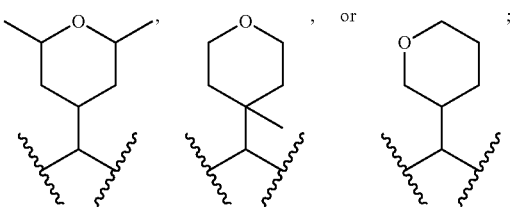

provided that at least one of $V^{1a}$ and $V^{1b}$ is

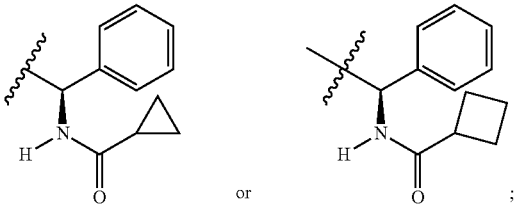 [SMILES: *[C@H](NC(=O)C1CC1)c1ccccc1 ; *[C@H](NC(=O)C1CCC1)c1ccccc1]

$E^{1a}$ and $E^{1b}$ are each independently —N(H)(alkoxycarbonyl), —N(H)(cycloalkylcarbonyl), or —N(H)(cycloalkyloxycarbonyl); or $E^{1a}$-$V^{1a}$ taken together are $R^{9a}$; or $E^{1b}$-$V^{1b}$ taken together are $R^{9b}$; and $R^{9a}$ and $R^{9b}$ are each independently:

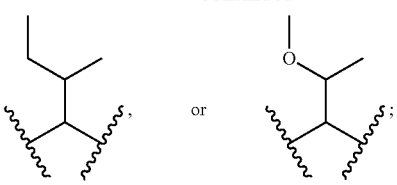

or a pharmaceutically acceptable salt or prodrug thereof.

In one embodiment, one of $V^{1a}$ and $V^{1b}$ is:

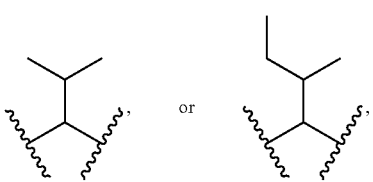

and the other of $V^{1a}$ and $V^{1b}$ is

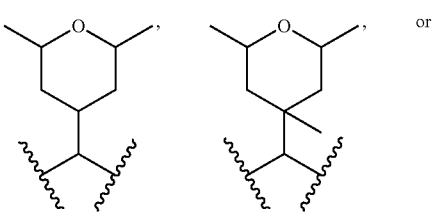

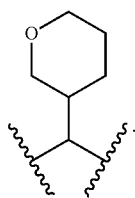
In one embodiment, one of $V^{1a}$ and $V^{1b}$ is:
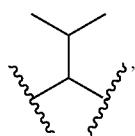
and the other of $V^{1a}$ and $V^{1b}$ is
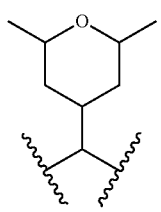     or
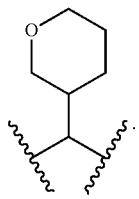
In one embodiment, one of $V^{1a}$ and $V^{1b}$ is:
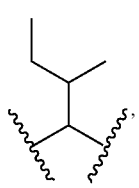
and the other of $V^{1a}$ and $V^{1b}$ is
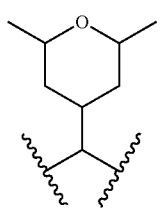 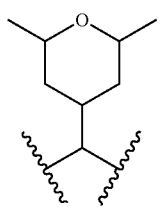     or
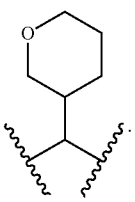
In one embodiment, one of $V^{1a}$ and $V^{1b}$ is:
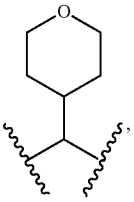
and the other of $V^{1a}$ and $V^{1b}$ is
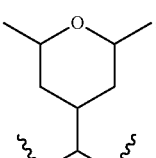     or
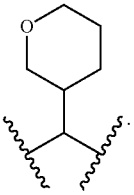
In one embodiment, one of $V^{1a}$ and $V^{1b}$ is:
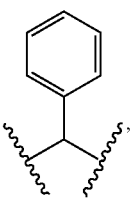
and the other of $V^{1a}$ and $V^{1b}$ is
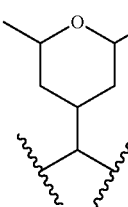 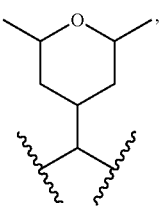     or -continued

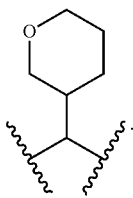

In one embodiment, one of $V^{1a}$ and $V^{1b}$ is:

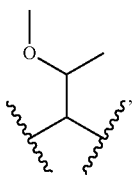 [SMILES: *C(*)C(C)OC]

and the other of $V^{1a}$ and $V^{1b}$ is

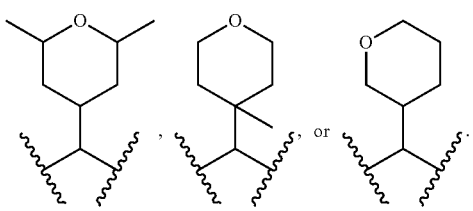

In one embodiment, one of $V^{1a}$ and $V^{1b}$ is:

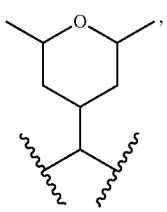

and the other of $V^{1a}$ and $V^{1b}$ is

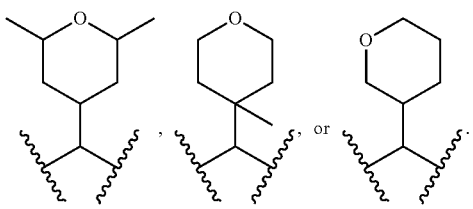

In one embodiment, one of $V^{1a}$ and $V^{1b}$ is:

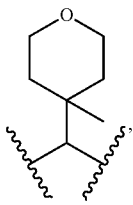 [SMILES: *C(*)C1(C)CCOCC1]

and the other of $V^{1a}$ and $V^{1b}$ is

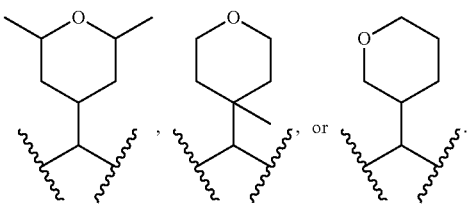

In one embodiment, one of $V^{1a}$ and $V^{1b}$ is:

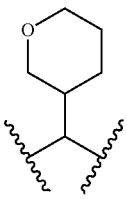

and the other of $V^{1a}$ and $V^{1b}$ is

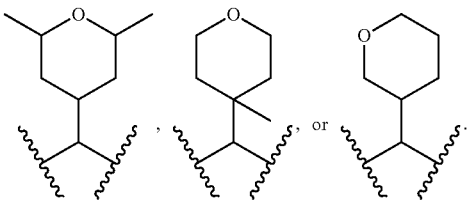

In one embodiment, $P^{1a}$ and $P^{1b}$ are each independently:

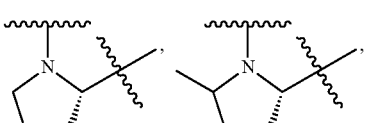

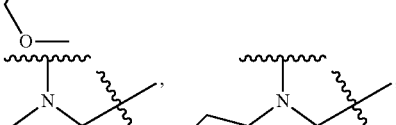

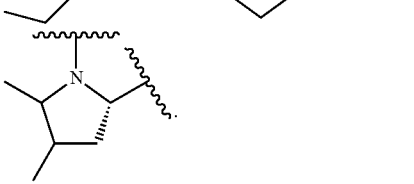

In one embodiment, one of $V^{1a}$ and $V^{1b}$ is:

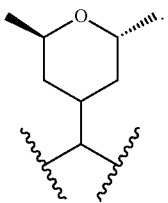

In one embodiment, both of $V^{1a}$ and $V^{1b}$ are:

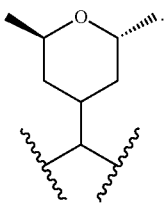

In one embodiment, one of $V^{1a}$ and $V^{1b}$ is:

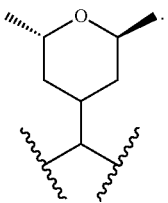

In one embodiment, both of $V^{1a}$ and $V^{1b}$ are:

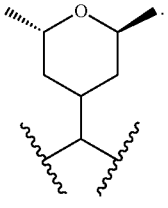

In one embodiment, one of $V^{1a}$ and $V^{1b}$ is:

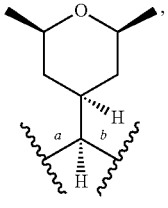

provided that bond (a) is connected to $E^{1a}$ or $E^{1b}$ and bond (b) is connected to the —C(=O)— group of formula (I) or (A1, A2, A3, or A4).

In one embodiment, one of $V^{1a}$ and $V^{1b}$ is:

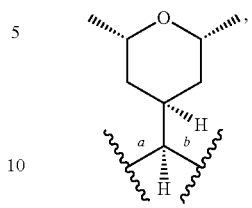

provided that bond (a) is connected to $E^{1a}$ or $E^{1b}$ and bond (b) is connected to the —C(=O)— group of formula (I) or (A1, A2, A3, or A4).

In one embodiment, one of $V^{1a}$ and $V^{1b}$ is:

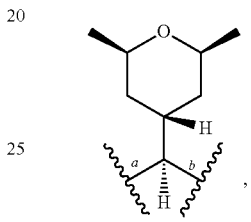

provided that bond (a) is connected to $E^{1a}$ or $E^{1b}$ and bond (b) is connected to the —C(=O)— group of formula (I) or (A1, A2, A3, or A4).

In one embodiment, one of $V^{1a}$ and $V^{1b}$ is:

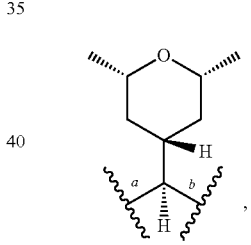

provided that bond (a) is connected to $E^{1a}$ or $E^{1b}$ and bond (b) is connected to the —C(=O)— group of formula (1) or (A1, A2, A3, or A4).

In one embodiment, $P^{1a}$ and $P^{1b}$ are each independently:

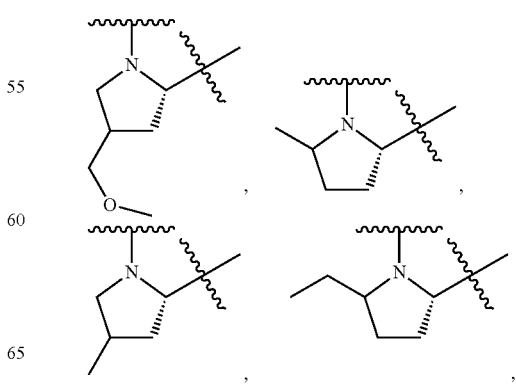

, or

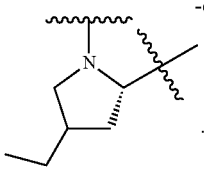
In one embodiment, one of $P^{1a}$ and $P^{1b}$ is:
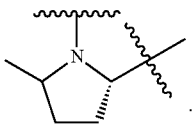
In one embodiment, one of $P^{1a}$ and $P^{1b}$ is:
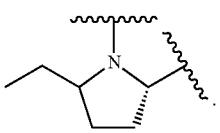
In one embodiment, both of $P^{1a}$ and $P^{1b}$ are:
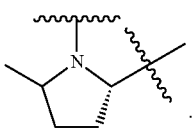
In one embodiment, —$V^{1a}$—C(═O)—$P^{1a}$— and —$P^{1b}$—C(═O)—$V^{1b}$— are each independently:
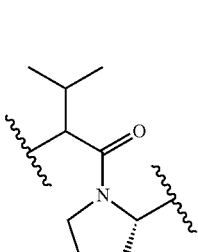 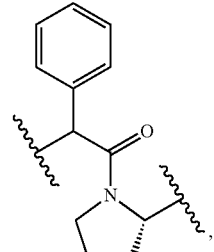
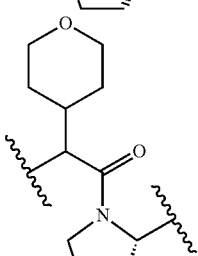 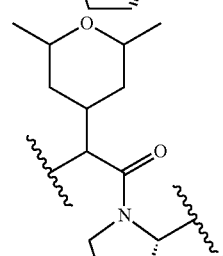
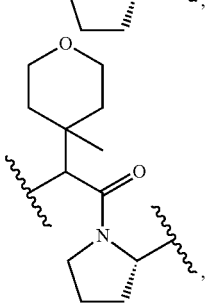 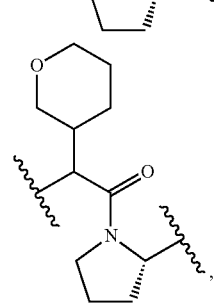
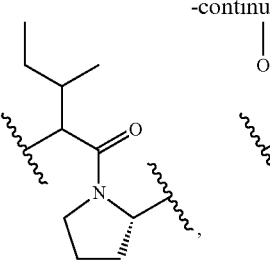 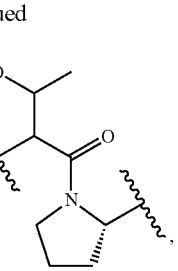
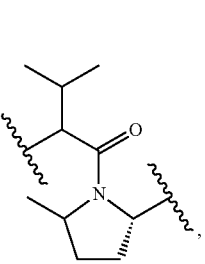 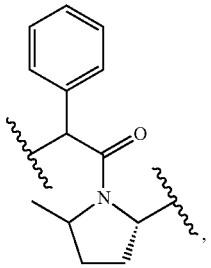
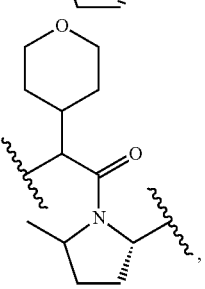 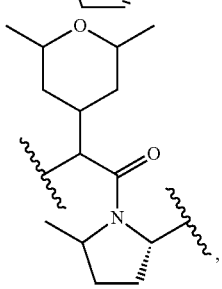
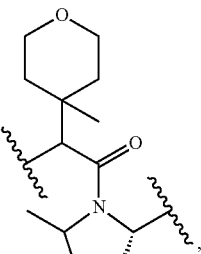 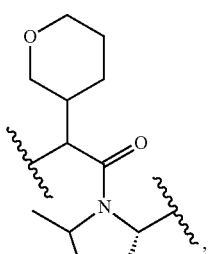
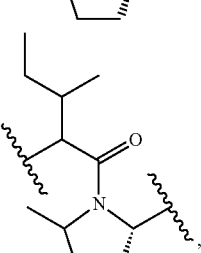 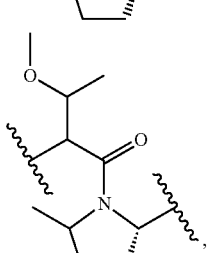
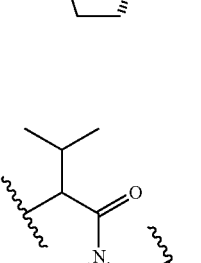 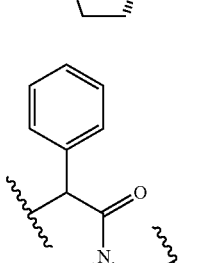

61
-continued
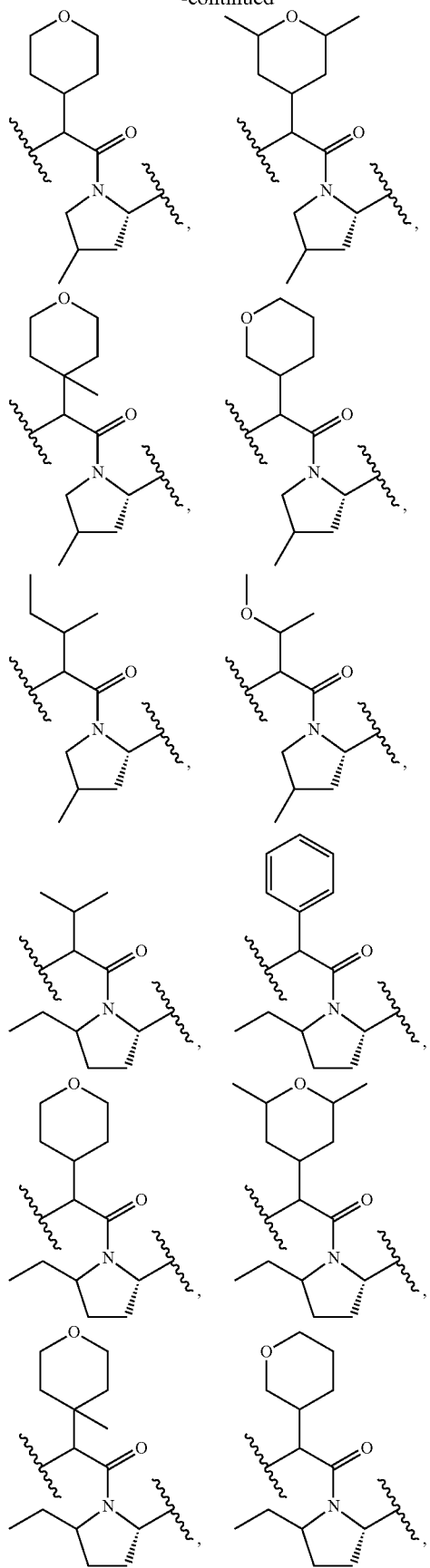
62
-continued
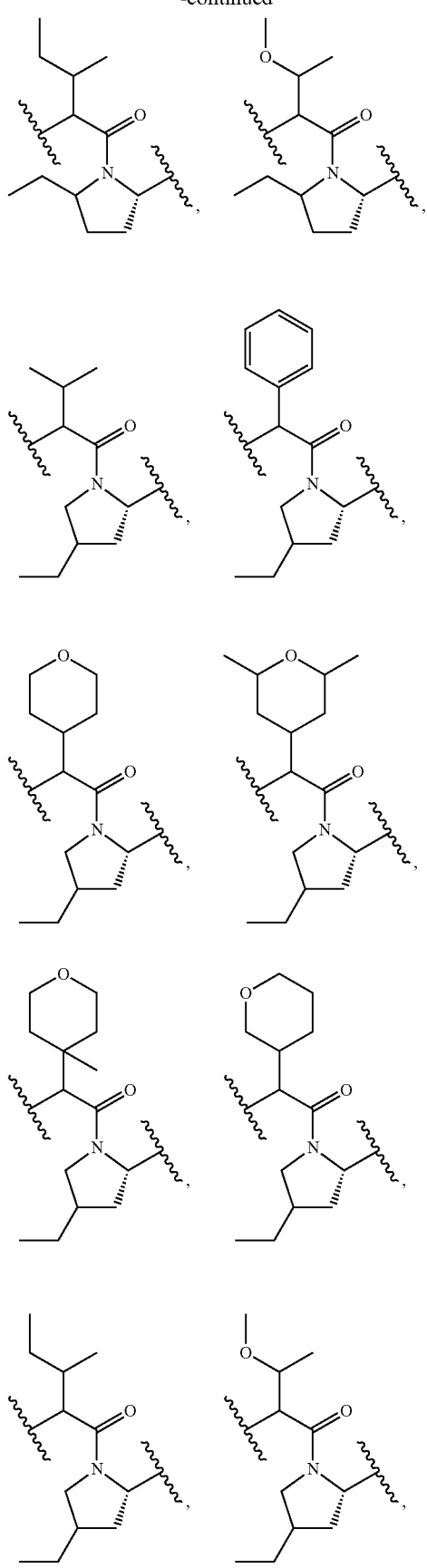

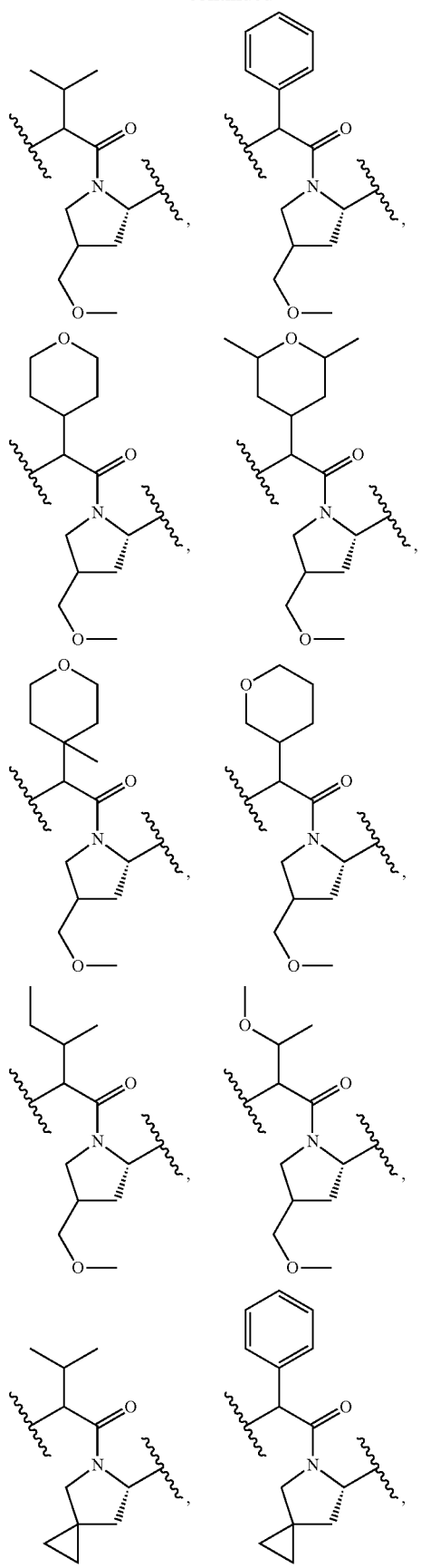
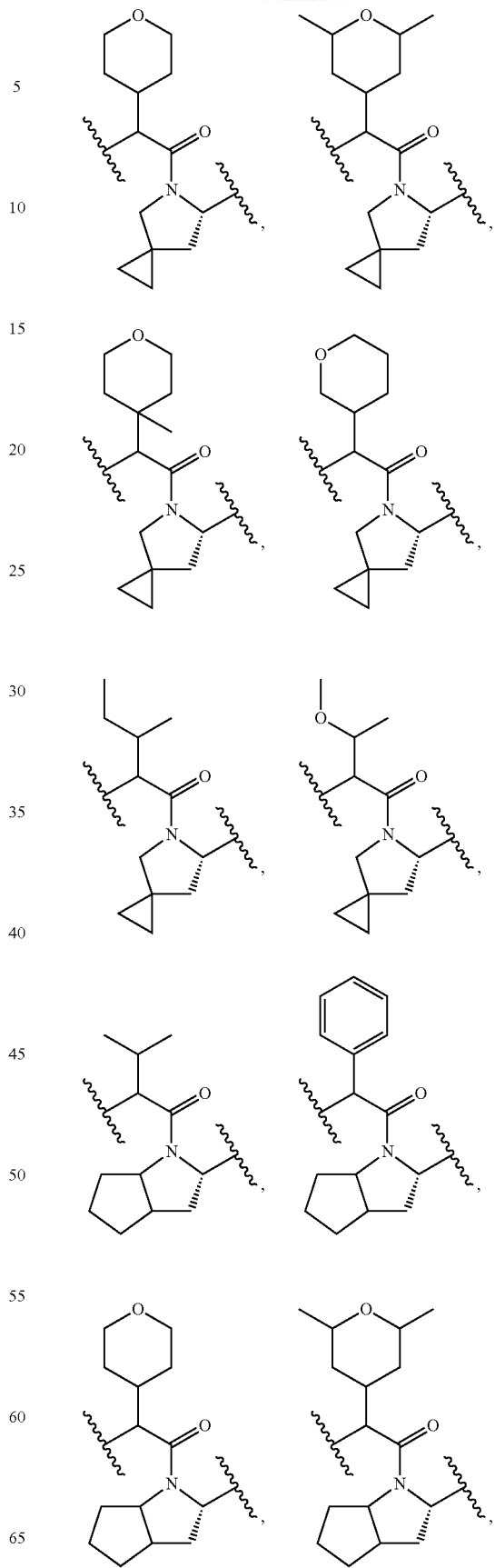

-continued
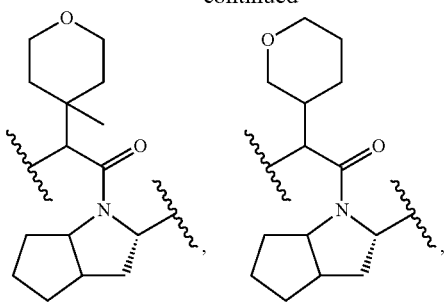
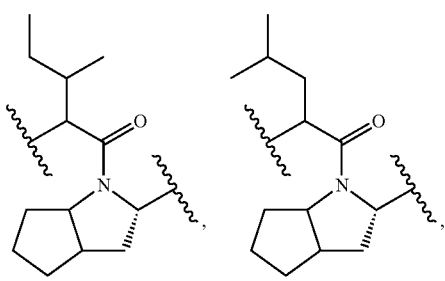
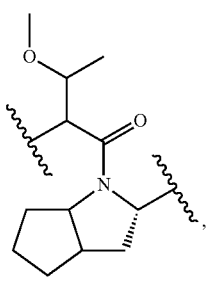
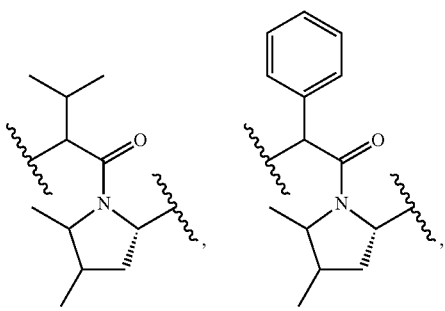
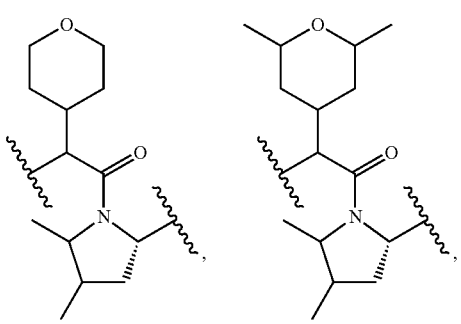
-continued
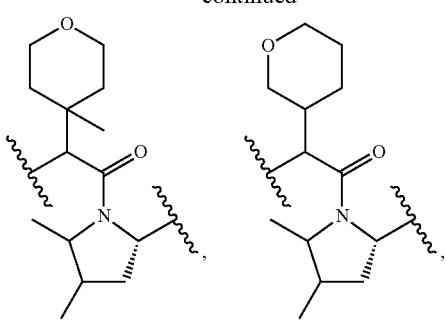
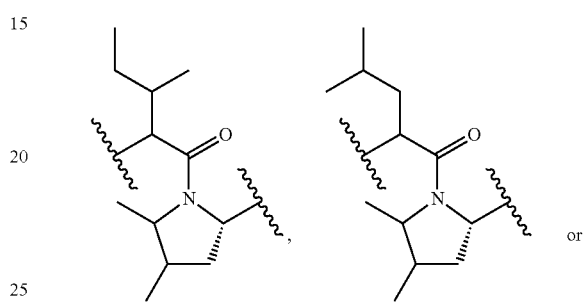
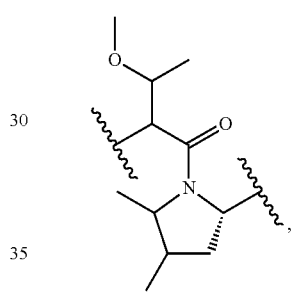
provided that at least one of $V^{1a}$ and $V^{1b}$ is
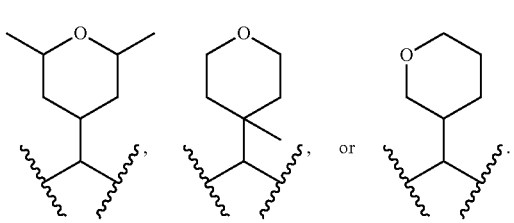
In one embodiment, —$V^{1a}$—C(=O)—$P^{1a}$— and —$P^{1b}$—C(=O)—$V^{1b}$— are each independently:
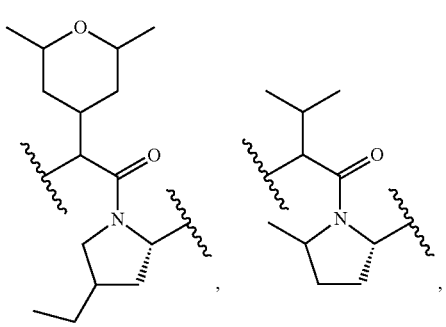

-continued
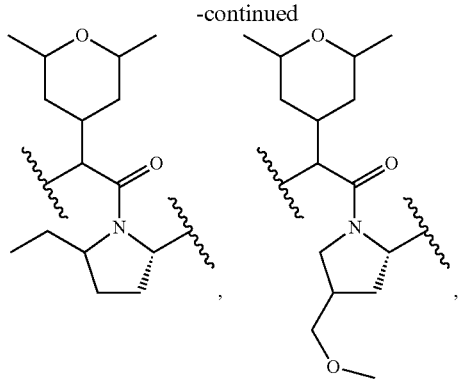
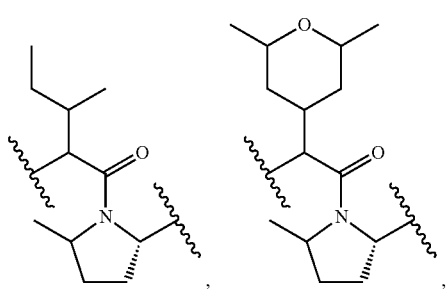
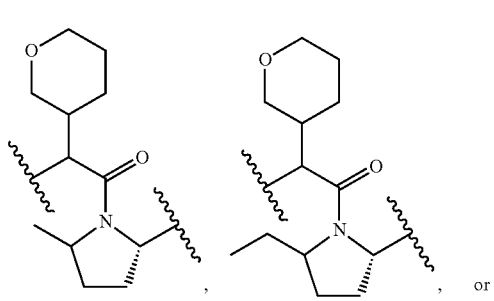
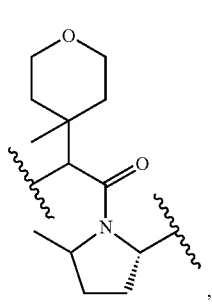
provided that at least one of $V^{1a}$ and $V^{1b}$ is
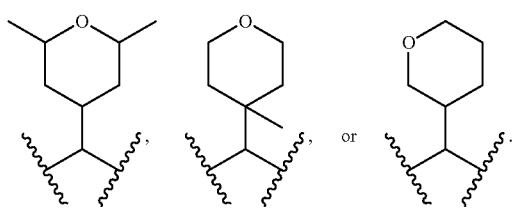
In one embodiment, one of —$V^{1a}$—C(=O)—$P^{1a}$— and —$P^{1b}$—C(=O)—$V^{1b}$— is:
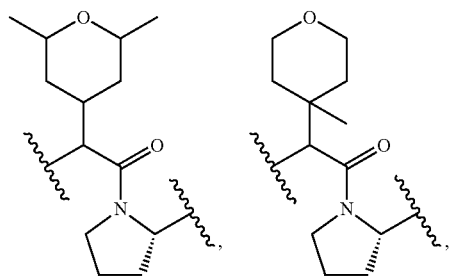
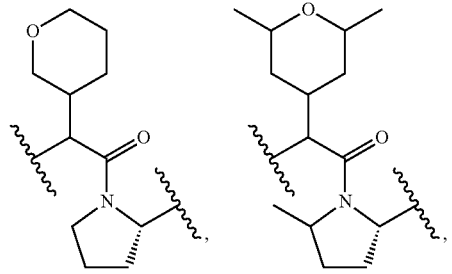
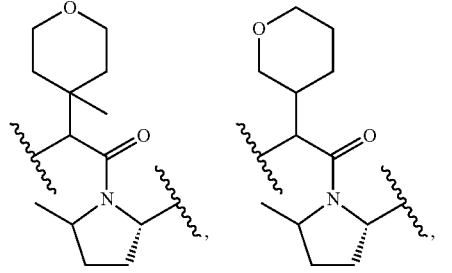
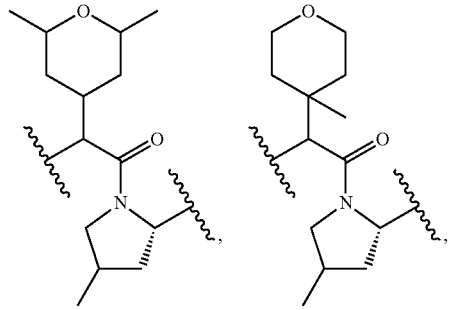
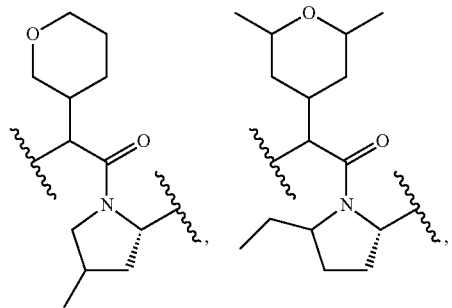

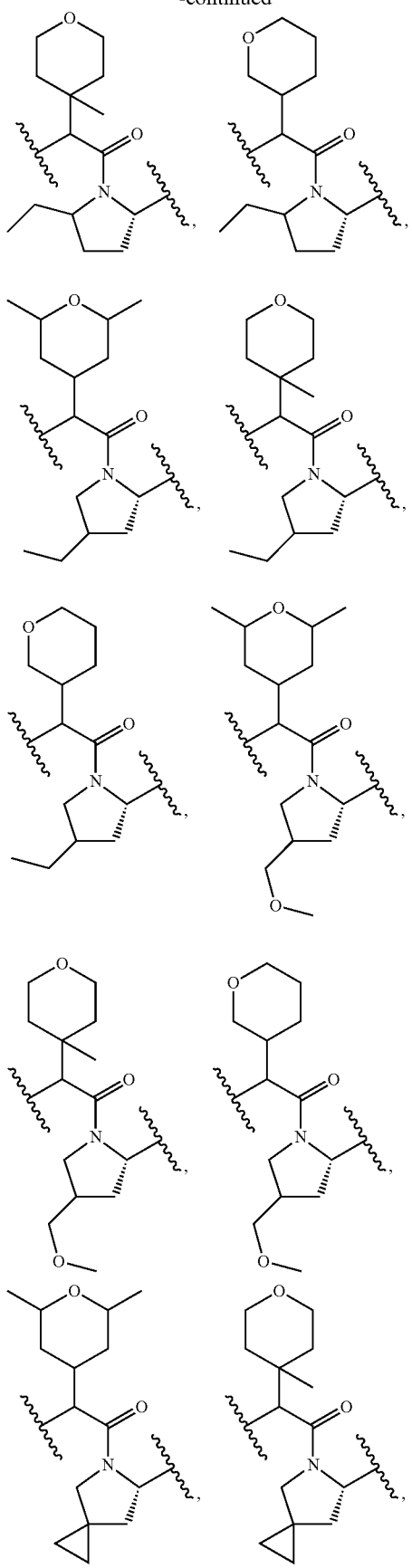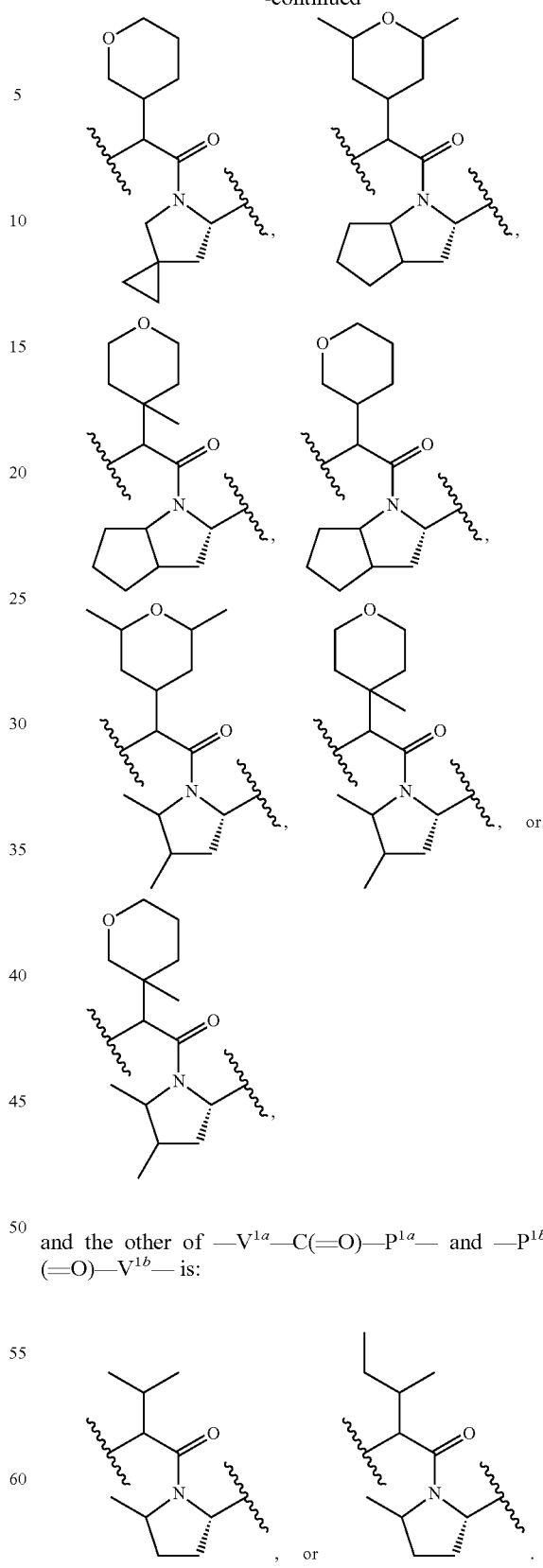
and the other of —V$^{1a}$—C(=O)—P$^{1a}$— and —P$^{1b}$—C(=O)—V$^{1b}$— is:
In one embodiment, one of —V$^{1a}$—C(=O)—P$^{1a}$— and —P$^{1b}$—C(=O)—V$^{1b}$— is:

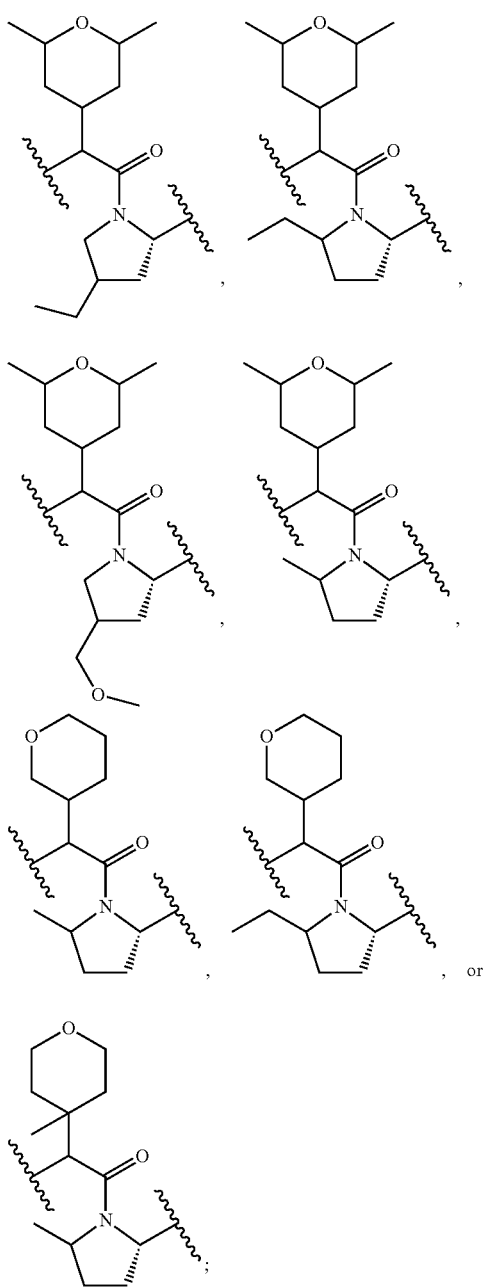

and the other of —V$^{1a}$—C(=O)—P$^{1a}$— and —P$^{1b}$—C(=O)—V$^{1b}$— is:

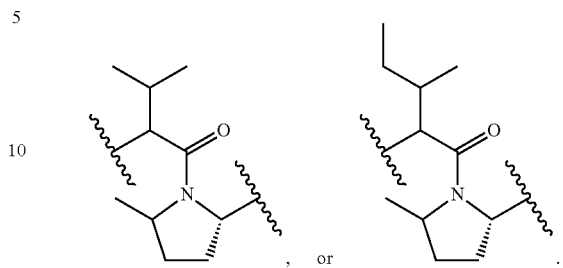

In one embodiment, both of —V$^{1a}$—C(=O)—P$^{1a}$— and —P$^{1b}$—C(=O)—V$^{1b}$— are:

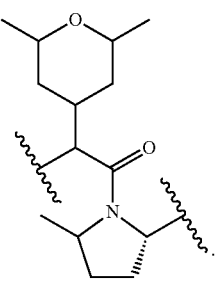

In one embodiment, at least one of E$^{1a}$ and E$^{1b}$ is —N(H)(alkoxycarbonyl).

In one embodiment, both of E$^{1a}$ and E$^{1b}$ are —N(H)(alkoxycarbonyl).

In one embodiment, at least one of E$^{1a}$ and E$^{1b}$ is —N(H)C(=O)OMe.

In one embodiment, both of E$^{1a}$ and E$^{1b}$ are —N(H)C(=O)OMe.

In one embodiment, the disclosure provides a compound of formula:

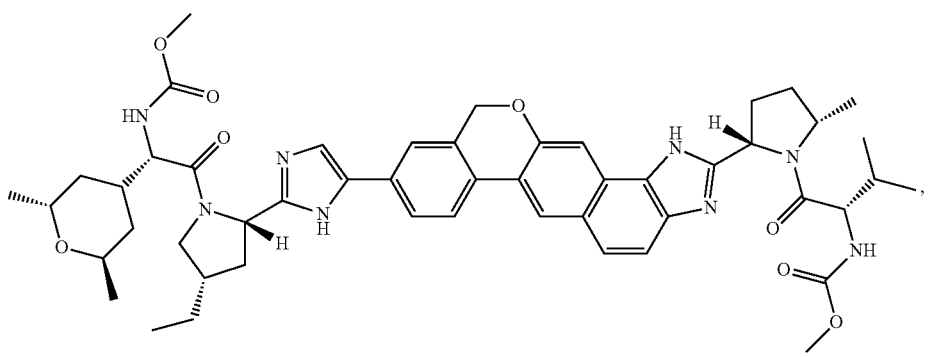

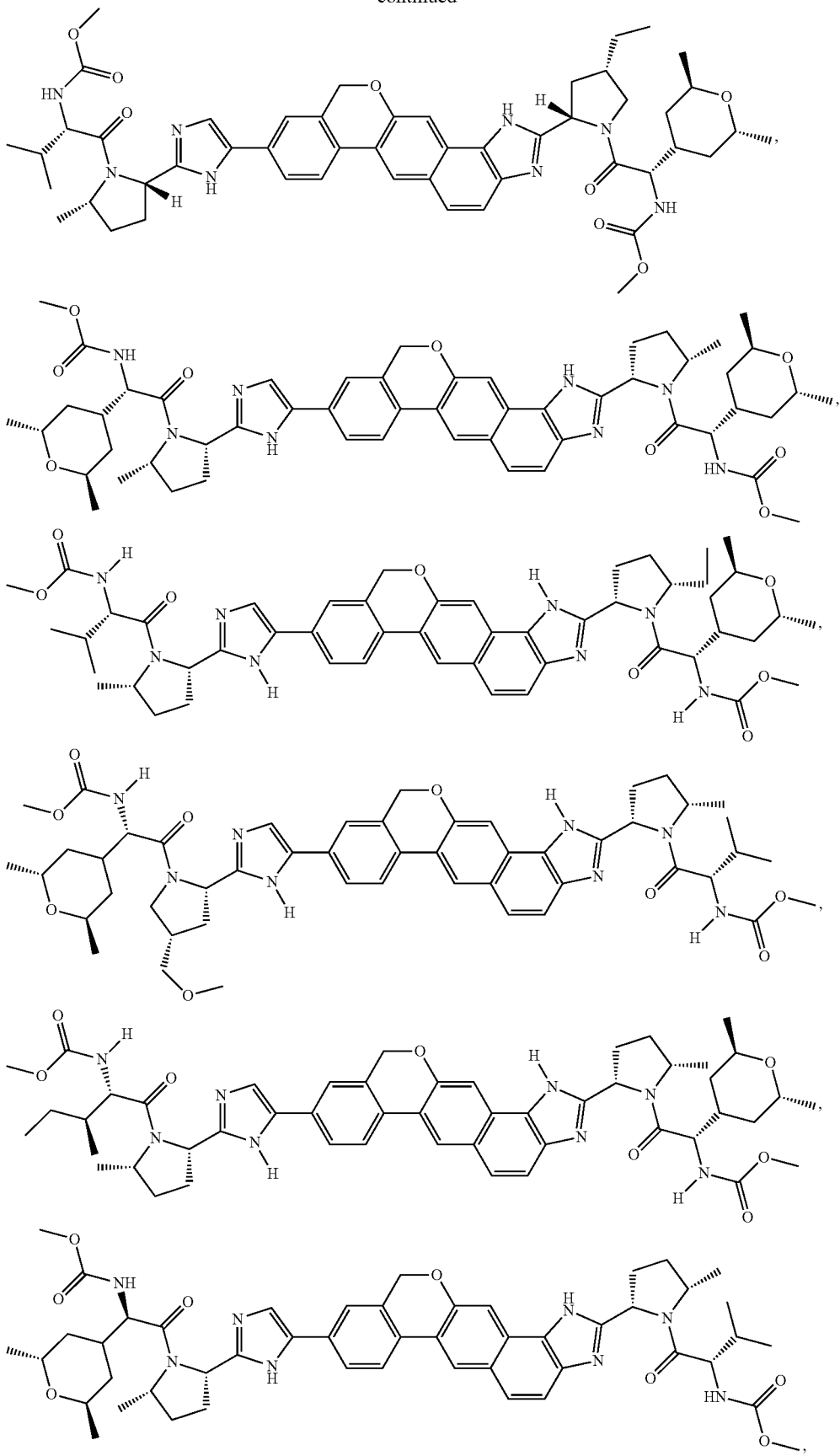

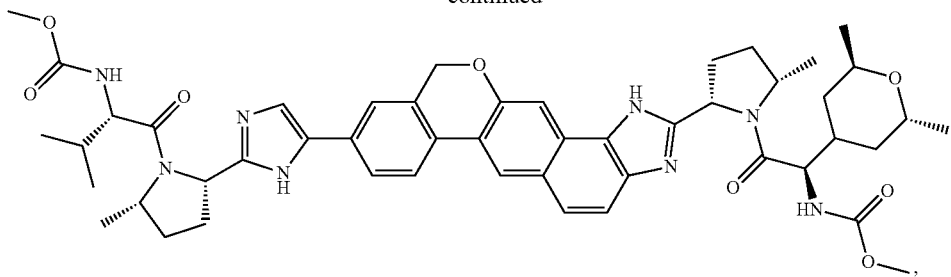
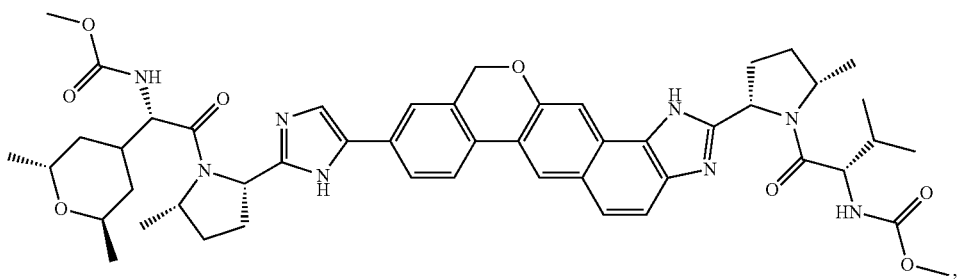
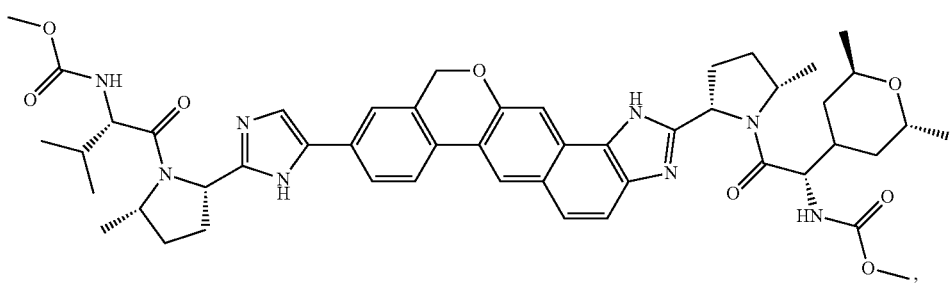
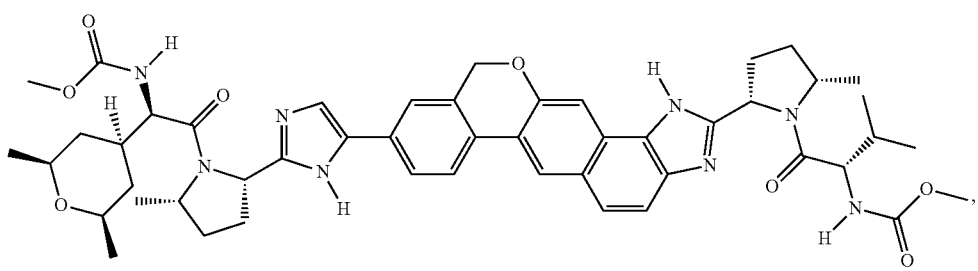
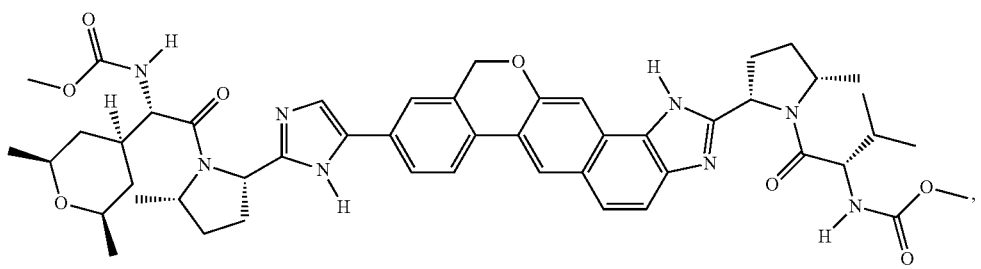
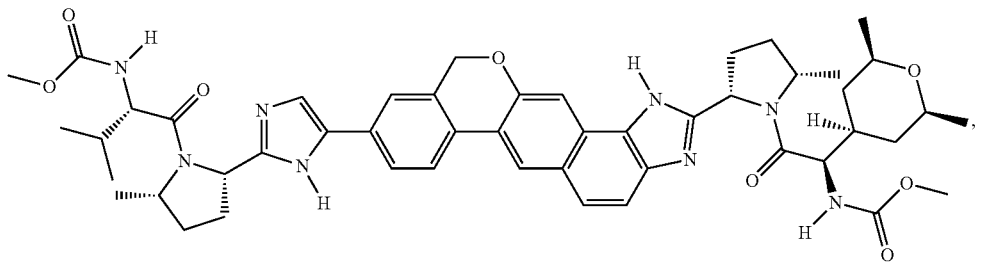

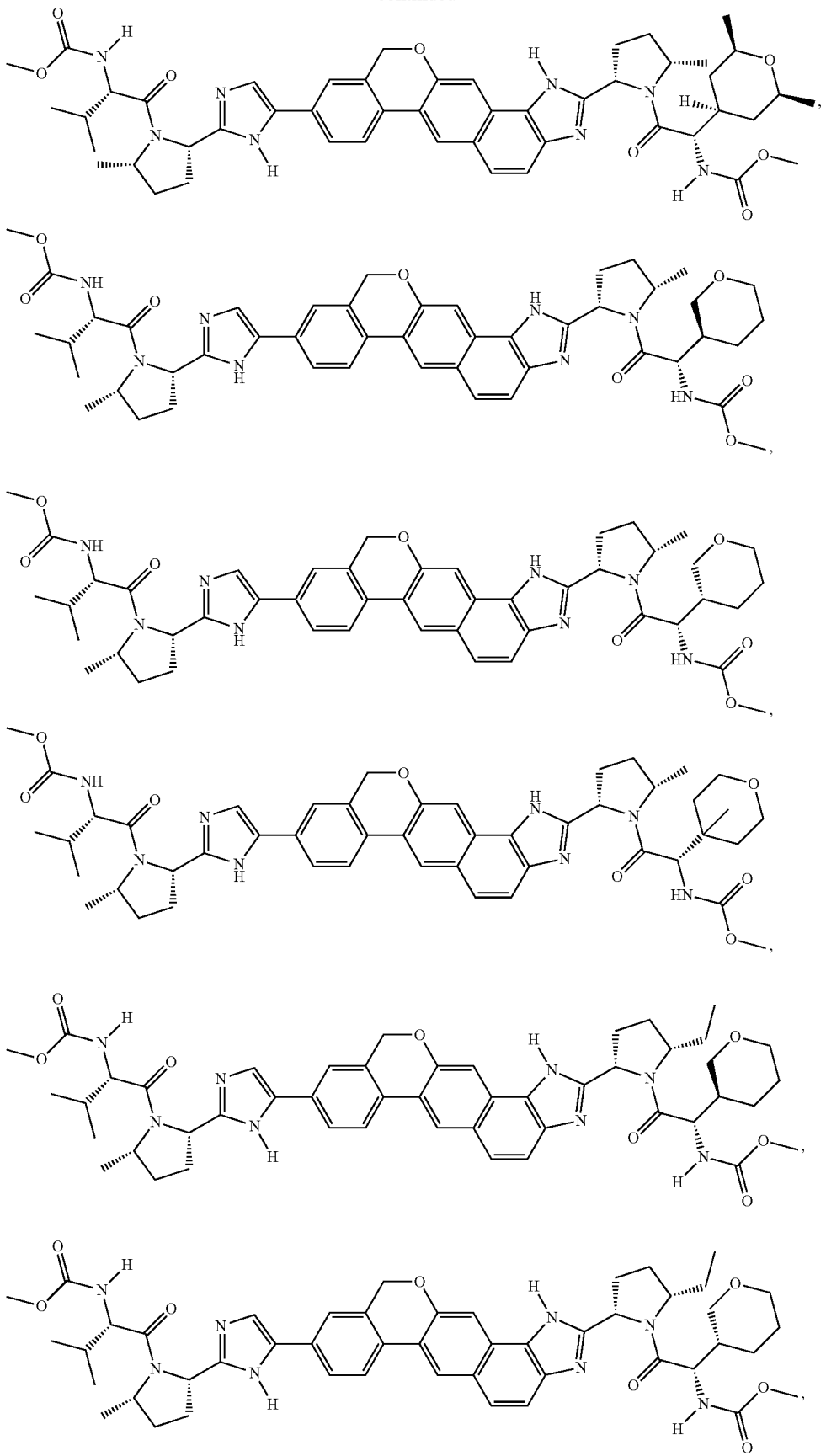

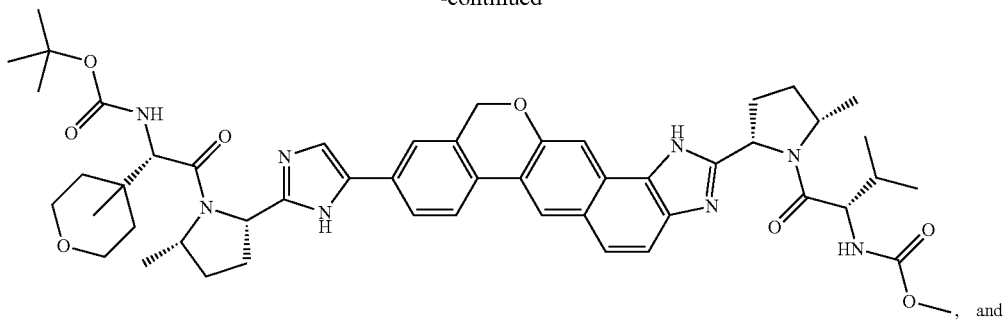
, and
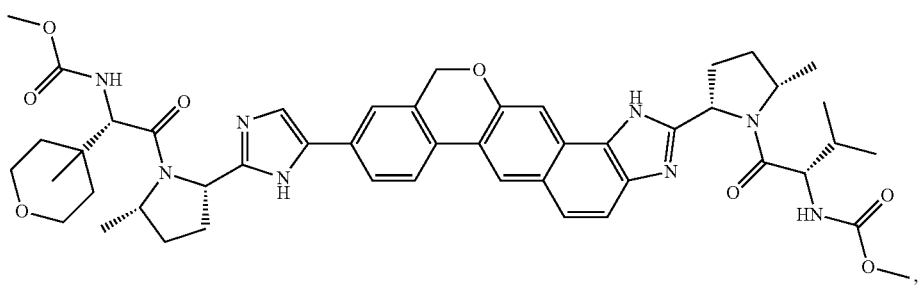
,
or a pharmaceutically acceptable salt or prodrug thereof.
In another embodiment, the disclosure provides a compound of formula:
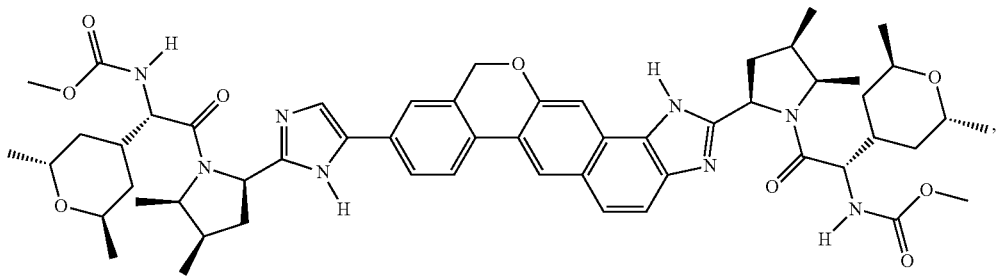
,
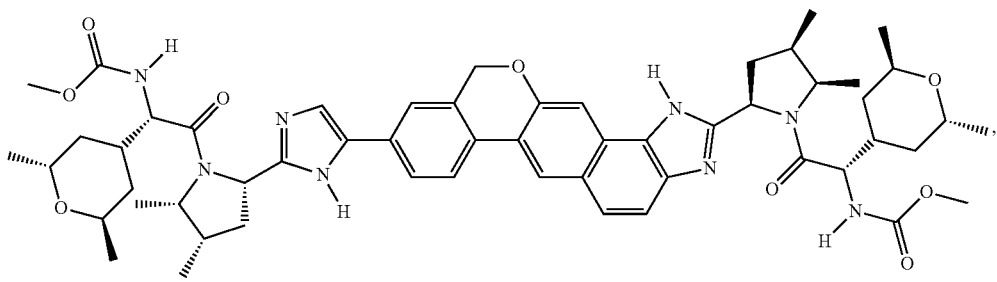
,
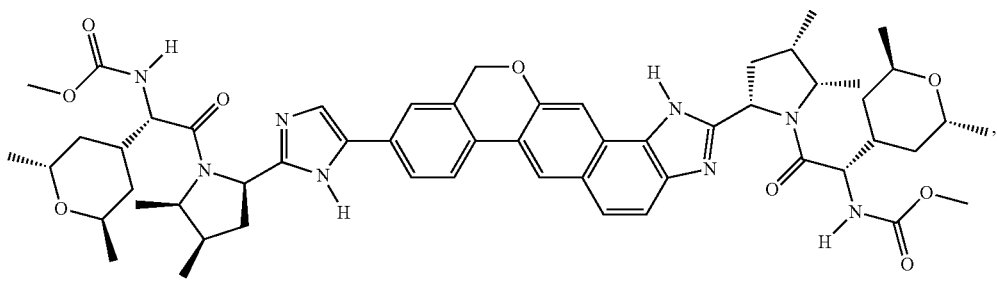
, -continued
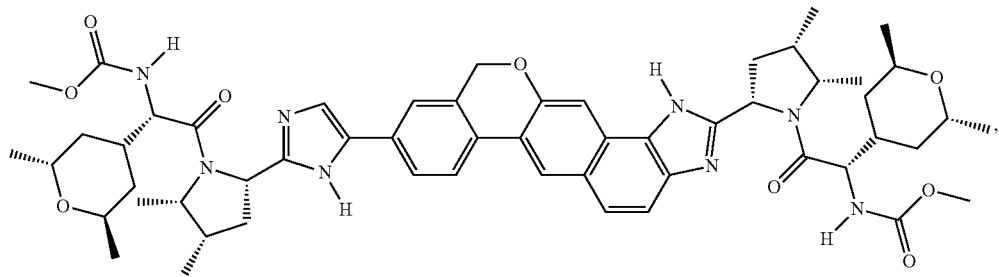
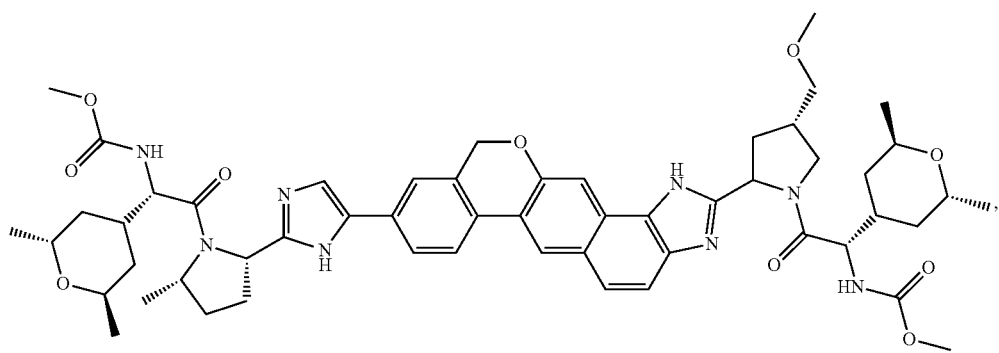
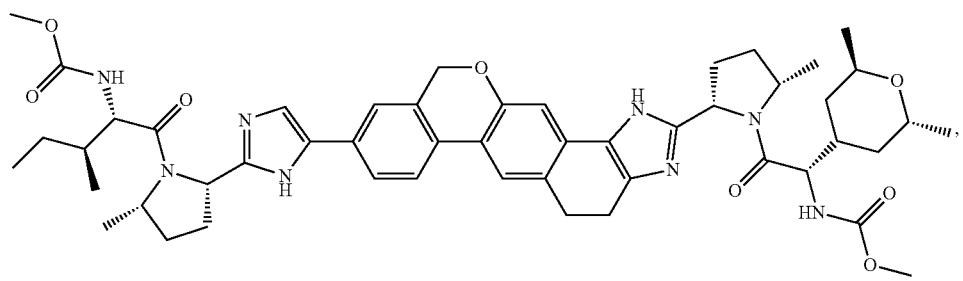
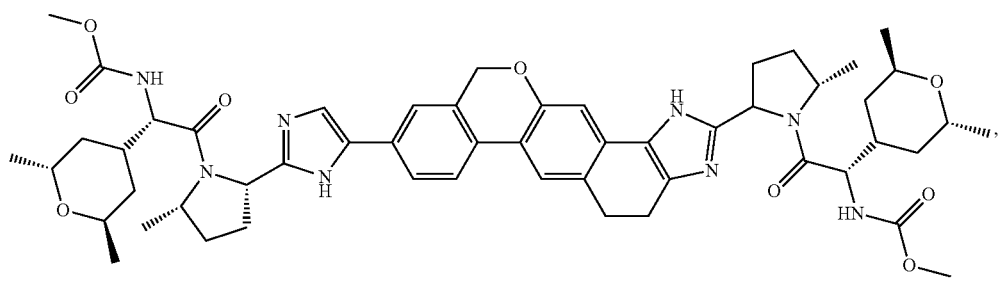
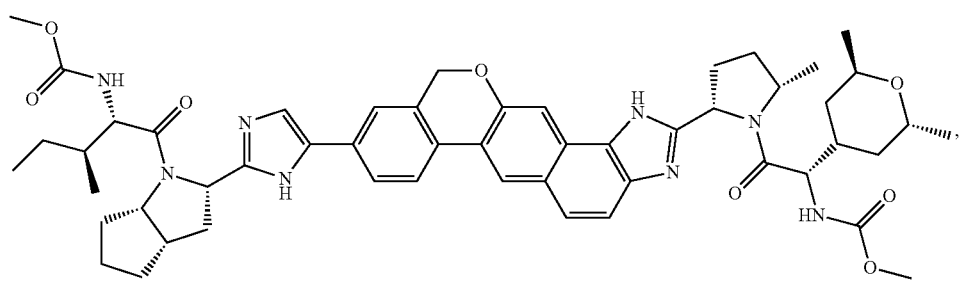

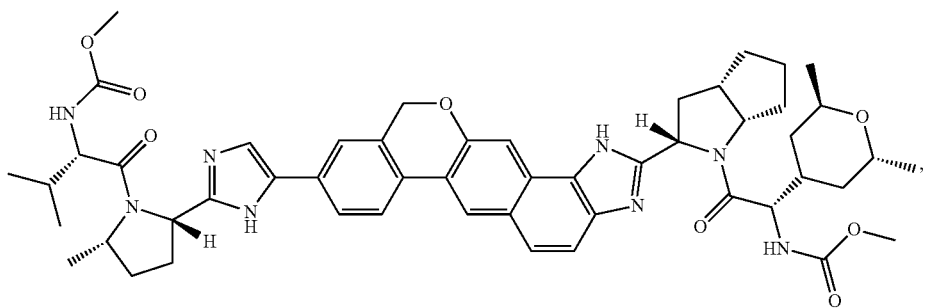
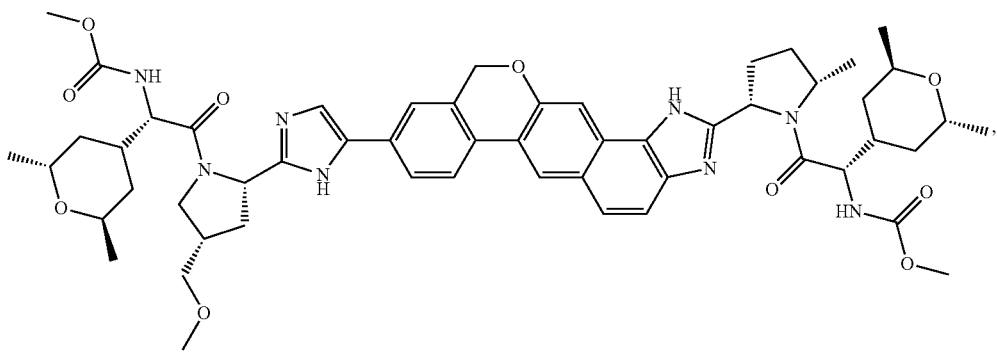
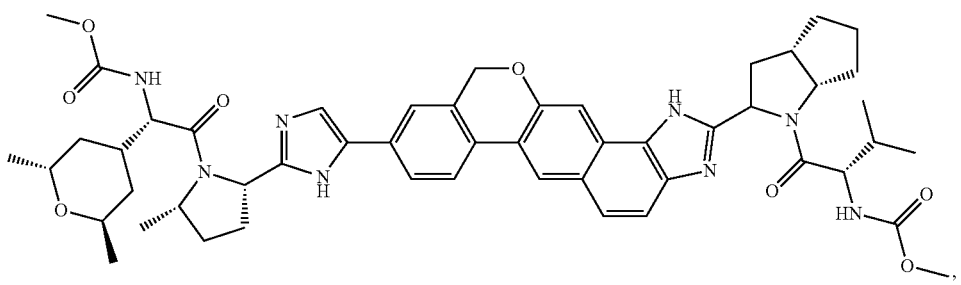
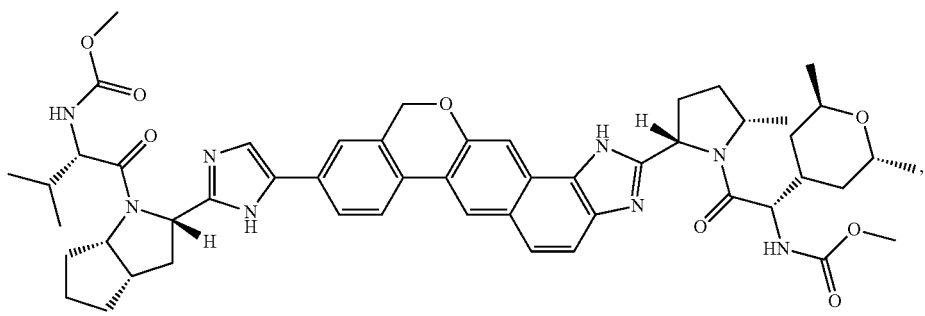

-continued
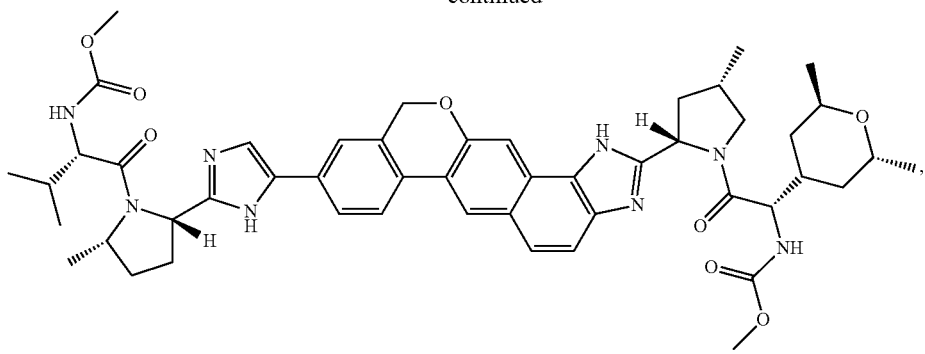
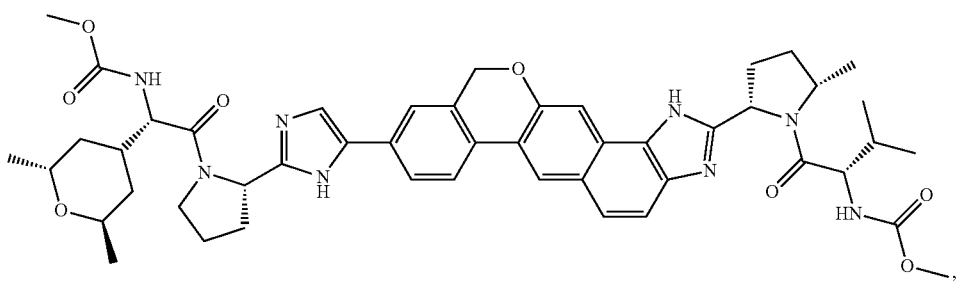
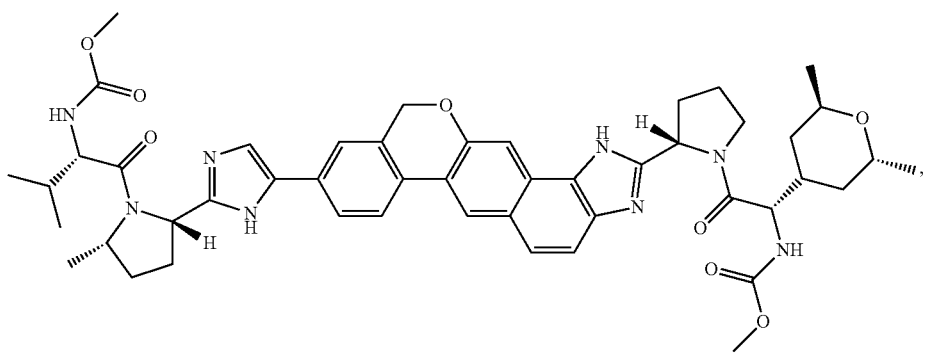
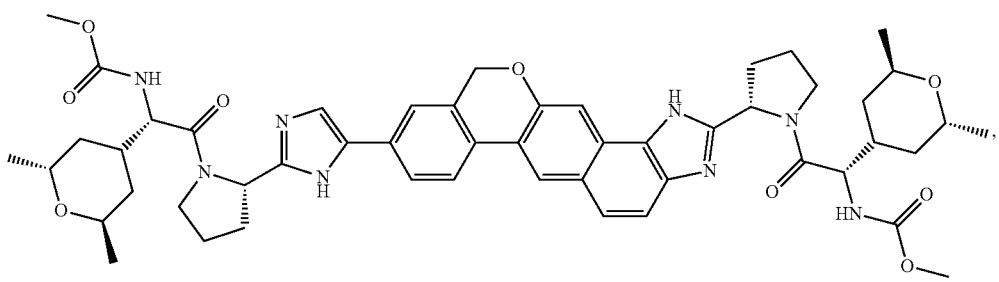
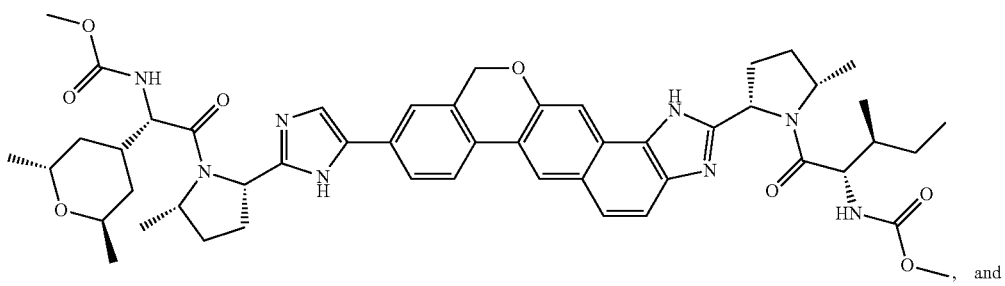, and

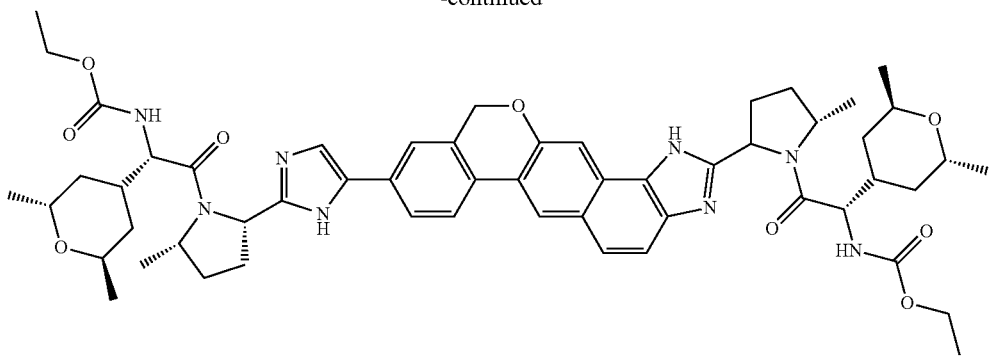

or a pharmaceutically acceptable salt or prodrug thereof.

In one embodiment, the disclosure provides a compound of formula:

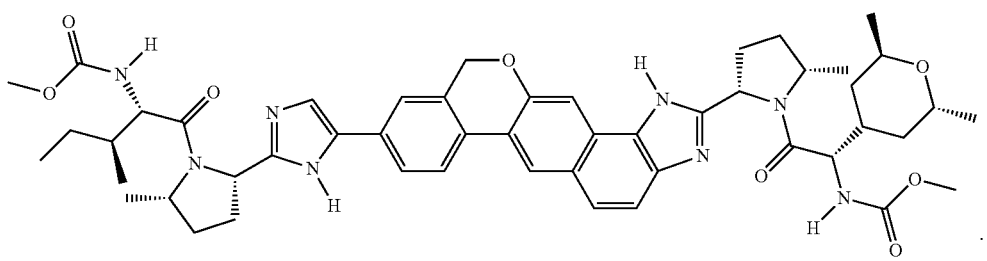

In one embodiment, the disclosure provides a compound of formula:

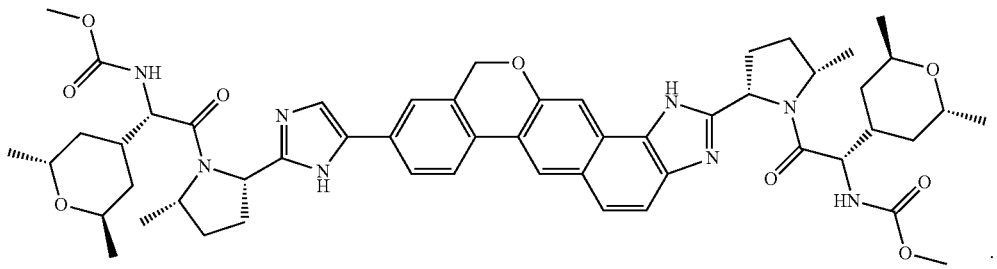

The disclosure will now be illustrated by the following non-limiting Examples. The following abbreviations are used throughout the specification, including the Examples.

| | |
|---|---|
| % F | % Bioavailability |
| (g) | Gas |
| °C. | Degree Celsius |
| Ac | Acetate |
| ACN | Acetonitrile |
| approx./apprx. | Approximate |
| AUC | Area under the curve |
| Bn | Benzyl |
| BOC/Boc | tert-Butoxycarbonyl |
| br | Broad |
| calc'd | Calculated |
| $CC_{50}$ | 50% Cytotoxicity concentration |
| d | Doublet |
| dba | dibenzalacetone |
| DCM | Dichloromethane |
| dd | Doublet of doublets |
| DIPEA/DIEA | N,N-Diisopropylethylamine |
| DMA | N,N-Dimethylacetamide |
| DMAP | 4-Dimethylaminopyridine |
| DMEM | Eagle's minimal essential medium |
| DMF | Dimethylformamide |
| DMSO/dmso | Dimethylsulfoxide |
| dppf | 1,1'-bis(diphenylphosphanyl) ferrocene |
| $EC_{50}$ | Half maximal effective concentration |
| EDTA | Ethylenediaminetetraacetic acid |
| ESI | Electrospray ionization |
| Et | Ethyl |
| FBS | Fetal bovine serum |
| g | Gram |
| HATU | 2-(1H-7-Azabenzotriazol-1-yl)-1,1,3,3-tetramethyl uronium hexafluorophosphate Methanaminium |
| HPLC | High performance liquid chromatography |
| hr/h | Hour |
| Hz | Hertz |

| | |
|---|---|
| i.d. | Inner diameter |
| IPAm | Isopropylamine |
| IV | Intravenous |
| J | Coupling constant |
| L | Liter |
| LCMS | Liquid chromatography mass spectrometry |
| M | Molar |
| m | Multiplet |
| m/z | Mass to charge |
| M+ | Mass peak |
| Me | Methyl |
| mg | Milligram |
| MHz | Megahertz |
| min | Minute |
| mL | Milliliter |
| mL | Milliliter |
| mM | Millimolar |
| mm | Millimeter |
| mmol | Millimole |
| MS | Mass spectrometry |
| MTBE | Methyl tert-butyl ether |
| N | Normal |
| NADPH | Nicotinamide adenine dinucleotide phosphate |
| NBS | N-Bromosuccinimide |
| nm | Nanometer |
| NMR | Nuclear magnetic resonance |
| o/n | Over night |
| Papp | Apparent permeability |
| PBS | Phosphate buffer system |
| Pd/C | Palladium on carbon |
| PEG | Polyethylene glycol |
| Ph | Phenyl |
| Piv | Pivalate |
| Py/pyr | Pyridine |
| q | Quartet |
| quant | Quantitative |
| rt/RT | Room temperature |
| s | Singlet |
| SFC | Supercritical fluid chromatography |
| SPhos/S-Phos | 2-Dicyclohexylphosphino-2',6'-dimethoxybiphenyl |
| SRM | Selected reaction monitoring |
| t | Triplet |
| t-Bu | tert-Butyl |
| TEA | Triethylamine |
| TEMPO | (2,2,6,6-Tetramethyl-piperidin-1-yl)oxyl |
| Tf | Trifluoromethanesulfonate |
| TFA | Trifluoroacetic acid |
| THF | Tetrahydrofuran |
| TLC | Thin layer chromatography |
| TMS | Trimethylsilyl |
| UV | Ultraviolet |
| w/w | Weight to weight |
| X-Phos/XPhos | 2-Dicyclohexylphosphino-2',4',6'-triisopropylbiphenyl |
| δ | Chemical shift |
| μL | Microliter |
| μm | Micromolar |

EXAMPLES

Intermediate 1

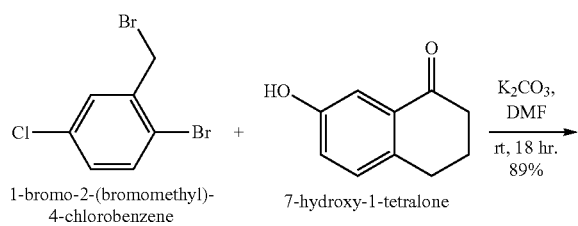

1-bromo-2-(bromomethyl)-4-chlorobenzene + 7-hydroxy-1-tetralone

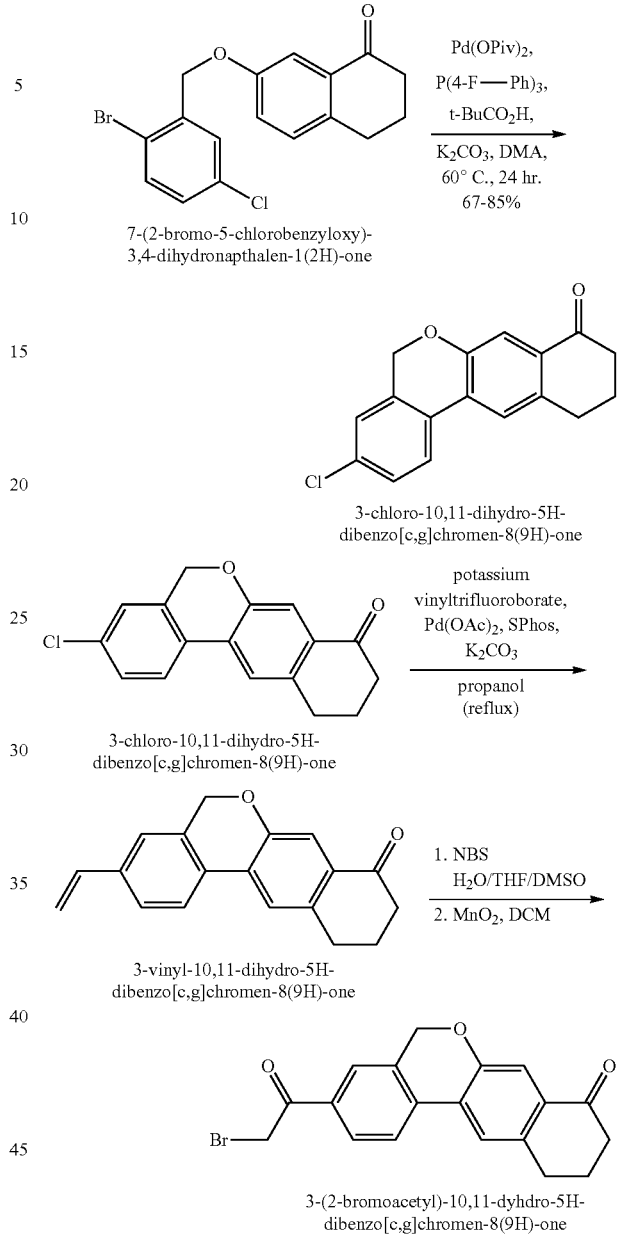

7-(2-Bromo-5-chlorobenzyloxy)-3,4-dihydronaphthalen-1(2H)-one

To a stirred solution of 7-hydroxy-1-tetralone (13.9 g, 85.7 mmol) and 1-bromo-2-(bromomethyl)-4-chlorobenzene (25.6 g, 90.0 mmol) in dimethylformamide (850 mL) was added potassium carbonate (24 g, 172 mmol). The reaction was stirred under argon for 18 hours then diluted with ethyl acetate (1 L). The organics were washed three times with water and once with brine. The organic layer was then dried with magnesium sulfate, filtered and concentrated. To the resulting oil was added methanol (500 mL) and the suspension was agitated for thirty minutes. 7-(2-bromo-5-chlorobenzyloxy)-3,4-dihydronaphthalen-1(2H)-one (27.8 g, 89% yield) was isolated by filtration.

3-Chloro-10,11-dihydro-5H-dibenzo[c,g]chromen-8 (9H)-one

To a 1 L flask containing palladium(II) pivalate (1.18 g, 3.8 mmol), tri(4-fluorophenyl)phosphine (1.20 g, 3.8 mmol), pivalic acid (2.33 g, 22.8 mmol) and potassium carbonate (31.8 g, 228 mmol) was added a solution of 7-(2-bromo-5-chlorobenzyloxy)-3,4-dihydronaphthalen-1(2H)-one (27.8 g, 76.2 mmol) in dimethyacetamide (380 mL). The flask was evacuated and backfilled with argon 5 times and then stirred under argon at 60° C. for 24 hours. The reaction was cooled to room temperature and diluted with MTBE and water. The resulting biphasic mixture was stirred for 3 hours and filtered through Celite, rinsing with MTBE. The organic layer of the filtrate was separated and then washed twice with water and once with brine. The organics were then dried with magnesium sulfate, filtered, concentrated and purified by flash column chromatography (Hexanes/DCM) to yield 3-chloro-10,11-dihydro-5H-dibenzo[c,g]chromen-8(9H)-one (14.4 g, 67% yield) as an off-white solid.

3-Vinyl-10,11-dihydro-5H-dibenzo[c,g]chromen-8 (9H)-one

A 3-neck oven-dried 500 mL round-bottom flask was cooled under Ar, then charged with 3-Chloro-10,11-dihydro-5H-dibenzo[c,g]chromen-8(9H)-one (12.0 g, 42.1 mmol), potassium vinyltrifluoroborate (8.47 g, 6.32 mmol), Pd(OAc)$_2$ (473 mg, 2.11 mmol), SPhos (1.74 g, 4.25 mmol), K$_2$CO$_3$ (17.5 g, 126 mmol) and anhydrous propanol (120 mL). The reaction mixture was sparged with Ar for 16 min, then heated to reflux for 5.5 h. Upon completion, the reaction mixture was cooled to RT and concentrated under reduced pressure. The crude residue was suspended in DCM, then washed with H$_2$O and brine. The organic solution was dried over MgSO$_4$, filtered and concentrated under reduced pressure. The resulting residue was further purified via silica plug, eluting with DCM to afford 3-vinyl-10,11-dihydro-5H-dibenzo[c,g]chromen-8(9H)-one (10.2 g, 87%).

3-(2-Bromoacetyl)-10,11-dihydro-5H-dibenzo[c,g]chromen-8(9H)-one

3-Vinyl-10,11-dihydro-5H-dibenzo[c,g]chromen-8(9H)-one (9.98 g, 36.1 mmol) was dissolved in a stirred solution of THF (70 mL), DMSO (70 mL) and H$_2$O (35 mL). NBS (6.75 g, 37.9 mmol) was added in a single portion and the reaction mixture was stirred at RT for 33 min. Upon completion, the reaction medium was diluted with EtOAc and washed twice with H$_2$O and once with brine. The organic phase was dried over MgSO$_4$, filtered and concentrated under reduced pressure. The resulting crude bromohydrin was suspended in DCM (200 mL) and treated with activated MnO$_2$ (62.7 g, 722 mmol). After stirring for 15 h at RT, the reaction mixture was filtered over celite and the filter cake was rinsed several times with DCM. The combined filtrate (~400 mL) was treated with MeOH (~100 mL) and the mixture was gradually concentrated under reduced pressure, causing solid material to precipitate from solution. When the liquid volume reached ~200 mL, the solid was filtered off and rinsed with MeOH. The concentration/precipitation/filtration/rinsing sequence was performed 2× more, resulting in the collection of 3 crops of powdered 3-(2-bromoacetyl)-10,11-dihydro-5H-dibenzo[c,g]chromen-8(9H)-one (7.49 g, 56% over 2 steps).

Intermediate 2

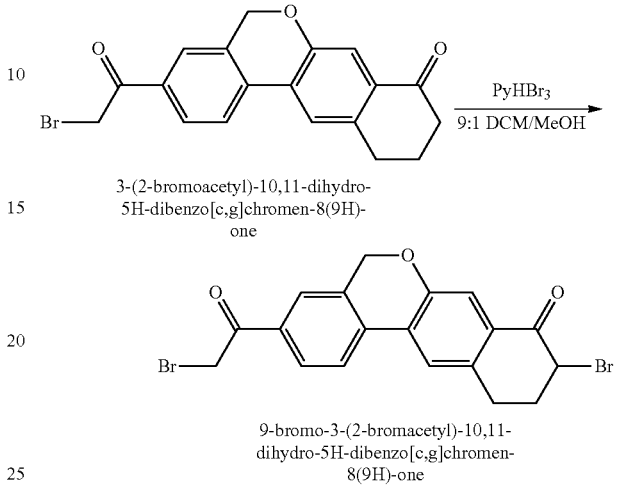

3-(2-bromoacetyl)-10,11-dihydro-5H-dibenzo[c,g]chromen-8(9H)-one 9-bromo-3-(2-bromacetyl)-10,11-dihydro-5H-dibenzo[c,g]chromen-8(9H)-one

9-Bromo-3-(2-bromoacetyl)-10,11-dihydro-5H-dibenzo[c,g]chromen-8(9H)-one

A mixture of 3-(2-bromoacetyl)-10,11-dihydro-5H-dibenzo[c,g]chromen-8(9H)-one (2.58 g, 6.95 mmol), pyridinium tribromide (2.56 g, 8.0 mmol), dichloromethane (22 mL) and methanol (2.5 mL) was stirred at about 20° C. for 3 hours to obtain a slurry. The precipitated product was filtered, washed with dichloromethane (10 mL) and dried in a vacuum oven at 40° C. to give 9-bromo-3-(2-bromoacetyl)-10,11-dihydro-5H-dibenzo[c,g]chromen-8(9H)-one (2.62 g, 84% yield). 400 MHz $^1$H NMR (CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Intermediate 2a

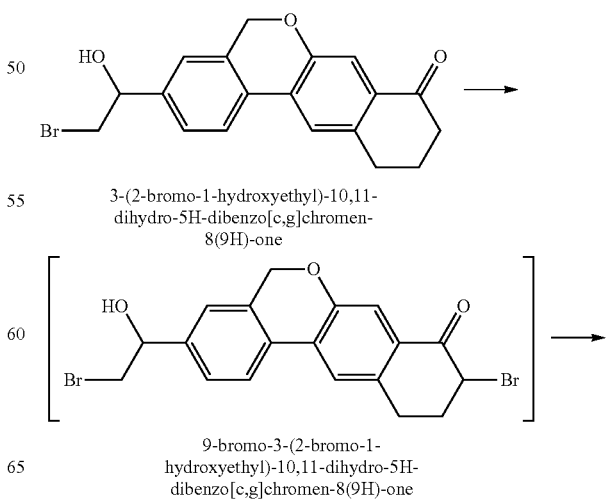

3-(2-bromo-1-hydroxyethyl)-10,11-dihydro-5H-dibenzo[c,g]chromen-8(9H)-one 9-bromo-3-(2-bromo-1-hydroxyethyl)-10,11-dihydro-5H-dibenzo[c,g]chromen-8(9H)-one

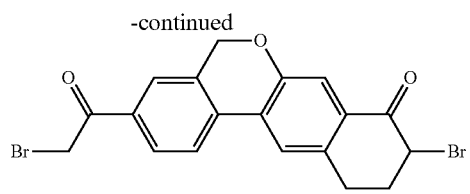

9-bromo-3-(2-bromoacetyl)-10,11-
dihydro-5H-dibenzo[c,g]chromen-
8(9H)-one

9-Bromo-3-(2-bromoacetyl)-10,11-dihydro-5H-dibenzo[c,g]chromen-8(9H)-one

To 3-(2-bromo-1-hydroxyethyl)-10,11-dihydro-5H-dibenzo[c,g]chromen-8(9H)-one (20.3 g, 54.4 mmol) in DCM (365 mL) was added MeOH (22 mL) and pyridinium tribromide (18.24 g, 57.0 mmol). After 2 h, water was added (100 mL) and after briefly agitating the layers split and the bottom organic layer was collected. The organic layer was then washed with 1M HCl (100 mL) and the bottom organic layer containing 9-bromo-3-(2-bromo-1-hydroxyethyl)-10,11-dihydro-5H-dibenzo[c,g]chromen-8(9H)-one was collected. 400 MHz $^1$H NMR (CDCl$_3$) 7.75 (d, J=8.1 Hz, 1H), 7.68 (s, 1H), 7.61 (s, 1H), 7.42 (d, J=7.5 Hz, 1H), 7.24 (s, 1H), 5.13 (s, 2H), 4.99-4.96 (m, 1H), 4.73 (dd, J=4.1, 4.1 Hz, 1H), 3.69-3.66 (m, 1H), 3.58-3.53 (m, 1H), 3.35-3.27 (m, 1H), 2.96-2.90 (m, 1H), 2.58-2.44 (m, 2H), C—OH not observed.

To 9-bromo-3-(2-bromo-1-hydroxyethyl)-10,11-dihydro-5H-dibenzo[c,g]chromen-8(9H)-one (approx. 54.4 mmol) in DCM (365 mL) was added sodium bicarbonate (5.45 g), sodium bromide (6.14 g), TEMPO (16.55 mg) and water (60 mL). The solution was cooled between 0-5° C. and 6% bleach (91.5 mL) was added. After 1 h isopropyl alcohol (20 mL) was added and the reaction mixture was warmed to room temperature. Agitation was stopped, the layers separated and the lower organic layer was collected and concentrated removing approximately 345 g of solvent. The slurry was filtered and the cake washed with 50 mL water and then 50 mL DCM (pre-cooled to 5° C.). The solids were collected and dried under vacuum to obtain 9-bromo-3-(2-bromoacetyl)-10,11-dihydro-5H-dibenzo[c,g]chromen-8(9H)-one (18.6 g, 76% yield). 400 MHz $^1$H NMR (CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H); 100 MHz $^{13}$C NMR (CDCl$_3$) δ 190.4, 189.6, 154.2, 136.6, 134.1, 133.9, 132.9, 131.8, 129.3, 127.2, 125.6, 124.2, 123.3, 117.0, 68.1, 49.9, 31.8, 30.4, 25.5.

Intermediate 2b

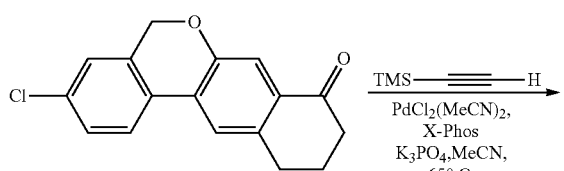

3-chloro-10,11-dihydro-5H-
dibenzo[c,g]chromen-8(9H)-one

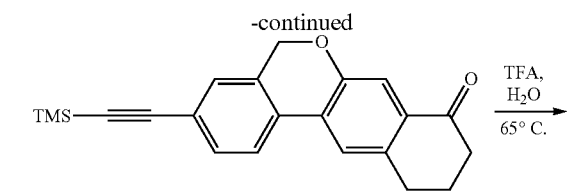

3-((trimethylsilyl)ethynyl)-10,11-dihydro-
5H-dibenzo[c,g]chromen-8(9H)-one

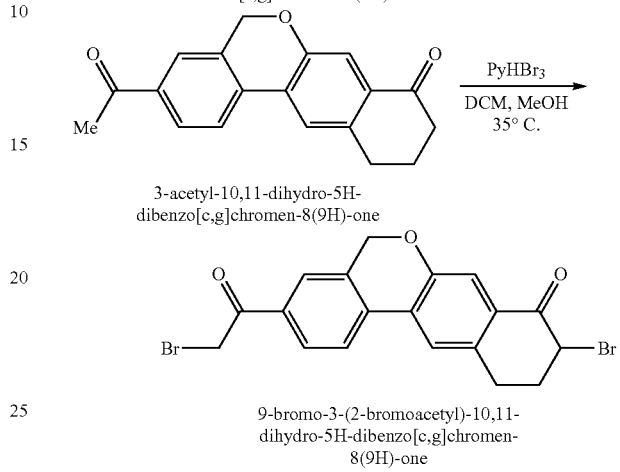

3-acetyl-10,11-dihydro-5H-
dibenzo[c,g]chromen-8(9H)-one 9-bromo-3-(2-bromoacetyl)-10,11-
dihydro-5H-dibenzo[c,g]chromen-
8(9H)-one

3-((Trimethylsilyl)ethynyl)-10,11-dihydro-5H-dibenzo[c,g]chromen-8(9H)-one

A 300 mL flask equipped with an overhead stirrer and a reflux condenser under an atmosphere of nitrogen was charged with 3-chloro-10,11-dihydro-5H-dibenzo[c,g]chromen-8(9H)-one (10.0 g, 35.12 mmol), powdered anhydrous tripotassium phosphate (22.4 g, 105.4 mmol), XPhos (1.34 g, 2.81 mmol), and PdCl$_2$(MeCN)$_2$ (364 mg, 1.40 mmol). Acetonitrile (140 mL) was added followed by TMSacetylene (18 mL, 141 mmol). The mixture was heated to 65° C. After 6 h, the reaction was judged complete, and the mixture was cooled to 20° C. The mixture was filtered through a fritted funnel, and the filtercake was washed with acetonitrile. The filtrate was concentrated to about 150 mL under reduced pressure and extracted with heptane (50 mL, 3×100 mL). N-Acetyl cysteine (15 g) was added to the acetonitrile phase, and the mixture was agitated for 5 h at 45° C. The mixture was cooled to ambient temperature, filtered through a fritted funnel, and the filtercake was washed with acetonitrile. The filtrate was concentrated to about 120 mL under reduced pressure. Water (120 mL) was added and the mixture was agitated for 40 minutes at 45° C. and then cooled to ambient temperature. After 30 minutes the mixture was filtered through a fritted funnel to provide 3-((trimethylsilyl)ethynyl)-10,11-dihydro-5H-dibenzo[c,g]chromen-8(9H)-one (4.07 g, 33.4% yield) as a yellow solid: 400 MHz $^1$H NMR (CDCl$_3$) δ 7.65 (d, J=8.1 Hz, 1H), 7.60 (s, 1H), 7.55 (s, 1H), 7.47 (dd, J=8.1, 1.4 Hz, 1H), 7.27 (s, 1H), 5.06 (s, 2H), 2.95 (t, J=6.1 Hz, 2H), 2.67-2.59 (m, 2H), 2.18-2.08 (m, 2H), 0.26 (s, 9H).

3-Acetyl-10,11-dihydro-5H-dibenzo[c,g]chromen-8(9H)-one

A 20 mL vial with stirbar was charged with 3-((trimethylsilyl)ethynyl)-10,11-dihydro-5H-dibenzo[c,g]chromen-8

(9H)-one (850 mg, 2.44 mmol) and formic acid (9.8 mL). The solution was heated to 65° C. After 3 h, the reaction was judged complete. The mixture was concentrated under reduced pressure; the resulting residue was taken up in CH$_2$Cl$_2$ and loaded onto a prepacked 25 g silica gel cartridge. The product was purified by chromatography on a prepacked 80 g silica gel column eluting with a solvent gradient from 5% to 85% EtOAc/hexanes. The product containing fractions were combined and concentrated to provide 3-acetyl-10,11-dihydro-5H-dibenzo[c,g]chromen-8(9H)-one (616 mg, 86%): 400 MHz $^1$H NMR (CDCl$_3$) δ 8.00-7.94 (m, 1H), 7.81 (d, J=8.2 Hz, 1H), 7.77 (s, 1H), 7.64 (s, 2H), 5.16 (s, 2H), 2.98 (t, J=6.1 Hz, 2H), 2.69-2.64 (m, 2H), 2.63 (s, 3H), 2.21-2.09 (m, 2H).

9-Bromo-3-(2-bromoacetyl)-10,11-dihydro-5H-dibenzo[c,g]chromen-8(9H)-one

A 20 mL vial with a stirbar was charged with 3-acetyl-10, 11-dihydro-5H-dibenzo[c,g]chromen-8(9H)-one (100 mg, 0.366 mmol), 9:1 CH$_2$Cl$_2$/MeOH (3.4 mL) and pyridinium tribromide (246 mg, 0.769 mmol). The solution was heated to 35° C. After 30 minutes, the reaction was judged complete. The mixture was cooled to ambient temperature, diluted with EtOAc (50 mL) and sequentially washed with saturated aqueous Na$_2$S$_2$O$_3$ (20 mL), 2% aqueous NaHCO$_3$ (20 mL), water (20 mL), and brine (10 mL). The organic phase was dried over MgSO$_4$, filtered and concentrated under reduced pressure resulting in 9-bromo-3-(2-bromoacetyl)-10,11-dihydro-5H-dibenzo[c,g]chromen-8(9H)-one (68 mg, 41%): 400 MHz $^1$H NMR (CDCl$_3$) δ 8.03-8.01 (m, 1H), 7.85 (d, J=8.2 Hz, 1H), 7.82 (s, 1H), 7.71 (s, 1H), 7.67 (s, 1H), 5.19 (s, 2H), 4.74 (dd, J=4.1, 4.1 Hz, 1H), 4.45 (s, 2H), 3.37-3.29 (m, 1H), 2.99-2.92 (m, 1H), 2.59-2.46 (m, 2H).

Intermediate 3

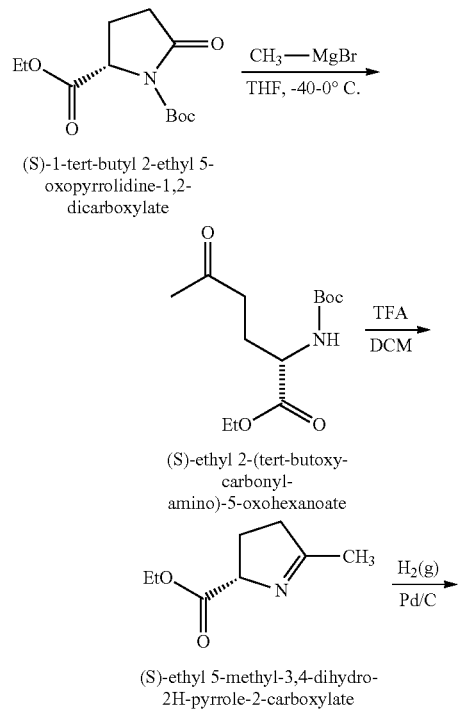

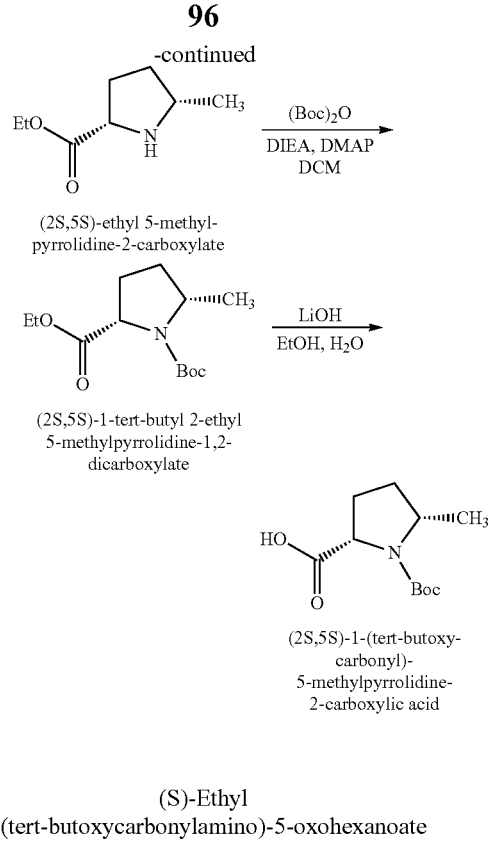

(S)-Ethyl 2-(tert-butoxycarbonylamino)-5-oxohexanoate

A solution of ethyl N-Boc (S)-pyroglutamate (20.0 g, 77.7 mmol) was in anhydrous THF (150 mL) in a two neck round bottom under argon was cooled to −40° C. Methylmagnesium bromide solution (3.0 M in Ether, 28.5 mL, 85.5 mmol) was added to the reaction mixture dropwise over 30 minutes. The reaction was stirred for 4 hrs at −40° C. then for 1 hr at 0° C. The reaction was partitioned between ethyl acetate and saturated ammonium chloride solution and acidified with 1 N HCl. The aqueous layer was extracted two more times with ethylacetate. The organic layers were combined and dried with sodium sulfate. The crude material was purified by column chromatography (20%-40% EtOAc/hexanes) to yield (S)-ethyl 2-(tert-butoxycarbonylamino)-5-oxohexanoate as a viscous oil and was used directly in the following step.

(S)-Ethyl 5-methyl-3,4-dihydro-2H-pyrrole-2-carboxylate (S)-ethyl 2-(tert-butoxycarbonylamino)-5-oxohexanoate in a 1 L flask was treated with a trifluoro acetic acid/dichloromethane solution (1:1 mixture, 100 mL). Effervescence was observed and the mixture was allowed to stir for 4 hours at room temperature. After which time the volatiles were removed in vacuo to yield (S)-ethyl 5-methyl-3,4-dihydro-2H-pyrrole-2-carboxylate as an oil, and used directly in the following step.

(2S,5S)-Ethyl 5-methylpyrrolidine-2-carboxylate

The crude imine 3 in a 1 L flask was dissolved with ethanol (400 mL) was evacuated and charged with argon three times (3×). Palladium on carbon (apprx. 750 mg, 10% w/w, dry) was added and the reaction was evacuated of gas and charged with hydrogen gas (3×). The reaction was allowed to stir under atmospheric hydrogen for 16 hours. The mixture was filtered through a plug of celite and the filtrate was concentrated in vacuo. Diethyl ether was added to the oil and a precipitate formed. The mixture was filtered to yield (2S,5S)-ethyl 5-methylpyrrolidine-2-carboxylate, as a white solid (10.6 g, 67.4 mmol, 86.7% over three steps). $^1$H NMR (400 MHz, cdcl$_3$) δ 4.48 (dd, 1H), 4.27 (q, 2H), 3.92-3.80 (m, 1H), 2.52-2.36 (m, 1H), 2.32-2.13 (m, 2H), 1.75-1.60 (m, 1H), 1.51 (d, 3H), 1.30 (t, 3H).

(2S,5S)-1-Tert-butyl 2-ethyl 5-methylpyrrolidine-1,2-dicarboxylate

To a solution of (2S,5S)-ethyl 5-methylpyrrolidine-2-carboxylate (7.0 g, 44.5 mmol) in dichloromethane (250 mL), ditertbutylanhydride (10.7 g, 49.0 mmol), diisopropylethylamine (17.1 mL, 98.0 mmol) dropwise over 10 minutes, and dimethyl amino pyridine (0.27 g, 2.23 mmol) were added successively. Effervescence was observed and the mixture was allowed to stir for 16 hours at room temperature. The reaction was washed with HCl (250 mL, of 1N). The organic layer was then dried with sodium sulfate. The crude material was purified by column chromatography (5%-25% EtOAc/hexanes) to yield (2S,5S)-1-tert-butyl 2-ethyl 5-methylpyrrolidine-1,2-dicarboxylate as an oil (6.46 g, 25.1 mmol, 56%). LCMS-ESI$^+$: calc'd for C$_{13}$H$_{23}$NO$_4$: 257.16 (M$^+$). Found: 258.70 (M+H$^+$).

(2S,5S)-1-(Tert-butoxycarbonyl)-5-methylpyrrolidine-2-carboxylic acid

To a solution of (2S,5S)-1-tert-butyl 2-ethyl 5-methylpyrrolidine-1,2-dicarboxylate (6.46 g, 25.1 mmol) in ethanol (20 mL) was added lithium hydroxide mono hydrate (2.11 g, 50.2 mmol) and deionized water (12 mL). The mixture was allowed to stir for 16 hours then partitioned between ethylacetate and a 1:1 mixture of saturated brine and 1N HCl. The aqueous layer was extracted an additional time with ethyl acetate. The organic layers were combined, dried with sodium sulfate and the solvent was removed in vacuo to yield (2S,5S)-1-(tert-butoxycarbonyl)-5-methylpyrrolidine-2-carboxylic acid as a white solid (quant.) and was used directly in the following step.

Intermediate 4

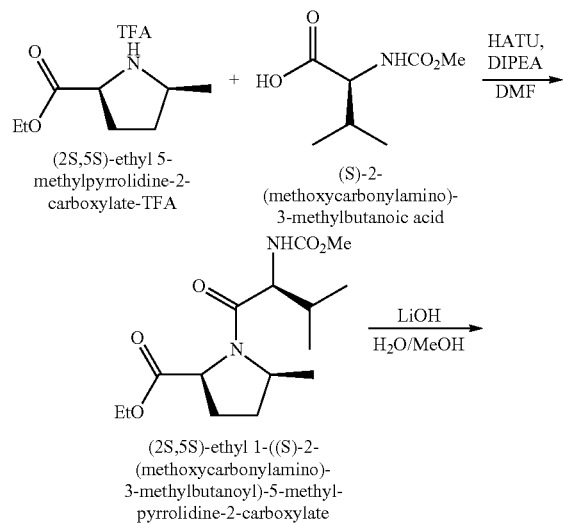

(2S,5S)-Ethyl 1-((S)-2-(methoxycarbonylamino)-3-methylbutanoyl)-5-methylpyrrolidine-2-carboxylate (2S,5S)-Ethyl 5-methylpyrrolidine-2-carboxylate-TFA (10.0 g, 39.3 mmol), (S)-2-(methoxycarbonylamino)-3-methylbutanoic acid (6.88 g, 39.3 mmol) and HATU (14.9 g, 39.3 mmol) were combined in DMF (100 mL) and DIPEA (15.0 mL, 86.5 mmol) was added. After stirring for 1 h at RT, the reaction mixture was diluted with EtOAc. The organic phase was washed successively with 10% HCl, saturated aqueous NaHCO$_3$ and brine, then dried over MgSO$_4$, filtered and concentrated under reduced pressure to afford (2S,5S)-ethyl 1-((S)-2-(methoxycarbonylamino)-3-methylbutanoyl)-5-methylpyrrolidine-2-carboxylate. The crude material was carried on without further purification.

(2S,5S)-1-(S)-2-(Methoxycarbonylamino)-3-methylbutanoyl)-5-methylpyrrolidine-2-carboxylic acid (2S,5S)-Ethyl 1-((S)-2-(methoxycarbonylamino)-3-methylbutanoyl)-5-methylpyrrolidine-2-carboxylate (39.3 mmol, assuming complete conversion from the previous transformation) was suspended in MeOH (200 mL) and aqueous LiOH (1.0 M, 100 mL, 100 mmol) was added. The reaction mixture was stirred o/n, then concentrated under reduced pressure to remove most of the MeOH. The aqueous solution was washed 2× with DCM before being acidified to pH∼1-2 with 10% HCl. The acidic aqueous phase was then extracted 5× with EtOAc. The combined EtOAc extracts were dried over MgSO$_4$ filtered and concentrated under reduced pressure to afford (2S,5S)-1-(S)-2-(Methoxycarbonylamino)-3-methylbutanoyl)-5-methylpyrrolidine-2-carboxylic acid (6.89 g, 56% over 2 steps).

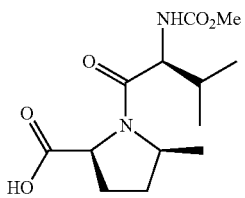

(2S,5S)-1-((S)-2-(methoxycarbonylamino)-3-methylbutanoyl)-5-methyl-pyrrolidine-2-carboxylic acid Intermediate 5

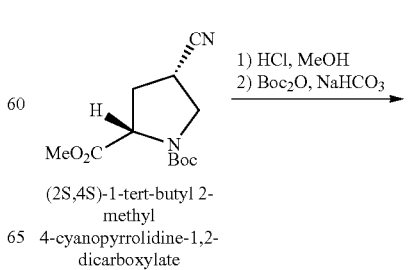

(2S,4S)-1-tert-butyl 2-methyl 4-cyanopyrrolidine-1,2-dicarboxylate

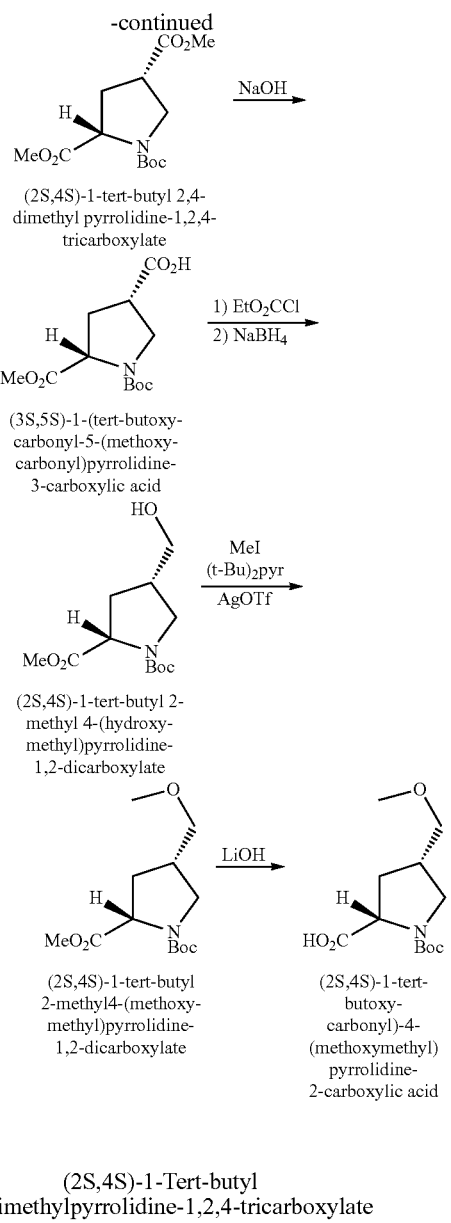

(2S,4S)-1-Tert-butyl
2,4-dimethylpyrrolidine-1,2,4-tricarboxylate

To a solution of (2S,4S)-1-tert-butyl 2-methyl 4-cyanopyrrolidine-1,2-dicarboxylate (9.0 g, 35.4 mmol) in MeOH (196 mL) was added HCl (4M in 1,4-dioxane, 100 mL, 403 mmol). The solution was stirred at room temperature for 16 h and concentrated in vacuo. The crude intermediate was dissolved in EtOAc (180 mL) and basified with aqueous bicarbonate (sat.). Di-tert-butyl dicarbonate (8.5 g, 38.9 mmol) was added and the biphasic solution was stirred at room temperature for 12 h. The layers were then separated and the aqueous layer was back extracted with EtOAc. The combined organic layers were washed with brine, dried over Na₂SO₄, and concentrated. The crude oil was purified by silica gel chromatography (15% to 40% to 100% EtOAc/Hexanes) to provide (2S,4S)-1-tert-butyl 2,4-dimethyl pyrrolidine-1,2,4-tricarboxylate (9.56 g, 94%).

(3S,5S)-1-(Tert-butoxycarbonyl)-5-(methoxycarbonyl)pyrrolidine-3-carboxylic acid To a solution of (2S,4S)-1-tert-butyl 2,4-dimethylpyrrolidine-1,2,4-tricarboxylate (9.56 g, 33.3 mmol) in THF (70 mL) at 0° C. (external temperature, ice bath) was added NaOH (1N aqueous, 33 mL, 33.3 mmol) dropwise over 15 min. The solution was stirred at 0° C. for 5 h before acidification with HCl (1N). The solution was extracted with EtOAc (3×). The combined organic layers were dried over Na₂SO₄ and concentrated. The crude oil was purified by silica gel chromatography (2% to 5% to 10% MeOH/CH₂Cl₂) to provide (3S,5S)-1-(tert-butoxycarbonyl)-5-(methoxycarbonyl)pyrrolidine-3-carboxylic acid (6.38 g, 70%).

(2S,4S)-1-Tert-butyl 2-methyl 4-(hydroxymethyl)pyrrolidine-1,2-dicarboxylate

To a solution of (3S,5S)-1-(tert-butoxycarbonyl)-5-(methoxycarbonyl)pyrrolidine-3-carboxylic acid (6.38 g, 23.3 mmol) in THF (116 mL) at 0° C. (external temperature, ice bath) was added Et₃N (4.9 mL, 35.0 mmol) and ethyl chloroformate (2.7 mL, 28.0 mmol). The resulting solution was stirred at 0° C. for 45 min, during which time a white precipitate forms. The reaction mixture was filtered through celite and concentrated.

The crude intermediate was dissolved in THF (59 mL) and cooled to 0° C. (external temperature, ice bath). NaBH₄ (4.41 g, 116.7 mmol) in H₂O (59 mL) was slowly added and the resulting solution was stirred at 0° C. for 2 h. The reaction mixture was diluted with EtOAc and washed with H₂O. The aqueous layer was back extracted with EtOAc. The combined organic layers were dried over Na₂SO₄ and concentrated. The crude oil was purified by silica gel chromatography (42% to 69% to 100% EtOAc/Hexanes) to provide (2S,4S)-1-tert-butyl 2-methyl 4-(hydroxymethyl)pyrrolidine-1,2-dicarboxylate (3.63 g, 60%).

(2S,4S)-1-Tert-butyl 2-methyl 4-(methoxymethyl)pyrrolidine-1,2-dicarboxylate

To a solution of (2S,4S)-1-tert-butyl 2-methyl 4-(hydroxymethyl)pyrrolidine-1,2-dicarboxylate (2.57 g, 9.9 mmol) in CH₂Cl₂ (50 mL) was added AgOTf (4.07 g, 15.8 mmol) and 2,6-di-tert-butylpyridine (4.4 mL, 19.8 mmol). The reaction mixture was cooled to 0° C. (external temperature, ice bath) and MeI (0.98 mL, 15.8 mmol) was slowly added. The resulting slurry was stirred at 0° C. for 1.5 h and at room temperature for 1.5 h. The slurry was diluted with CH₂Cl₂ and filtered through celite. The filtrate was concentrated to dryness, dissolved in Et₂O, and washed with HCl (1N) and brine. The aqueous layers were backextracted with Et₂O and the combined organic layers were dried over Na₂SO₄ and concentrated. The crude oil was purified by silica gel chromatography (10% to 75% to 100% EtOAc/Hexanes) to provide (2S,4S)-1-tert-butyl 2-methyl 4-(methoxymethyl)pyrrolidine-1,2-dicarboxylate (2.11 g, 78%). 1H-NMR: 400 MHz, (CDCl₃) δ: (mixture of rotomers, major reported) 4.20 (t, 1H), 3.71 (s, 3H), 3.67 (m, 1H), 3.34 (m, 2H), 3.30 (s, 3H), 3.16 (t, 1H), 2.43 (m, 2H), 1.74 (m, 1H), 1.38 (s, 9H).

(2S,4S)-1-(Tert-butoxycarbonyl)-4-(methoxymethyl)pyrrolidine-2-carboxylic acid

To a solution of (2S,4S)-1-tert-butyl 2-methyl 4-(methoxymethyl)pyrrolidine-1,2-dicarboxylate (2.11 g, 7.7 mmol) in a mixture of THF (38 mL) and MeOH (15 mL) was added LiOH (2.5 M aqueous, 15 mL, 38.6 mmol). The resulting solution was stirred at room temperature for 2 h, and acidified with aqueous HCl (1N). The desired product was extracted with CH₂Cl₂ (4×). The combined organic layers were dried over Na₂SO₄ and concentrated to provide (2S,4S)-1-(tert-butoxycarbonyl)-4-(methoxymethyl)pyrrolidine-2-carboxylic acid (2.0 g, 99%). 1H-NMR: 400 MHz, (CDCl₃) δ: (mixture of rotamers, major reported) 4.33 (t, 1H), 3.65 (m, 1H), 3.35 (m, 2H), 3.32 (s, 3H), 3.16 (t, 1H), 2.45 (m, 2H), 2.12 (m, 1H), 1.46 (s, 9H).

Intermediate 6

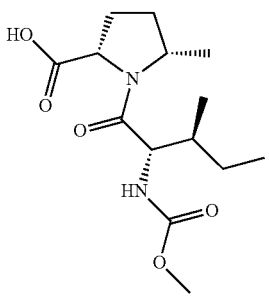

(2S,5S)-1-((2S,3S)-2-(methoxycarbonylamino)-3-methylpentanoyl)-5 methylpyrroli dine-2-carboxylic acid (2S,5S)-1-((2S,3S)-2-(Methoxycarbonylamino)-3-methylpentanoyl)-5 methylpyrrolidine-2-carboxylic acid (2S,5S)-1-((2S,3S)-2-(methoxycarbonylamino)-3-methylpentanoyl)-5 methylpyrrolidine-2-carboxylic acid was synthesized in a similar manner as Intermediate 4 substituting (S)-2-(methoxycarbonylamino)-3-methylbutanoic acid with (2S,3S)-2-(methoxycarbonyl-amino)-3-methylpentanoic acid MS (ESI) m/z 301.19 [M+H]⁺.

Example 7

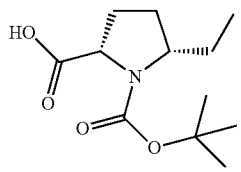

(2S,5S)-1-(tert-butoxycarbonyl)-5-ethylpyrrolidine-2-carboxylic acid (2S,5S)-1-(Tert-butoxycarbonyl)-5-ethylpyrrolidine-2-carboxylic acid (2S,5S)-1-(tert-butoxycarbonyl)-5-ethylpyrrolidine-2-carboxylic acid was synthesized in a similar manner as Intermediate 3 substituting ethylmagnesium bromide for methylmagnesium bromide. ¹HNMR (400 MHz, DMSO-d6): δ 12.37 (1H, s), 4.05-4.07 (1H, m), 3.63-3.64 (1H, m), 2.13-2.15 (1H, m), 1.63-1.90 (4H, m), 1.39 (10H, m), 0.83 (3H, t, J=7.2 Hz).

Example 8

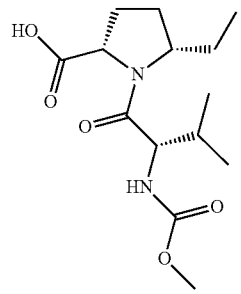

(2S,5S)-5-ethyl-1-((S)-2-(methoxycarbonyl amino)-3-methylbutanoyl)pyrrolidine-2-carboxylic acid (2S,5S)-5-Ethyl-1-((S)-2-(methoxycarbonylamino)-3-methylbutanoyl)pyrrolidine-2-carboxylic acid (2S,5S)-5-ethyl-1-((S)-2-(methoxycarbonylamino)-3-methylbutanoyl)pyrrolidine-2-carboxylic acid was synthesized in a similar manner as Example 4 substituting (2S,5S)-ethyl 5-methylpyrrolidine-2-carboxylate-TFA with (2S,5S)-methyl 5-ethylpyrrolidine-2-carboxylate-HCl. MS (ESI) m/z 301.15 [M+H]⁺.

Intermediate 9

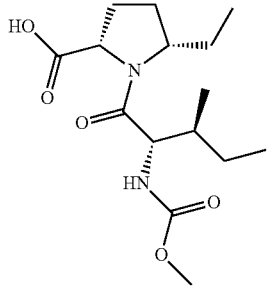

(2S,5S)-5-ethyl-1-((2S,3S)-2-(methoxycarbonylamino)-3-methylpentanoyl)pyrrolidine-2-carboxylic acid (2S,5S)-5-Ethyl-1-(2S,3S)-2-(methoxycarbonylamino)-3-methylpentanoyl)pyrrolidine-2-carboxylic acid (2S,5S)-5-ethyl-1-((2S,3S)-2-(methoxycarbonylamino)-3-methylpentanoyl)pyrrolidine-2-carboxylic acid was synthesized in a similar manner as Intermediate 4 substituting (S)-2-(methoxycarbonylamino)-3-methylbutanoic acid with (2S,3S)-2-(methoxycarbonyl-amino)-3-methylpentanoic acid and (2S,5S)-ethyl 5-methylpyrrolidine-2-carboxylate-TFA with (2S,5S)-methyl 5-ethylpyrrolidine-2-carboxylate-HCl.

Intermediate 10

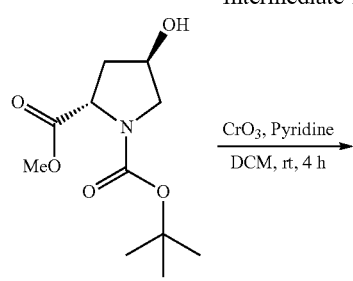

(2S,4R)-1-tert-butyl
2-methyl 4-
hydroxypyrrolidine-
1,2-dicarboxylate

CrO₃, Pyridine
DCM, rt, 4 h

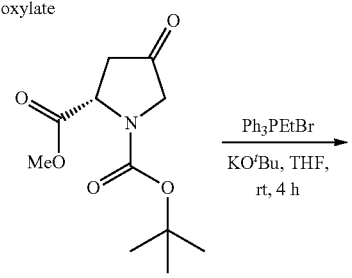

(S)-1-tert-butyl 2-methyl
4-oxopyrrolidine-1,2-
dicarboxylate

Ph₃PEtBr
KOtBu, THF,
rt, 4 h

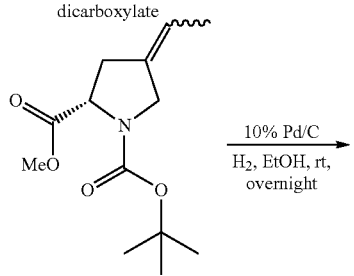

(S)-1-tert-butyl 2-methyl
4-ethylidenepyrrolidine-
1,2-dicarboxylate

10% Pd/C
H₂, EtOH, rt,
overnight

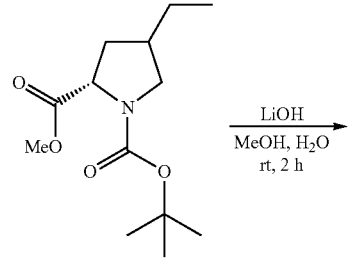

(2S)-1-tert-butyl 2-methyl
4-ethylpyrrolidine-
1,2-dicarboxylate

LiOH
MeOH, H₂O
rt, 2 h

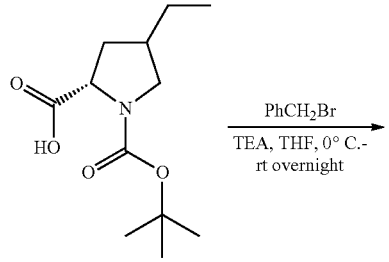

(2S)-1-(tert-butoxycarbonyl)-
4-ethylpyrrolidine-
2-carboxylic acid

PhCH₂Br
TEA, THF, 0° C.-
rt overnight

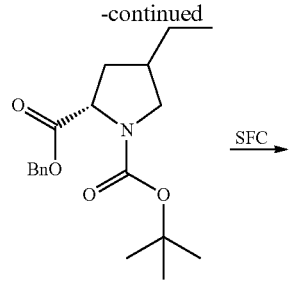

(2S)-2-benzyl 1-tert-butyl
4-ethylpyrrolidine-1,2-
dicarboxylate

SFC

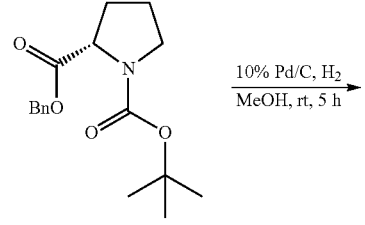

(2S,4S)-2-benzyl 1-tert-butyl
4-ethylpyrrolidine-1,2-
dicarboxylate

10% Pd/C, H₂
MeOH, rt, 5 h

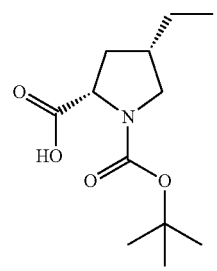

(2S,4S)-1-(tert-butoxy-
carbonyl)-
4-ethylpyrrolidine-2-
carboxylic acid

(S)-1-Tert-butyl 2-methyl 4-oxopyrrolidine-1,2-dicarboxylate

CrO₃ (194 g, 1.94 mol) was added slowly with stirring over 30 min to a solution of pyridine (340 mL) in DCM (900 mL) at 0° C. The mixture was warmed to rt and (2S,4R)-1-tert-butyl 2-methyl 4-hydroxypyrrolidine-1,2-dicarboxylate (56 g, 0.216 mol) in DCM (700 mL) was added. The reaction was stirred vigorously for 4 hs at rt. The formed dark solid was decanted and washed with DCM. The organic phases were washed with aq. NaHCO₃, 10% aqueous critic acid, and brine, and dried over anhydrous Na₂SO₄. The solvent was removed in vacuo and purified by silica gel column chromatography (PE: EtOAc=50:1 to 10:1) to afford (S)-1-tert-butyl 2-methyl 4-oxopyrrolidine-1,2-dicarboxylate (42.6 g, 81%) as yellow oil.

(S)-1-Tert-butyl 2-methyl 4-ethylidenepyrrolidine-1,2-dicarboxylate

A solution of Ph₃PEtBr (84 g, 227 mmol) and KOtBu (76.7 g, 556 mmol) in THF (1100 mL) was stirred at rt under nitrogen atmosphere for 1 h, and then added (S)-1-tert-butyl 2-methyl 4-oxopyrrolidine-1,2-dicarboxylate (50 g, 206 mmol) in THF (350 mL) dropwise. The mixture was stirred at room temperature for 4 hs. TLC showed the reaction was completed. The mixture was quenched with NH4Cl aqueous and concentrated to remove THF, and then dissolved in EtOAc and water. The combined organic layer was washed with water, brine, dried over Na2SO4, filtered and concentrated. The crude product was purified by column chromatography (PE: EtOAc=30:1 to 5:1) to afford (S)-1-tert-butyl 2-methyl 4-ethylidenepyrrolidine-1,2-dicarboxylate (18.3 g, 35%) as yellow oil.

(2S)-1-Tert-butyl 2-methyl 4-ethylpyrrolidine-1,2-dicarboxylate

A mixture of (S)-1-tert-butyl 2-methyl 4-ethylidenepyrrolidine-1,2-dicarboxylate (50 g, 196 mmol), Pd/C (5 g) in EtOH (500 mL) was hydrogenated at room temperature overnight. The mixture was filtered and concentrated to afford (2S)-1-tert-butyl 2-methyl 4-ethylpyrrolidine-1,2-dicarboxylate (9.8 g, 97%) as colorless oil.

(2S)-1-(Tert-butoxycarbonyl)-4-ethylpyrrolidine-2-carboxylic acid

A mixture of (2S)-1-tert-butyl 2-methyl 4-ethylpyrrolidine-1,2-dicarboxylate (49.5 g, 0.19 mol), LiOH (950 mL, 1M) in MeOH (1500 mL) was stirred at room temperature overnight. TLC showed the reaction was completed. The mixture was concentrated, adjusted the pH to 2 with 1N HCl. The mixture was extracted with EA, the combined organic layer was washed with brine, dried over Na$_2$SO$_4$, concentrated to afford (2S)-1-(tert-butoxycarbonyl)-4-ethylpyrrolidine-2-carboxylic acid (45.5 g, 97%) as white solid without further purification.

(2S)-2-Benzyl 1-tert-butyl 4-ethylpyrrolidine-1,2-dicarboxylate

A mixture of (2S)-1-(tert-butoxycarbonyl)-4-ethylpyrrolidine-2-carboxylic acid (45.5 g, 187 mmol), TEA (37.8 g, 374 mmol) in THF (1 L) was added dropwise BnBr (38.5 g, 225 mmol) at 0° C. The mixture was stirred at room temperature overnight. TLC showed the reaction was completed. The mixture was concentrated to remove solvent. The residue was partitioned between EtOAc and water. The combined organic layer was washed with brine, dried over Na$_2$SO$_4$ and concentrated. The crude product was purified by column chromatography to give (2S)-2-benzyl 1-tert-butyl 4-ethylpyrrolidine-1,2-dicarboxylate (46 g, 74%) as colorless oil. (2S)-2-benzyl 1-tert-butyl 4-ethylpyrrolidine-1,2-dicarboxylate was separated by preparative SFC via a Chiralcel OD 250*50 mm i.d. 10 μm column (Mobile phase: A for n-hexane and B for ethanol (0.05% IPAm), Gradient: A: B=97:3, Flow rate: 100 ml/min, Wavelength: 210 and 220 nm, Injection amount: 0.4 g per injection) to provide (2S,4S)-2-benzyl 1-tert-butyl 4-ethylpyrrolidine-1,2-dicarboxylate.

(2S,4S)-1-(Tert-butoxycarbonyl)-4-ethylpyrrolidine-2-carboxylic acid

A mixture of (2S,4S)-2-benzyl 1-tert-butyl 4-ethylpyrrolidine-1,2-dicarboxylate (18 g, 54.1 mmol), Pd/C (3.6 g) in MeOH (1 L) was hydrogenated at room temperature overnight. TLC showed that the reaction was completed. The mixture was filtered by Celite. The filtrate was concentrated to afford (2S,4S)-1-(tert-butoxycarbonyl)-4-ethylpyrrolidine-2-carboxylic acid (10 g, 77%) as white solid. $^1$H NMR: 400 MHz CDCl$_3$: δ 9.88 (br, 1H), 4.31-4.19 (m, 1H), 3.82-3.68 (m, 1H), 3.03-2.95 (m, 1H), 2.49-2.39 (m, 1H), 2.12-2.03 (m, 1H), 1.81-1.56 (m, 1H), 1.45 (d, J=8 Hz, 11H), 0.92 (t, J=6 Hz, 3H).

Intermediate 11

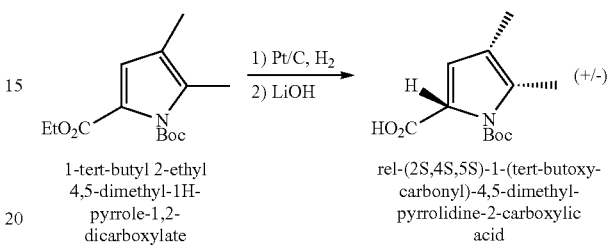

1-tert-butyl 2-ethyl 4,5-dimethyl-1H-pyrrole-1,2-dicarboxylate rel-(2S,4S,5S)-1-(tert-butoxycarbonyl)-4,5-dimethylpyrrolidine-2-carboxylic acid rel-(2S,4S,5S)-1-(tert-butoxycarbonyl)-4,5-dimethylpyrrolidine-2-carboxylic acid To a solution of 1-tert-butyl 2-ethyl 4,5-dimethyl-1H-pyrrole-1,2-dicarboxylate (4.016 g, 15.02 mmol) in EtOH (100 mL) was added Platinum on carbon (5%, 0.58 g). The slurry was stirred under an atmosphere of hydrogen (1 atm) for 3 days. The slurry was filtered through celite and washed with MeOH. The filtrate was concentrated and the crude was purified by column chromatography (SiO$_2$, 5-10-20% EtOAc/Hexanes) to provide rel-(2S,4S,5S)-1-tert-butyl 2-ethyl 4,5-dimethylpyrrolidine-1,2-dicarboxylate.

To a solution of rel-(2S,4S,5S)-1-tert-butyl 2-ethyl 4,5-dimethylpyrrolidine-1,2-dicarboxylate in a mixture of THF (70 mL), MeOH (25 mL), and H$_2$O (25 mL) was added lithium hydroxide (1.53 g, 63.7 mmol). The slurry was stirred at room temperature for 2.5 h and at 45° C. for 2 h. The solution was cooled to room temperature and HCl (aqueous, 1N, 70 mL) was added. The organics were concentrated and the resulting aqueous layer was extracted with EtOAc (3×). The combined organic layers were dried over Na$_2$SO$_4$ and concentrated to provide rel-(2S,4S,5S)-1-(tert-butoxycarbonyl)-4,5-dimethylpyrrolidine-2-carboxylic acid (3.08 g, 84%).

Intermediate 12

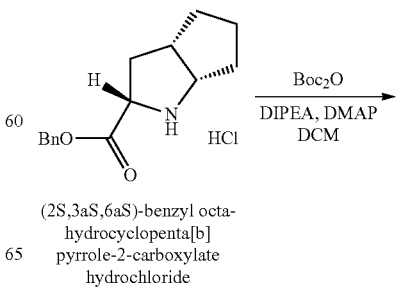

(2S,3aS,6aS)-benzyl octahydrocyclopenta[b]pyrrole-2-carboxylate hydrochloride

Intermediate 13

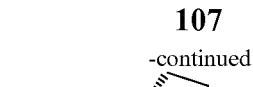
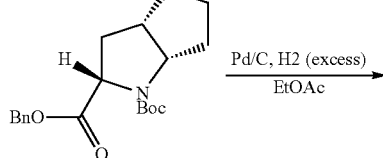

(2S,3aS,6aS)-2-benzyl 1-tert-butyl hexahydrocyclopenta[b]pyrrole-1,2(2H)-dicarboxylate

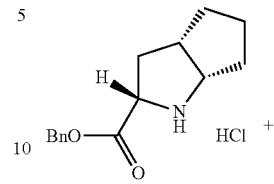

(2S,3aS,6aS)-benzyl octahydrocyclopenta[b]pyrrole-2-carboxylate hydrochloride

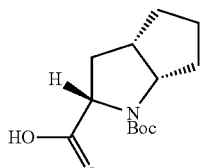

(2S,3aS,6aS)-1-tert-butoxycarbonyl)octahydrocyclopenta[b]pyrrole-2-dicarboxylic acid

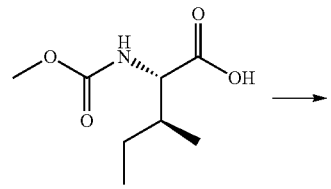

(2S,3S)-2-(methoxycarbonylamino)-3-methylpentanoic acid

(2S,3aS,6aS)-2-benzyl 1-tert-butyl hexahydrocyclopenta[b]pyrrole-1,2(2H)-dicarboxylate To a solution of commercially available (2S,3aS,6aS)-2-benzyl 1-tert-butyl hexahydrocyclopenta[b]pyrrole-1,2(2H)-dicarboxylate (4.70 g, 16.68 mmol) in methylene chloride (42 mL) was added Di-tert-butyl dicarbonate (7.28 g, 33.36 mmol) N,N-diisopropylethylamine (5.82 mL, 33.36 mmol) and 4-(Dimethylamino)pyridine (0.20 g, 1.67 mmol). The solution was stirred under air for 16 hours. Upon completion, the reaction was concentrated in vacuo, diluted in ethyl acetate, and washed with 1N HCl. The aqueous layers were backextracted twice with ethyl acetate and the combined organic layers were dried over sodium sulfate, filtered and concentrated. The resulting residue was purified by silica gel chromatrography (5-40% ethyl acetate in hexanes) to afford (2S,3aS,6aS)-2-benzyl 1-tert-butyl hexahydrocyclopenta[b]pyrrole-1,2(2H)-dicarboxylate which was used without further purification. MS (ESI) m/z 368.47 [M+Na]$^+$.

(2S,3aS,6aS)-1-(tert-butoxycarbonyl)octahydrocyclopenta[b]pyrrole-2-carboxylic acid To a 250 mL round bottom flask charged with a stirbar and (2S,3aS,6aS)-2-benzyl 1-tert-butyl hexahydrocyclopenta[b]pyrrole-1,2(2H)-dicarboxylate (5.76 g, 16.68 mmol) was added 10% Palladium on carbon (1.77 g). Ethanol was poured over the mixture and the reaction mixture was evacuated and flushed with hydrogen gas three times. The suspension was stirred at room temperature under and atmosphere of hydrogen for 24 hours. Upon completion, the reaction mixture was filtered through celite and concentrated to give (2S,3aS,6aS)-1-(tert-butoxycarbonyl)octahydrocyclopenta[b]pyrrole-2-carboxylic acid (4.45 g, >99%). MS (ESI) m/z 256.21 [M+H]$^+$.

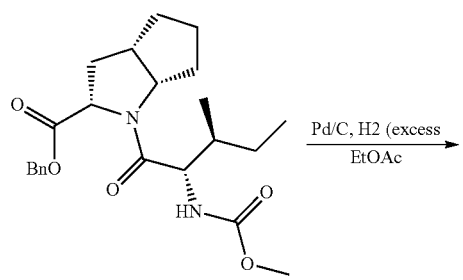

(2S,3aS,6aS)-benzyl 1-((2S,3S)-2-(methoxycarbonylamino)-3-methylpentanoyl)octahydrocyclopenta[b]pyrrole-2-carboxylate

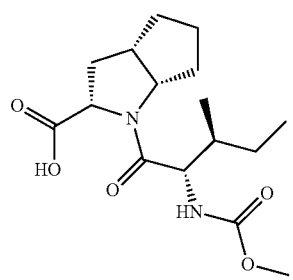

(2S,3aS,6aS)-benzyl 1-((2S,3S)-2-(methoxycarbonylamino)-3-methylpentanoyl)octahydrocyclopenta[b]pyrrole-2-carboxylic acid

(2S,3aS,6aS)-benzyl 1-((2S,3S)-2-(methoxycarbonylamino)-3-methylpentanoyl)octahydrocyclopenta[b]pyrrole-2-carboxylate To a solution of commercially available (2S,3aS,6aS)-2-benzyl 1-tert-butyl hexahydrocyclopenta[b]pyrrole-1,2(2H)- dicarboxylate (10.0 g, 35.489 mmol) in methylene chloride (100 mL) was added (2S,3S)-2-(methoxycarbonylamino)-3-methylpentanoic acid (10.072 g, 53.23 mmol), HATU (21.59 g, 56.78 mmol), and DIPEA (18.59 mL, 106.46 mmol). The reaction was stirred overnight, at which time it was concentrated in vacuo, diluted in ethyl acetate and washed with HCl (1N). The aqueous layer was backextracted with ethyl acetate, and the combined organics were dried over sodium sulphate, filtered and concentrated. The resulting oil was diluted in a small amount of chloroform and filtered to remove tetramethyl urea precipitate. The resulting oil was purified by normal phase chromatography (50% ethyl acetate in hexanes) to give (2S,3aS,6aS)-benzyl 1-((2S,3S)-2-(methoxycarbonylamino)-3-methylpentanoyl)octahydrocyclopenta[b]pyrrole-2-carboxylate (19.53 g, >99% yield) which was used without further purification. LCMS-ESI+ calc'd for C23H33N2O5: 417.23. Found: 417.37.

(2S,3aS,6aS)-1-((2S,3S)-2-(methoxycarbonylamino)-3-methylpentanoyl)octahydrocyclopenta[b]pyrrole-2-carboxylic acid To a 250 mL round bottom flask charged with a stirbar and (2S,3aS,6aS)-benzyl 1-((2S,3S)-2-(methoxycarbonylamino)-3-methylpentanoyl)octahydrocyclopenta[b]pyrrole-2-carboxylate (19.53 g crude, assumed 35.49 mmol) was added 10% Palladium on carbon (3.55 g). Ethanol was poured over the mixture and the reaction mixture was evacuated and flushed with hydrogen gas three times. The suspension was stirred at room temperature under and atmosphere of hydrogen for 3 days. Upon completion, the reaction mixture was filtered through celite and concentrated to give (2S,3aS,6aS)-1-((2S,3S)-2-(methoxycarbonylamino)-3-methylpentanoyl)octahydrocyclopenta[b]pyrrole-2-carboxylic acid (13.65 g, >99%). LCMS-ESI+ calc'd for C16H26N2O5: 327.18. Found: 327.13.

Intermediate 14

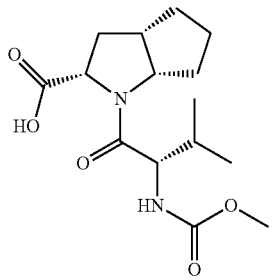

(2S,3aS,6aS)-1-((S)-2-(methoxycarbonylamino)-3-methylbutanoyl)octahydrocyclopenta[b]pyrrole-2-carboxylic acid (2S,3aS,6aS)-1-((S)-2-(methoxycarbonylamino)-3-methylbutanoyl)octahydrocyclopenta[b]pyrrole-2-carboxylic acid was synthesized in a similar manner as (2S,3aS,6aS)-1-((2S,3S)-2-(methoxycarbonylamino)-3-methylpentanoyl)octahydrocyclopenta[b]pyrrole-2-carboxylic acid substituting (2S,3S)-2-(methoxycarbonylamino)-3-methylpentanoic acid with (S)-2-(methoxycarbonylamino)-3-methylbutanoic acid. LCMS-ESI+ calc'd for C15H25N2O5: 313.17. Found: 313.12.

Intermediate 15

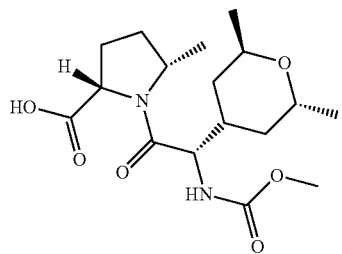

(2S,5S)-1-((S)-2-((2R,6R)-2,6-dimethyltetrahydro-2H-pyran-4-yl)-2-(methoxycarbonylamino)acetyl)-5-methylpyrrolidine-2-carboxylic acid (2S,5S)-1-((S)-2-((2R,6R)-2,6-dimethyltetrahydro-2H-pyran-4-yl)-2-(methoxycarbonylamino)acetyl)-5-methylpyrrolidine-2-carboxylic acid (2S,5S)-1-(S)-2-((2R,6R)-2,6-dimethyltetrahydro-2H-pyran-4-yl)-2-(methoxycarbonylamino)acetyl)-5-methylpyrrolidine-2-carboxylic acid was synthesized in a similar manner as Intermediate 4 substituting (S)-2-(methoxycarbonylamino)-3-methylbutanoic acid with (S)-2-((2R,6R)-2,6-dimethyltetrahydro-2H-pyran-4-yl)-2-(methoxycarbonylamino)acetic acid. 1H NMR (400 MHz, Chloroform-d) δ 5.33-5.16 (m, 1H), 4.70-4.59 (m, 1H), 4.54 (t, 1H), 4.34-4.19 (m, 2H), 4.12 (q, 1H), 3.78-3.70 (m, 1H), 3.67 (s, 3H), 2.37-2.17 (m, 3H), 2.15-2.07 (m, 1H), 2.04 (s, 1H), 1.84-1.73 (m, 1H), 1.82-1.43 (m, 3H), 1.32 (d, 3H), 1.26 (d, 4H), 1.11 (d, 3H), 0.96 (q, 1H). LCMS-ESI+ calc'd for C17H29N2O6: 357.19. Found: 357.08.

Example AA

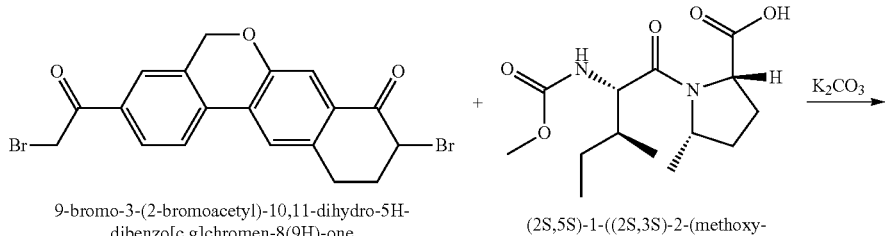

9-bromo-3-(2-bromoacetyl)-10,11-dihydro-5H-dibenzo[c,g]chromen-8(9H)-one (2S,5S)-1-((2S,3S)-2-(methoxycarbonylamino)-3-methylpentanoyl)-5-methylpyrrolidine-2-carboxylic acid

K2CO3 →

-continued

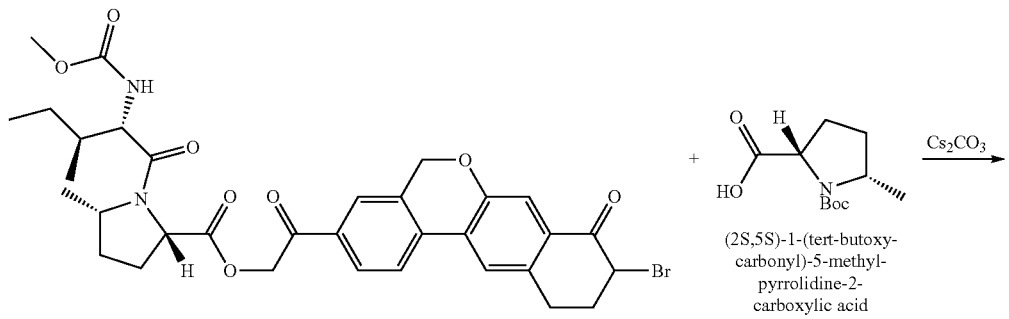

(2S,5S)-2-(9-bromo-8-oxo-8,9,10,11-tetrahydro-5H-dibenzo[c,g]chromen-3-yl)-2-oxoethyl 1-((2S,3S)-2-(methoxycarbonylamino)-3-methylpentanoyl)-5-methylpyrrolidine-2-carboxylate (2S,5S)-1-(tert-butoxycarbonyl)-5-methylpyrrolidine-2-carboxylic acid

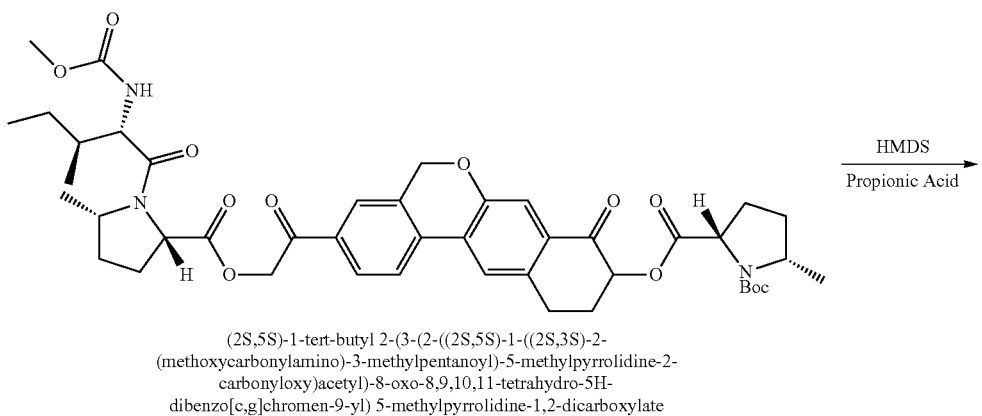

(2S,5S)-1-tert-butyl 2-(3-(2-((2S,5S)-1-((2S,3S)-2-(methoxycarbonylamino)-3-methylpentanoyl)-5-methylpyrrolidine-2-carbonyloxy)acetyl)-8-oxo-8,9,10,11-tetrahydro-5H-dibenzo[c,g]chromen-9-yl) 5-methylpyrrolidine-1,2-dicarboxylate

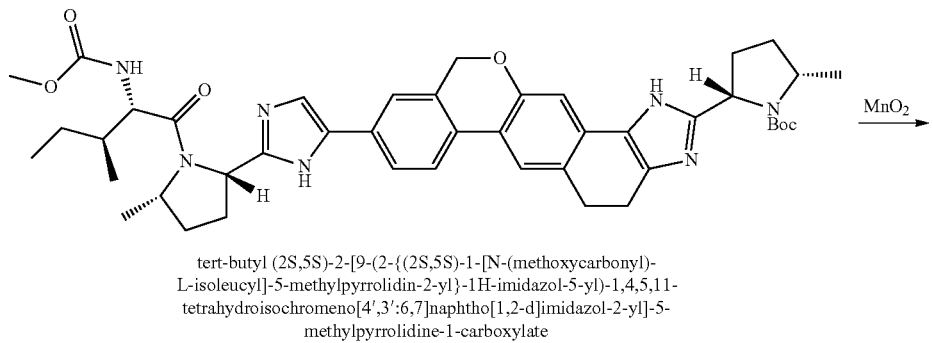

tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,4,5,11-tetrahydroisochromeno[4′,3′:6,7]naphtho[1,2-d]imidazol-2-yl]-5-methylpyrrolidine-1-carboxylate

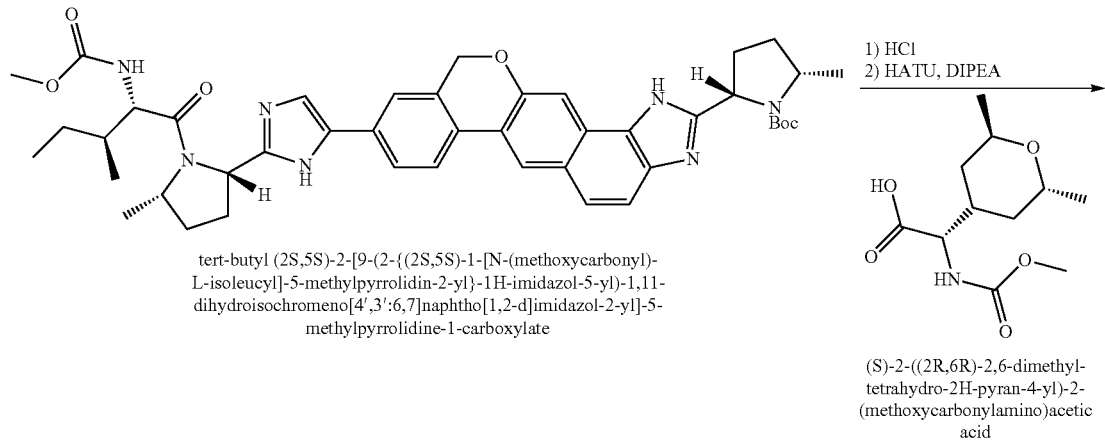

tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4′,3′:6,7]naphtho[1,2-d]imidazol-2-yl]-5-methylpyrrolidine-1-carboxylate (S)-2-((2R,6R)-2,6-dimethyl-tetrahydro-2H-pyran-4-yl)-2-(methoxycarbonylamino)acetic acid

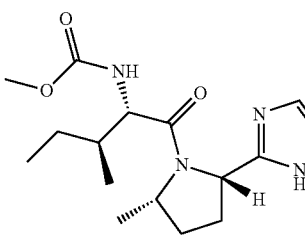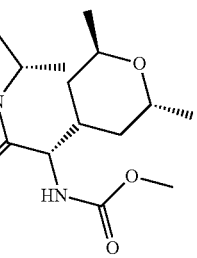

methyl {(2S,3S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate (2S,5S)-2-(9-Bromo-8-oxo-8,9,10,11-tetrahydro-5H-dibenzo[c,g]chromen-3-yl)-2-oxoethyl 1-((2S,3S)-2-(methoxycarbonylamino)-3-methylpentanoyl)-5-methylpyrrolidine-2-carboxylate To a slurry of 9-bromo-3-(2-bromoacetyl)-10,11-dihydro-5H-dibenzo[c,g]chromen-8(9H)-one (4.00 g, 8.88 mmol) in dichloromethane (50 mL) was added (2S,5S)-1-((2S,3S)-2-(methoxycarbonylamino)-3-methylpentanoyl)-5-methylpyrrolidine-2-carboxylic acid (2.80 g, 9.32 mmol) and K₂CO₃ (1.84 g, 13.31 mmol). The resulting slurry was stirred at room temperature for 18 h. The reaction was diluted with dichloromethane and washed with aqueous HCl (0.5 M) and Brine. The aqueous layers were back extracted with dichloromethane (2×), and the combined organic layers were dried over Na₂SO₄ and concentrated. The crude product was taken directly into the next reaction.

(2S,5S)-1-Tert-butyl 2-(3-(2-((2S,5S)-1-((2S,3S)-2-(methoxycarbonylamino)-3-methylpentanoyl)-5-methylpyrrolidine-2-carbonyloxy)acetyl)-8-oxo-8,9,10,11-tetrahydro-5H-dibenzo[c,g]chromen-9-yl) 5-methylpyrrolidine-1,2-dicarboxylate To a solution of (2S,5S)-2-(9-bromo-8-oxo-8,9,10,11-tetrahydro-5H-dibenzo[c,g]chromen-3-yl)-2-oxoethyl 1-((2S,3S)-2-(methoxycarbonylamino)-3-methylpentanoyl)-5-methylpyrrolidine-2-carboxylate (5.95 g, 8.88 mmol) in THF (60 mL) was added (2S,5S)-1-(tert-butoxycarbonyl)-5-methylpyrrolidine-2-carboxylic acid (3.05 g, 13.3 mmol) and Cs₂CO₃ (2.31 g, 7.09 mmol). The resulting solution was heated to 50° C. for 18 h. The solution was cooled to room temperature and diluted with EtOAc and washed with aqueous HCl (0.5 M). The aqueous layer was backextracted with EtOAc (2×), and the combined organic layers were dried over Na₂SO₄ and concentrated. The crude oil was purified by column chromatography (SiO₂, 25-100% EtOAc (5% MeOH)/Hexanes) to provide (2S,5S)-1-tert-butyl 2-(3-(2-((2S,5S)-1-((2S,3S)-2-(methoxycarbonylamino)-3-methylpentanoyl)-5-methylpyrrolidine-2-carbonyloxy)acetyl)-8-oxo-8,9,10,11-tetrahydro-5H-dibenzo[c,g]chromen-9-yl) 5-methylpyrrolidine-1,2-dicarboxylate (3.116, 43% over 2 steps) as a orange foam. LCMS-ESI+: calc'd for C44H55N3O12: 817.38 (M+). Found: 817.65 (M+).

Tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,4,5,11-tetrahydroisochromeno[4',3':6,7]naphtho[1,2-d]imidazol-2-yl]-5-methylpyrrolidine-1-carboxylate To a solution of (2S,5S)-1-tert-butyl 2-(3-(2-((2S,5S)-1-((2S,3S)-2-(methoxycarbonylamino)-3-methylpentanoyl)-5-methylpyrrolidine-2-carbonyloxy)acetyl)-8-oxo-8,9,10,11-tetrahydro-5H-dibenzo[c,g]chromen-9-yl) 5-methylpyrrolidine-1,2-dicarboxylate (3.116 g, 3.57 mmol) in toluene (35 mL) was added hexamethdisilazane (6.0 mL, 28.7 mmol), and propionic acid (8.0 mL, 107.1 mmol). The solution was heated to 90° C. for 18 h and cooled to room temperature. The solution was diluted with MeOH and basified with a 1:1 mixture of NH₄OH and water. The slurry was extracted with dichloromethane (3×). The combined organic layers were dried over Na₂SO₄ and concentrated. The crude oil was used directly in the next step. LCMS-ESI+: calc'd for C44H55N7O6: 777.42 (M+). Found: 778.30 (M+H+).

Tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidine-1-carboxylate To a solution of tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,4,5,11-tetrahydroisochromeno[4',3':6,7]naphtho[1,2-d]imidazol-2-yl]-5-methylpyrrolidine-1-carboxylate (2.77 g, 3.5 mmol) in dichloromethane (25 mL) was added MnO₂ (9.00 g, 103 mmol). The resulting slurry was stirred at room temperature for 20 h. The solution was diluted with dichloromethane, filtered through celite, and concentrated. The crude oil was purified by column chromatography (SiO₂, 0-5-10% EtOAc/MeOH) to provide tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidine-1-carboxylate (1.10 g, 40% over 2 steps) as a brown foam. LCMS-ESI+: calc'd for C44H53N7O6: 775.41 (M+). Found: 776.37 (M+H+)

Methyl {(2S,3S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate To a solution of tert-butyl (2S,5S)-2-[9-(2-{(2S,5S)-1-[N-(methoxycarbonyl)-L-isoleucyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidine-1-carboxylate (0.30 g, 0.39 mmol) in a mixture of dichloromethane (4 mL) and methanol (0.5 mL) was added HCl (4M in dioxanes, 1.45 mL, 5.80 mmol). The solution was heated to 40° C. for 1 h and cooled to room temperature. The solution was then concentrated in vacuo. The resulting solid was dissolved in DMF (3 mL), followed by the addition of (S)-2-((2R,6R)-2,6-dimethyltetrahydro-2H-pyran-4-yl)-2-(methoxycarbonylamino)acetic acid (0.11 g, 0.46 mmol), HATU (0.18 g, 0.48 mmol), and diisopropylethylamine (0.3 mL, 1.72 mmol). The resulting solution was stirred at room temperature for 3 h. Aqueous HCl (6M, 4 drops) was added and the solution was purified by reverse phase HPLC (Gemini column, 10-53% MeCN/H₂O/0.1% TFA). The desired fractions were combined, and the organics were concentrated in vacuo. The resulting aqueous solution was basified with saturated NaHCO₃ to provide a white precipitate. The solid was filtered and dried to provide methyl {(2S,3S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7] naphtho[1,2-d]imidazol-9-yl}-1H-imidazol-2-yl)-5-methylpyrrolidin-1-yl]-3-methyl-1-oxopentan-2-yl}carbamate (0.082 g, 23%) as a white powder. LCMS-ESI+: calc'd for C50H62N8O9: 903.08 (M+). Found: 903.84 (M+H+). 1H NMR (400 MHz, Methanol-d4) δ 8.36-8.22 (m, 1H), 7.98-7.82 (m, 1H), 7.69-7.20 (m, 8H), 5.22-5.07 (m, 3H), 5.02 (d, 1H), 4.73-4.64 (m, 1H), 4.49 (s, 3H), 4.26-3.97 (m, 4H), 3.79 (d, 1H), 3.72 (s, 1H), 3.63-3.52 (m, 4H), 3.47-3.32 (m, 1H), 2.61-2.43 (m, 1H), 2.32-1.98 (m, 4H), 1.95-1.78 (m, 1H), 1.79-1.65 (m, 1H), 1.54 (s, 4H), 1.41 (d, 2H), 1.28-1.09 (m, 3H), 1.04 (dd, 6H), 0.90 (d, 1H), 0.88-0.59 (m, 10H).

Example AB

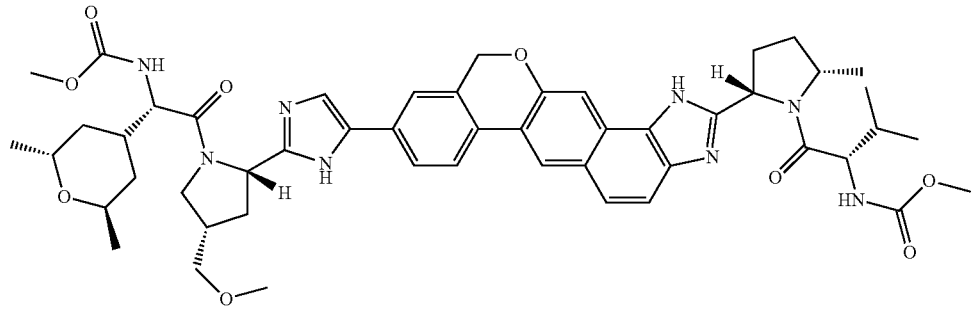

Methyl {(2S)-1-[(2S,5S)-2-(9-{2-[(2S,4S)-1-{(2S)-2-[(2R,6R)-2,6-dimethyltetrahydro-2H- pyran-4-yl]-2-[(methoxycarbonyl)amino]acetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Following Example AA, substituting (2S,4S)-1-(tert-butoxycarbonyl)-4-(methoxymethyl)pyrrolidine-2-carboxylic acid for (2S,5S)-1-((2S,3S)-2-(methoxycarbonylamino)-3-methylpentanoyl)-5-methylpyrrolidine-2-carboxylic acid and (2S,5S)-1-(S)-2-(methoxycarbonylamino)-3-methylbutanoyl)-5-methylpyrrolidine-2-carboxylic acid for (2S,5S)-1-(tert-butoxycarbonyl)-5-methylpyrrolidine-2-carboxylic acid, provided methyl {(2S)-1-[(2S,5S)-2-(9-{2-[(2S,4S)-1-{(2S)-2-[(2R,6R)-2,6-dimethyltetrahydro-2H-pyran-4-yl]-2-[(methoxycarbonyl)amino]acetyl}-4-(methoxymethyl) pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate (0.25 g). LCMS-ESI+: calc'd for C50H62N8O9: 918.46 (M+). Found: 919.97 (M+H+). 1H NMR (400 MHz, Methanol-d4) δ 8.39-8.11 (m, 1H), 8.09-7.40 (m, 5H), 7.28 (s, 2H), 5.27-4.91 (m, 5H), 4.49 (s, 3H), 4.34-4.14 (m, 2H), 4.14-4.00 (m, 3H), 3.80 (s, 1H), 3.59 (s, 2H), 3.57 (s, 3H), 3.54-3.39 (m, 3H), 3.31 (s, 3H), 2.68-2.46 (m, 2H), 2.45-2.30 (m, 1H), 2.31-1.93 (m, 5H), 1.94-1.81 (m, 1H), 1.50 (d, 2H), 1.46-1.25 (m, 4H), 1.10 (dd, 3H), 1.06-0.90 (m, 9H), 0.87 (d, 2H).

Example AC

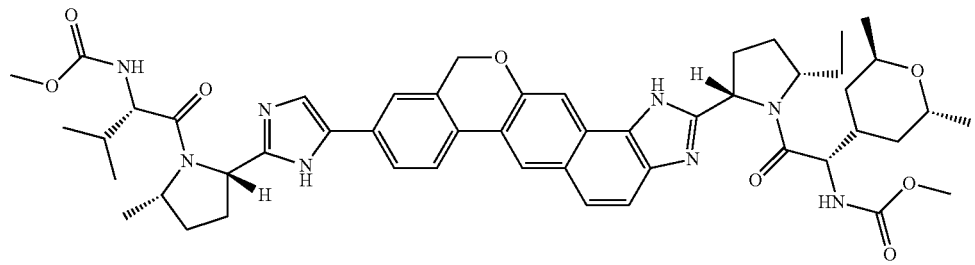

Methyl {(1S)-1-[(2R,6R)-2,6-dimethyltetrahydro-2H-pyran-4-yl]-2-[(2S,5S)-2-ethyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxoethyl}carbamate Following Example AA, substituting (2S,4S)-1-(tert-butoxycarbonyl)-4-(methoxymethyl)pyrrolidine-2-carboxylic acid for (2S,5S)-1-((S)-2-(methoxycarbonylamino)-3-methylbutanoyl)-5-methylpyrrolidine-2-carboxylic acid and (2S,5S)-1-(S)-2-(methoxycarbonylamino)-3-methylbutanoyl)-5-methylpyrrolidine-2-carboxylic acid for (2S,5S)-1-(tert-butoxycarbonyl)-5-ethylpyrrolidine-2-carboxylic acid, provided methyl {(1S)-1-[(2R,6R)-2,6-dimethyltetrahydro-2H-pyran-4-yl]-2-[(2S,5S)-2-ethyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxoethyl}carbamate (0.21 g). LCMS-ESI+: calc'd for C50H62N8O8: 902.47 (M+). Found: 904.14 (M+H+). 1H NMR (400 MHz, Methanol-d4) δ 8.33-8.04 (m, 1H), 8.01-7.68 (m, 1H), 7.68-7.37 (m, 14H), 7.32-7.17 (m, 1H), 5.22-4.95 (m, 3H), 4.50 (s, 6H), 4.31-3.92 (m, 5H), 3.80 (s, 1H), 3.58 (d, J=2.9 Hz, 4H), 3.52-3.35 (m, 1H), 2.56-2.39 (m, 1H), 2.31-2.11 (m, 2H), 2.12-1.88 (m, 3H), 1.88-1.76 (m, 1H), 1.76-1.48 (m, 1H), 1.40 (d, J=6.7 Hz, 2H), 1.21 (d, J=7.0 Hz, 2H), 1.12-1.02 (m, 4H), 0.99 (t, J=7.3 Hz, 1H), 0.93 (d, J=7.0 Hz, 1H), 0.89 (d, J=6.6 Hz, 1H), 0.87-0.74 (m, 5H), 0.70-0.45 (m, 1H).

Example AD

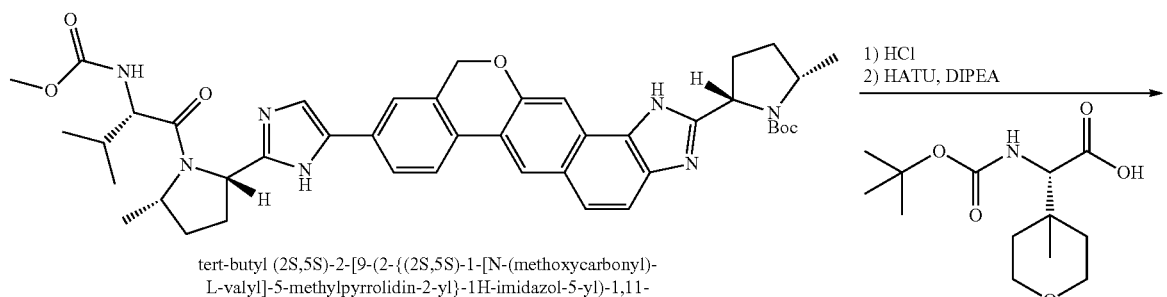

tert-butyl (2S,5S)-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidine-1-carb (S)-2-(tert-butoxycarbonylamino)-2-(4-methyltetrahydro-2H-pyran-4-yl)acetic acid

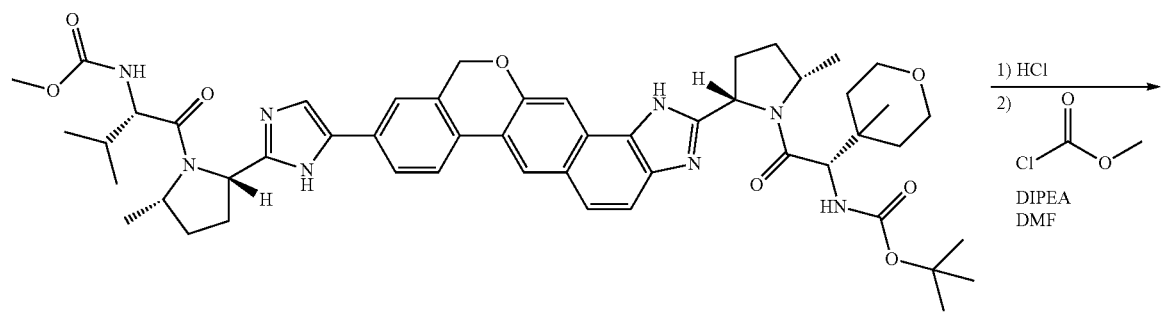

methyl [(2S)-1-{(2S,5S)-2-[5-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate

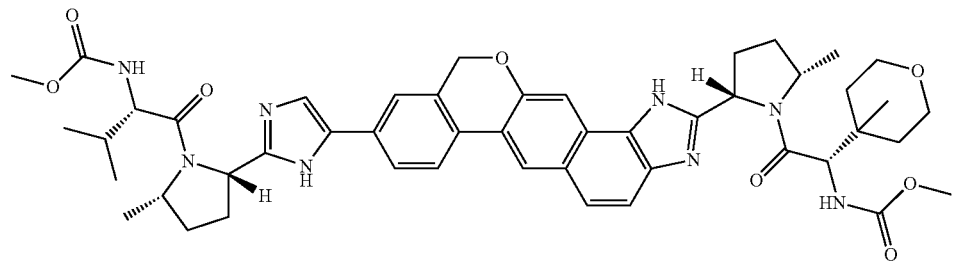

methyl [(2S)-1-{(2S,5S)-2-[5-(2-{(2S,5S)-1-[(2S)-2-[(methoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate

Methyl [(2S)-1-{(2S,5S)-2-[5-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate Methyl [(2S)-1-{(2S,5S)-2-[5-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid and substituting (S)-2-((2R,6R)-2,6-dimethyltetrahydro-2H-pyran-4-yl)-2-(methoxycarbonylamino)acetic acid with (S)-2-(tert-butoxycarbonylamino)-2-(4-methyltetrahydro-2H-pyran-4-yl)acetic acid. MS (ESI) m/z 917.62 [M+H]+.

Methyl [(2S)-1-{(2S,5S)-2-[5-(2-{(2S,5S)-1-[(2S)-2-[(methoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate To as solution of methyl [(2S)-1-{(2S,5S)-2-[5-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate (0.594 g, 0.648 mmol) in a mixture of dichloromethane (6.4 mL) and methanol (1.2 mL) was added HCl (4M in dioxanes, 2.4 mL, 9.72 mmol). The solution was heated to 40° C. for 1 h and cooled to room temperature. The solution was then concentrated in vacuo. The resulting solid was dissolved in DMF (3 mL), followed by the addition of methyl chloroformate (0.050 mL, 0.648 mmol) and diisopropylethylamine (0.14 mL, 0.78 mmol). The reaction mixture was stirred at room temperature for 30 minutes. Upon completion by LCMS monitoring, the solution was purified by reverse phase HPLC (Gemini column, 10-45% MeCN/H2O/0.1% TFA). The desired fractions were lyophilized to give methyl [(2S)-1-{(2S,5S)-2-[5-(2-{(2S,5S)-1-[(2S)-2-[(methoxycarbonyl)amino]-2-(4-methyltetrahydro-2H-pyran-4-yl)acetyl]-5-methylpyrrolidin-2-yl}-1,11-dihydroisochromeno[4',3':6,7]naphtho[1,2-d]imidazol-9-yl)-1H-imidazol-2-yl]-5-methylpyrrolidin-1-yl}-3-methyl-1-oxobutan-2-yl]carbamate (0.057 g, 10%). 1H NMR (400 MHz, Methanol-d4) δ 8.63 (s, 1H), 8.19 (d, 1H), 8.09-7.75 (m, 4H), 7.75-7.61 (m, 2H), 7.46-7.24 (m, 1H), 5.39-5.24 (m, 2H), 5.23-5.12 (m, 1H), 4.84-4.60 (m, 2H), 4.44-4.22 (m, 1H), 4.22-4.02 (m, 1H), 3.85-3.62 (m, 8H), 3.60-3.45 (m, 2H), 2.84-2.44 (m, 2H), 2.42-2.23 (m, 3H), 2.12-1.82 (m, 3H), 1.67 (d, 2H), 1.56 (d, 4H), 1.37-1.19 (m, 4H), 1.17-1.03 (m, 4H), 0.98 (d, 3H), 0.88 (d, 3H). MS (ESI) m/z 875.53 [M+H]+.

Example AE

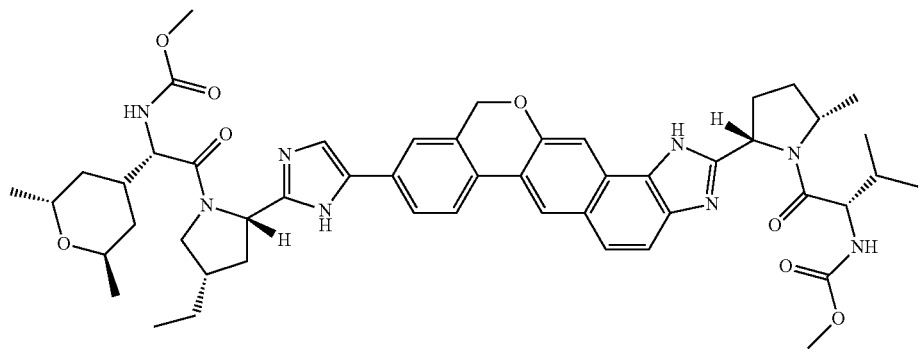

methyl [(1S)-1-[(2R,6R)-2,6-dimethyltetrahydro-2H-pyran-4-yl]-2-{(2S,4S)-4-ethyl-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]pyrrolidin-1-yl}-2-oxoethyl]carbamate

Methyl [(1S)-1-[(2R,6R)-2,6-dimethyltetrahydro-2H-pyran-4-yl]-2-{(2S,4S)-4-ethyl-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]pyrrolidin-1-yl}-2-oxoethyl]carbamate Methyl [(1S)-1-[(2R,6R)-2,6-dimethyltetrahydro-2H-pyran-4-yl]-2-{(2S,4S)-4-ethyl-2-[5-(2-{(2S,5S)-1-[N-(methoxycarbonyl)-L-valyl]-5-methylpyrrolidin-2-yl}-1,11-dihydroisochromeno[4',3':6,7]naphtho[1,2-d]imidazol-9-yl)-1H-imidazol-2-yl]pyrrolidin-1-yl}-2-oxoethyl]carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,4S)-1-(tert-butoxycarbonyl)-4-ethylpyrrolidine-2-carboxylic acid and substituting (2S,5S)-1-(tert-butoxycarbonyl)-5-methylpyrrolidine-2-carboxylic acid with (2S,5S)-1-(S)-2-(methoxycarbonylamino)-3-methylbutanoyl)-5-methylpyrrolidine-2-carboxylic acid. 1H NMR (400 MHz, Methanol-d4) δ 8.48-8.29 (m, 1H), 8.10-7.91 (m, 1H), 7.86-7.23 (m, 5H), 5.35-5.15 (m, 2H), 5.07 (t, 1H), 4.46-4.26 (m, 2H), 4.25-4.07 (m, 2H), 3.91 (s, 1H), 3.66 (d, 5H), 3.52-3.37 (m, 1H), 2.74-2.41 (m, 2H), 2.40-1.89 (m, 6H), 1.75-1.34 (m, 7H), 1.33-0.75 (m, 18H). MS (ESI) m/z 903.99 [M+H]+.

Example AF

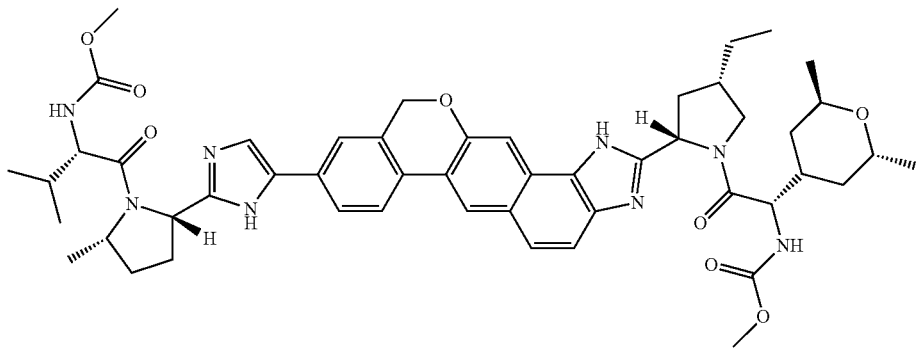

methyl [(1S)-1-[(2R,6R)-2,6-dimethyltetrahydro-2H-pyran-4-yl]-2-{(2S,4S)-4-ethyl-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]pyrrolidin-1-yl}-2-oxoethyl]carbamate Methyl [(1S)-1-[(2R,6R)-2,6-dimethyltetrahydro-2H-pyran-4-yl]-2-{(2S,4S)-4-ethyl-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]pyrrolidin-1-yl}-2-oxoethyl]carbamate Methyl [(1S)-1-[(2R,6R)-2,6-dimethyltetrahydro-2H-pyran-4-yl]-2-{(2S,4S)-4-ethyl-2-[9-(2-{(2S,5S)-1-[N-(methoxycarbonyl)-L-valyl]-5-methylpyrrolidin-2-yl}-1H-imidazol-5-yl)-1,11-dihydroisochromeno[4',3':6,7]naphtho[1,2-d]imidazol-2-yl]pyrrolidin-1-yl}-2-oxoethyl]carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(S)-2-(methoxycarbonylamino)-3-methylbutanoyl)-5-methylpyrrolidine-2-carboxylic acid and substituting (2S,5S)-1-(tert-butoxycarbonyl)-5-methylpyrrolidine-2-carboxylic acid with (2S,4S)-1-(tert-butoxycarbonyl)-4-ethylpyrrolidine-2-carboxylic acid. 1H NMR (400 MHz, Methanol-d4) δ 8.34 (d, 1H), 7.94 (dd, 1H), 7.88-7.60 (m, 3H), 7.59-7.28 (m, 2H), 5.25-5.11 (m, 3H), 4.54 (s, 1H), 4.39 (t, 1H), 4.27-4.12 (m, 2H), 4.12-4.02 (m, 1H), 3.62 (d, 4H), 3.48 (s, 3H), 3.13 (s, 3H), 2.68-2.45 (m, 1H), 2.38-2.19 (m, 2H), 2.19-1.83 (m, 4H), 1.70-1.53 (m, 2H), 1.46 (d, 2H), 1.44-1.28 (m, 3H), 1.28-1.13 (m, 1H), 1.10 (d, 3H), 1.07-0.87 (m, 12H), 0.85-0.77 (m, 1H). MS (ESI) m/z 903.88 [M+H]+.

Example AG

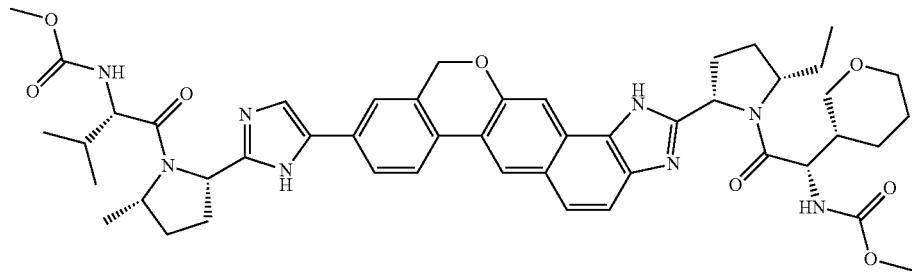

methyl {(1S)-2-[(2S,5S)-2-ethyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3R)-tetrahydro-2H-pyran-3-yl]ethyl}carbamate

123

Methyl {(1S)-2-[(2S,5S)-2-ethyl-5-(9-{2-[(2S,5S)-1-{(2S)-2[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3R)-tetrahydro-2H-pyran-3-yl]ethyl}carbamate Methyl {(1S)-2-[(2S,5S)-2-ethyl-5-(9-{2-[(2S,5S)-1-{(2S)-2[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3R)-tetrahydro-2H-pyran-3-yl]ethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid; (2S,5S)-1-(tert-butoxycarbonyl)-5-methylpyrrolidine-2-carboxylic acid with (2S,5S)-1-(tert-butoxy carbonyl)-5-ethyl pyrrolidine-2-carboxylic acid and (S)-2-((2R,6R)-2,6-dimethyltetrahydro-2H-pyran-4-yl)-2-(methoxycarbonylamino)acetic acid with (S)-2-(methoxycarbonylamino)-2-((R)-tetrahydro-2H-pyran-3-yl)acetic acid. $^1$H NMR (400 MHz, dmso) δ 8.60 (s, 1H), 8.25-7.43 (m, 7H), 5.23 (s, 2H), 5.13 (m, 1H), 5.01-4.90 (m, 1H), 4.59 (s, 1H), 4.33 (m, 2H), 4.12-3.43 (m, 14H), 3.37 (m, 1H), 3.08 (m, 2H), 2.39-1.70 (m, 10H), 1.44 (m, 5H), 1.12 (m, 2H), 0.92 (m, 5H), 0.73-0.54 (m, 3H) MS (ESI) m/z 875.95 [M+H]$^+$.

Example AH

124

Methyl {(1S)-2-[(2S,5S)-2-ethyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3S)-tetrahydro-2H-pyran-3-yl]ethyl}carbamate Methyl {(1S)-2-[(2S,5S)-2-ethyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3S)-tetrahydro-2H-pyran-3-yl]ethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(S)-2-(methoxycarbonylamino)-3-methylbutanoyl)-5-methylpyrrolidine-2-carboxylic acid; (2S,5S)-1-(tert-butoxycarbonyl)-5-methylpyrrolidine-2-carboxylic acid with (2S,5S)-1-(tert-butoxycarbonyl)-5-ethylpyrrolidine-2-carboxylic acid and (S)-2-((2R,6R)-2,6-dimethyltetrahydro-2H-pyran-4-yl)-2-(methoxycarbonylamino)acetic acid with (S)-2-(methoxycarbonylamino)-2-((S)-tetrahydro-2H-pyran-3-yl)acetic acid. $^1$H NMR (400 MHz, dmso) δ 8.64 (s, 1H), 8.24-7.46 (m, 8H), 5.27 (s, 2H), 5.13 (s, 1H), 4.99 (s, 1H), 4.62 (s, 1H), 4.12 m, 5H), 3.67-3.23 (m, 8H), 3.12 (s, 1H), 2.43-2.06 (m, 6H), 2.04-1.63 (m, 8H), 1.47 (m, 4H), 1.38-1.07 (m, 3H), 0.95 (m, 6H), 0.79-0.62 (m, 3H). MS (ESI) m/z 875.86 [M+H]$^+$.

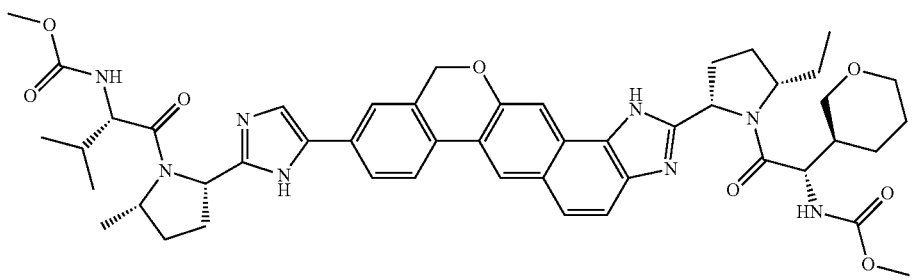

methyl {(1S)-2-[(2S,5S)-2-ethyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3S)-tetrahydro-2H-pyran-3-yl]ethyl}carbamate

Example AI

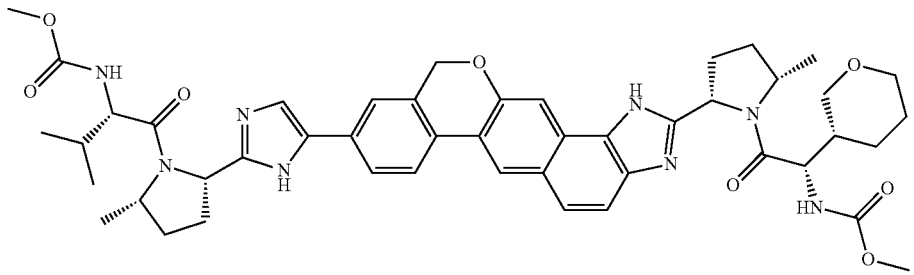

methyl {(1S)-2-[(2S,5S)-2-methyl-5-(9-{2-[(2S,5S)-1-{(2S)-2-[(methoxy carbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3R)-tetrahydro-2H-pyran-3-yl]ethyl}carbamate Methyl {(1S)-2-[(2S,5S)-2-methyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3R)-tetrahydro-2H-pyran-3-yl]ethyl}carbamate Methyl {(1S)-2-[(2S,5S)-2-methyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3R)-tetrahydro-2H-pyran-3-yl]ethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxy carbonylamino)-3-methylbutanoyl)-5-methylpyrrolidine-2-carboxylic acid and (S)-2-(2R,6R)-2,6-dimethyltetrahydro-2H-pyran-4-yl)-2-(methoxycarbonylamino)acetic acid with (S)-2-(methoxycarbonylamino)-2-((R)-tetrahydro-2H-pyran-3-yl)acetic acid. $^1$H NMR (400 MHz, dmso) δ 8.60 (s, 1H), 8.25-7.46 (m, 7H), 5.23 (s, 2H), 5.11 (m, 1H), 4.96 (s, 1H), 4.64 (m, 2H), 4.16-3.58 (m, 9H), 3.56-3.31 (m, 6H), 3.08 (m, 3H), 2.19 (m, 5H), 1.86 (m, 3H), 1.43 (m, 7H), 1.24-0.92 (m, 3H), 0.83 (m, 3H), 0.68 (m, 3H). MS (ESI) m/z 861.45 [M+H]$^+$.

Example AJ

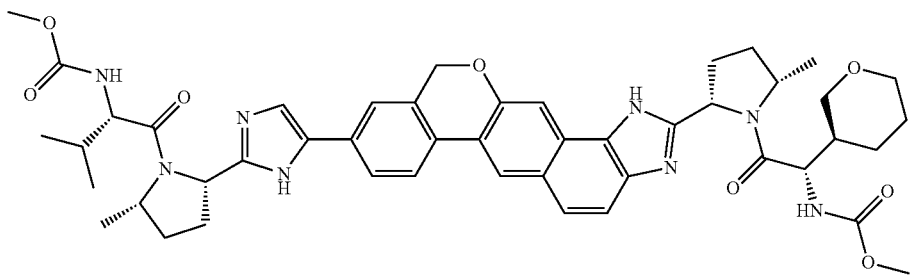

methyl {(1S)-2-[(2S,5S)-2-methyl-5-(9-{2-[(2S,5S)-1-{(2S)-2-[(methoxy carbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3S)-tetrahydro-2H-pyran-3-yl]ethyl}carbamate Methyl {(1S)-2-[(2S,5S)-2-methyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3S)-tetrahydro-2H-pyran-3-yl]ethyl}carbamate Methyl {(1S)-2-[(2S,5S)-2-methyl-5-(9-{2-[(2S,5S)-1-{(2S)-2-[(methoxycarbonyl)amino]-3-methylbutanoyl}-5-methylpyrrolidin-2-yl]-1H-imidazol-5-yl}-1,11-dihydroisochromeno[4',3':6,7]naphtho[1,2-d]imidazol-2-yl)pyrrolidin-1-yl]-2-oxo-1-[(3S)-tetrahydro-2H-pyran-3-yl]ethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxy carbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (S)-2-(methoxycarbonylamino)-2-((S)-tetrahydro-2H-pyran-3-yl)acetic acid. $^1$H NMR (400 MHz, dmso) δ 8.74-8.44 (m, 1H), 8.26-7.31 (m, 9H), 5.25 (s, 2H), 5.19-5.04 (m, 1H), 5.04-4.87 (m, 1H), 4.77-4.48 (m, 1H), 4.44-3.73 (m, 2H), 3.66-2.95 (m, 4H), 2.29 (s, 8H), 1.83 (s, 7H), 1.46 (m, 12H), 0.85 (m, 5H), 0.72 (m, 3H). MS (ESI) m/z 861.41 [M+H]$^+$.

Example AK

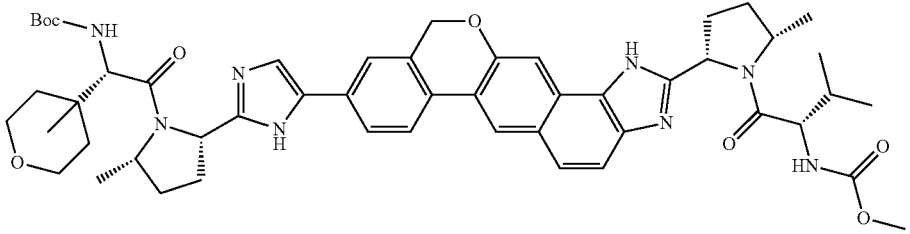

methyl [(2S)-1-{(2S,5S)-2-[9-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate Methyl [(2S)-1-{(2S,5S)-2-[9-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate Methyl [(2S)-1-{(2S,5S)-2-[9-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid; (2S,5S)-1-(tert-butoxycarbonyl)-5-methylpyrrolidine-2-carboxylic acid with (2S,5S)-1-((S)-2-(methoxy carbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (S)-2-(tert-butoxycarbonylamino)-2-(4-methyltetrahydro-2H-pyran-4-yl)acetic acid

Example AL

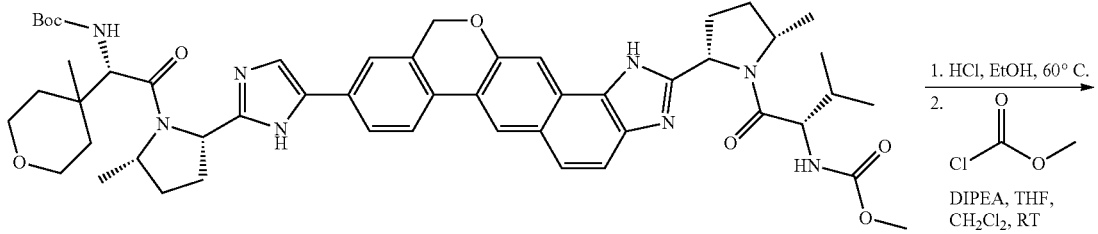

methyl [(2S)-1-{(2S,5S)-2-[5-(2-{(2S,5S)-1-[(2S)-2-[(tert-butoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate

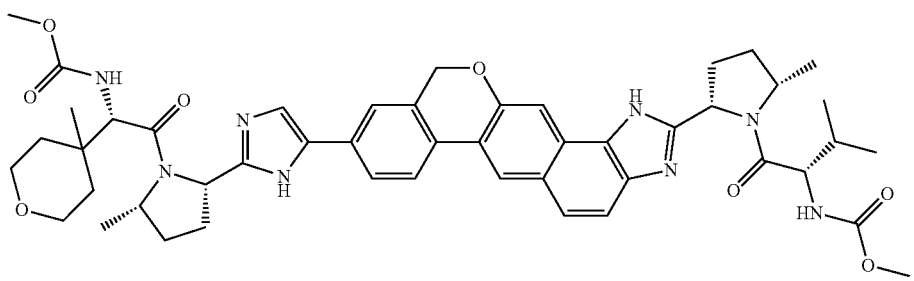

methyl [(2S)-1-{(2S,5S)-2-[9-(2-{(2S,5S)-1-[(2S)-2-[(methoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate

129

Methyl [(2S)-1-{(2S,5S)-2-[9-(2-{(2S,5S)-1-[(2S)-2-[(methoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate Tert-butyl (2S,4S)-2-[5-(2-{(2S,4S)-1-[N-(methoxy carbonyl)-L-valyl]-5-methylpyrrolidin-2-yl}-1,11-dihydroisochromeno[4',3':6,7]naphtha[1,2-d]imidazol-9-yl)-1H-imidazol-2-yl]-5-methylpyrrolidine-1-carboxylate (316 mg, 0.34 mmol) was dissolved in EtOH (3 mL) and HCl (1 mL) was added. The reaction mixture was stirred for 1 h at 60° C. and then concentrated under reduced pressure. The crude residue was dissolved in THF (3 mL) and $CH_2Cl_2$ (3 mL) treated with DIPEA (0.18 mL, 1.0 mmol) and methyl chloroformate (0.0.03 mL, 0.38 mmol). After 1 h, the mixture was diluted with EtOAc and washed successively with water and brine. The organics were dried over $Na_2SO_4$, filtered and concentrated under reduced pressure. The crude residue was purified by reverse phase HPLC (Gemini, 15 to 45% ACN/$H_2O$+0.1% TFA). to afford methyl [(2S)-1-{(2S,5S)-2-[9-(2-{(2S,5S)-1-[(2S)-2-[(methoxycarbonyl)amino]-2-(4-methyltetrahydro-2H-pyran-4-yl)acetyl]-5-methylpyrrolidin-2-yl}-1H-imidazol-5-yl)-1,11-dihydroisochromeno[4',3':6,7]naphtho[1,2-d]imidazol-2-yl]-5-methylpyrrolidin-1-yl}-3-methyl-1-oxobutan-2-yl]carbamate (100 mg, 33%). $^1$H NMR (400 MHz, dmso) δ 8.67 (s, 1H), 8.26-7.47 (m, 8H), 5.27 (m, 2H), 5.15 (m, 1H), 5.02-4.90 (m, 1H), 4.70 (s, 1H), 4.44 (s, 1H), 4.29-3.28 (m, 16H), 2.21 (m, 5H), 1.75 (m, 3H), 1.49 (m, 6H), 1.35-1.05 (m, 3H), 1.02-0.86 (m, 4H), 0.83 (m, 3H), 0.72 (m, 3H). MS (ESI) m/z 875.91 [M+H]$^+$.

Example AM

130

Methyl {(2S)-1-[(2S,5S)-2-(5-{2-[(2S,5S)-1-{(2S)-2-[(2R,6S)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,5S)-1-{(2S)-2-[(2R,6S)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (2S)-2-((2R,6S)-2,6-dimethyltetrahydro-2H-pyran-4-yl)-2-(methoxycarbonylamino) acetic acid. $^1$H NMR (400 MHz, dmso) δ 8.64 (s, 1H), 8.29-7.49 (m, 7H), 5.26 (s, 2H), 5.15 (m, 1H), 5.07-4.91 (m, 1H), 4.61 (m, 2H), 4.17-3.29 (m, 16H), 2.43-2.02 (m, 8H), 1.83 (s, 2H), 1.47 (m, 5H), 1.36-0.76 (m, 12H), 0.71 (m, 3H). MS (ESI) m/z 889.60 [M+H]$^+$.

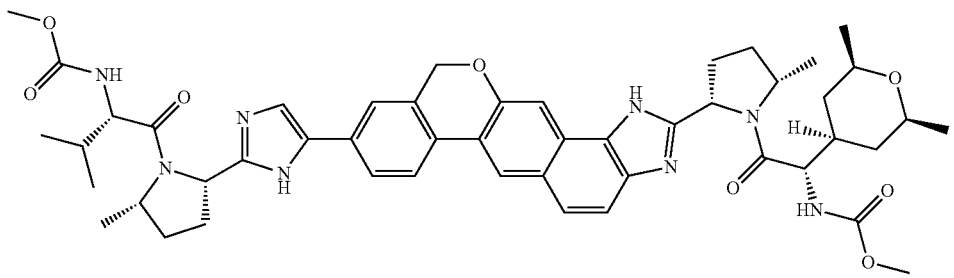

methyl {(2S)-1-[(2S,5S)-2-(5-{2-[(2S,5S)-1-{(2S)-2-[(2R,6S)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate

Example AN

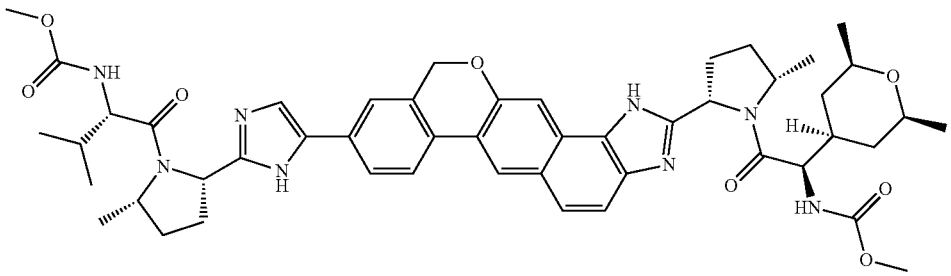

methyl {(2S)-1-[(2S,5S)-2-(5-{2-[(2S,5S)-1-{(2R)-2-[(2R,6S)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methyl pyrrolidin-1-yl]-3-methyl-1-oxobutan-2-yl}carbamate Methyl {(2S)-1-[(2S,5S)-2-(5-{2-[(2S,5S)-1-{(2R)-2-[(2R,6S)-2,6-dimethyltetrahydro-2H- pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,5S)-1-{(2R)-2-[(2R,6S)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (2R)-2-((2R,6S)-2,6-dimethyltetrahydro-2H-pyran-4-yl)-2-(methoxycarbonylamino) acetic acid. $^1$H NMR (400 MHz, dmso) δ 8.59 (m, 2H), 8.27-7.25 (m, 6H), 5.23 (m, 2H), 5.06-4.86 (m, 1H), 4.76-4.21 (m, 3H), 4.12-2.96 (m, 18H), 2.51-1.69 (m, 12H), 1.65-1.33 (m, 6H), 1.25-0.55 (m, 8H), 0.07 (m, 2H). MS (ESI) m/z 889.69 [M+H]$^+$.

Methyl {(2S)-1-[(2S,5S)-2-(9-{2-[(2S,5S)-1-{(2S)-2-[(2R,6S)-2,6-dimethyltetrahydro-2H- pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,5S)-1-{(2S)-2-[(2R,6S)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid; (2S,5S)-1-(tert-butoxycarbonyl)-5-methylpyrrolidine-2-carboxylic acid with (2S,5S)-1-(S)-2-(methoxycarbonylamino)-3-methylbutanoyl)-5-methylpyrrolidine-2-carboxylic acid and (S)-2-(2R,6R)-2,6-dimethyltetrahydro-2H-pyran-4-yl)-2-(methoxycarbonylamino)acetic acid with (2S)-2-((2R,6S)-2,6-dimethyltetrahydro-2H-pyran-4-yl)-2-(methoxycarbonyl amino)acetic acid. $^1$H NMR (400 MHz, dmso) δ 8.60 (s, 2H), 8.25-7.37 (m, 8H), 5.22 (s, 2H), 5.11 (s, 1H), 4.95 (s, 1H), 4.67 (s, 1H), 4.52 (m, 2H), 3.56 (m, 15H), 2.25 (m, 8H), 1.80 (s, 2H), 1.44 (m, 6H), 1.26-0.54 (m, 12H) MS (ESI) m/z 889.56 [M+H]$^+$.

Example AO

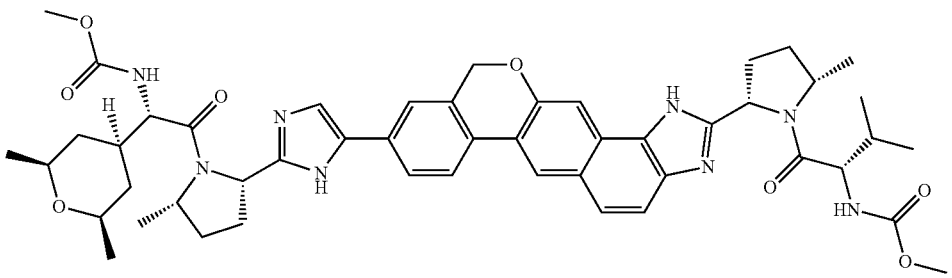

methyl {(2S)-1-[(2S,5S)-2-(9-{2-[(2S,5S)-1-{(2S)-2-[(2R,6S)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate

Example AP

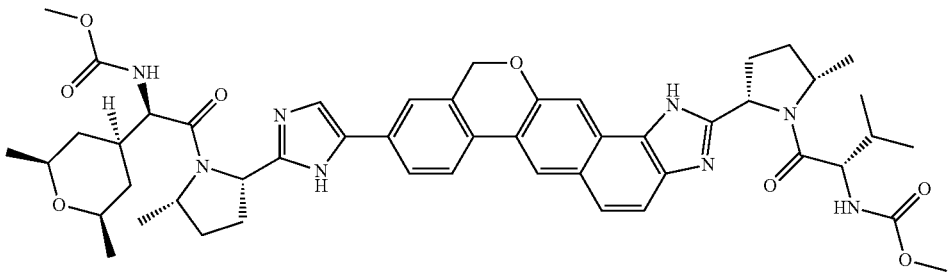

methyl {(2S)-1-[(2S,5S)-2-(9-{2-[(2S,5S)-1-{(2R)-2-[(2R,6S)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,5S)-1-{(2R)-2-[(2R,6S)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,5S)-1-{(2R)-2-[(2R,6S)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid; (2S,5S)-1-(tert-butoxycarbonyl)-5-methylpyrrolidine-2-carboxylic acid with (2S,5S)-1-((S)-2-(methoxycarbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (2R)-2-((2R,6S)-2,6-dimethyltetrahydro-2H-pyran-4-yl)-2-(methoxycarbonylamino)acetic acid. $^1$H NMR (400 MHz, dmso) δ 8.60 (m, 1H), 8.24-7.41 (m, 8H), 5.23 (m, 2H), 5.10 (m, 2H), 4.65 (s, 2H), 3.73 (m, 14H), 2.33 (m, 11H), 1.84 (s, 3H), 1.54-1.30 (m, 5H), 1.29-0.61 (m, 1H), 0.48 (s, 1H). MS (ESI) m/z 890.05 [M+H]$^+$.

Methyl {(2S)-1-[(2S,5S)-2-(5-[2-1(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid. $^1$H NMR (400 MHz, dmso) δ 8.63 (s, 1H), 8.24-7.44 (m, 8H), 5.25 (s, 2H), 5.14 (s, 1H), 4.99 (s, 1H), 4.67 (m, 2H), 3.96 (m, 5H), 3.48 (m, 12H), 2.44-1.75 (m, 9H), 1.48 (m, 6H), 1.30-1.10 (m, 3H), 1.01 (m, 3H), 0.85 (m, 4H), 0.75 (m, 3H). MS (ESI) m/z 889.58 [M+H]$^+$.

Example AQ

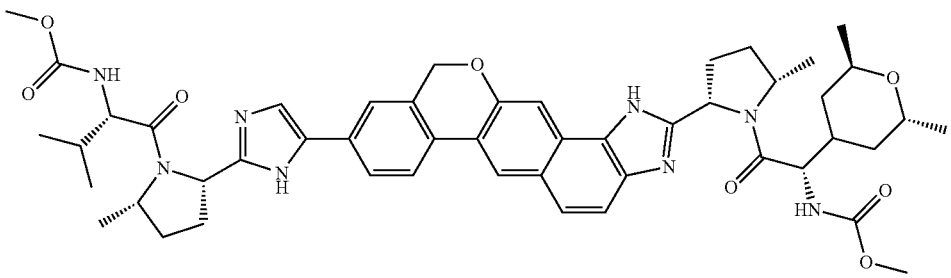

methyl {(2S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methyl pyrrolidin-1-yl]-3-methyl-1-oxobutan-2-yl}carbamate

Example AR

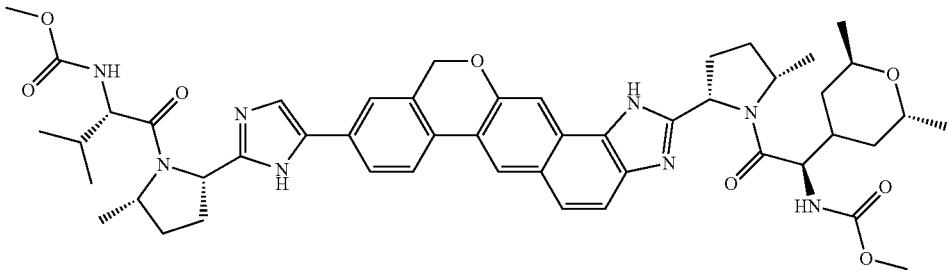

methyl {(2S)-1-[(2S,5S)-2-(5-{2-[(2S,5S)-1-{(2R)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methyl pyrrolidin-1-yl]-3-methyl-1-oxobutan-2-yl}carbamate Methyl {(2S)-1-[(2S,5S)-2-(5-{2-[(2S,5S)-1-{(2R)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,5S)-1-{(2R)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (R)-2-((2R,6R)-2,6-dimethyltetrahydro-2H-pyran-4-yl)-2-(methoxycarbonylamino) acetic acid. $^1$H NMR (400 MHz, dmso) δ 8.64 (m, 1H), 7.67 (m, 7H), 5.36-5.12 (m, 2H), 4.99 (s, 1H), 4.62 (s, 1H), 4.38 (s, 1H), 4.22 (s, 1H), 4.16-4.02 (m, 1H), 4.00-3.84 (m, 1H), 3.70-3.09 (m, 12H), 2.24 (m, 5H), 1.84 (s, 2H), 1.60 (s, 1H), 1.44 (m, 4H), 1.33-0.36 (m, 19H). MS (ESI) m/z 889.76 [M+H]$^+$.

Example AS

Methyl {(2S)-1-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methyl pentanoyl)-5-methylpyrrolidine-2-carboxylic acid with (2S,5S)-1-(tert-butoxycarbonyl)-5-methylpyrrolidine-2-carboxylic acid and (2S,5S)-1-(tert-butoxycarbonyl)-5-methylpyrrolidine-2-carboxylic acid with (2S,5S)-1-(S)-2-(methoxycarbonylamino)-3-methylbutanoyl)-5-methylpyrrolidine-2-carboxylic acid. $^1$H NMR (400 MHz, dmso) δ 8.65 (s, 1H), 8.23-7.44 (m, 8H), 5.26 (s, 2H), 5.15 (s, 1H), 4.99 (s, 1H), 4.66 (m, 2H), 4.24-3.82 (m, 4H), 3.75-3.20 (m, 12H), 2.42-1.72 (m, 10H), 1.47 (m, 5H), 1.30-0.96 (m, 6H), 0.95-0.62 (m, 8H). MS (ESI) m/z 889.88 [M+H]$^+$.

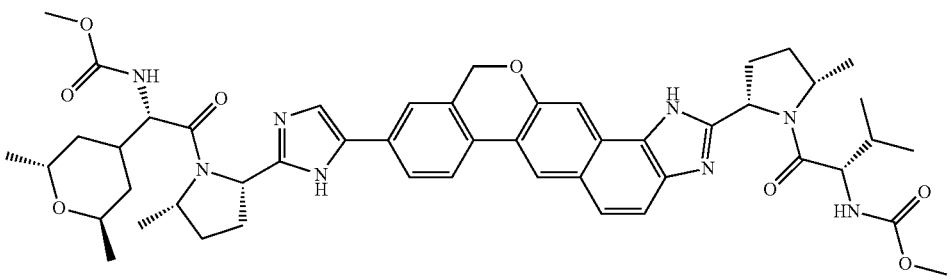

methyl {(2S)-1-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Example AT

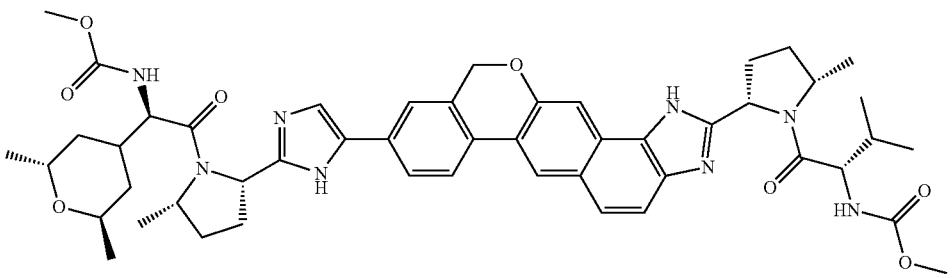

Methyl {(2S)-1-[(2S,5S)-2-(9-{2-[(2S,5S)-1-{(2R)-2-[(2R,6R)-2,6-dimethyltetrahydro-2H- pyran-4-yl]-2-[(methoxycarbonyl)amino]acetyl}-5-methylpyrrolidin-2-yl]-1H-imidazol-5-yl]-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S,5S)-1-{(2R)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid; (2S,5S)-1-(tert-butoxycarbonyl)-5-methylpyrrolidine-2-carboxylic acid with (2S,5S)-1-((S)-2-(methoxycarbonylamino)-3-methylbutanoyl)-5-methylpyrrolidine-2-carboxylic acid and (S)-2-((2R,6R)-2,6-dimethyltetrahydro-2H-pyran-4-yl)-2-(methoxycarbonylamino)acetic acid with (R)-2-((2R,6R)-2,6-dimethyltetrahydro-2H-pyran-4-yl)-2-(methoxycarbonyl amino)acetic acid $^1$H NMR (400 MHz, dmso) δ 8.65 (s, 1H), 7.74 (m, 8H), 5.71-5.53 (m, 1H), 5.28 (s, 2H), 5.15 (s, 1H), 5.05 (s, 1H), 4.70 (s, 1H), 4.13 (m, 5H), 3.82-3.15 (m, 10H), 2.70-2.57 (m, 1H), 2.43-1.71 (m, 9H), 1.67-1.29 (m, 6H), 1.28-0.54 (m, 14H). MS (ESI) m/z 889.53 [M+H]$^+$.

Example AU

Methyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate Methyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid. $^1$H NMR (400 MHz, dmso) δ 12.94 (s, 1H), 12.36 (s, 1H), 11.77 (s, 1H), 8.42 (m, 1H), 8.13-7.16 (m, 7H), 5.11 (s, 3H), 4.96 (s, 1H), 4.64 (s, 2H), 3.97 (m, 4H), 3.67-3.11 (m, 13H), 2.39-1.66 (m, 10H), 1.62-1.30 (m, 7H), 1.30-0.92 (m, 9H), 0.81 (m, 6H). MS (ESI) m/z 960.04 [M+H]$^+$.

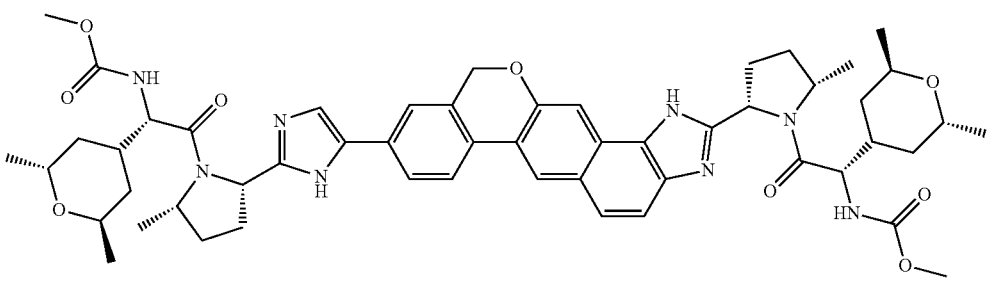

methyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate

Example AV

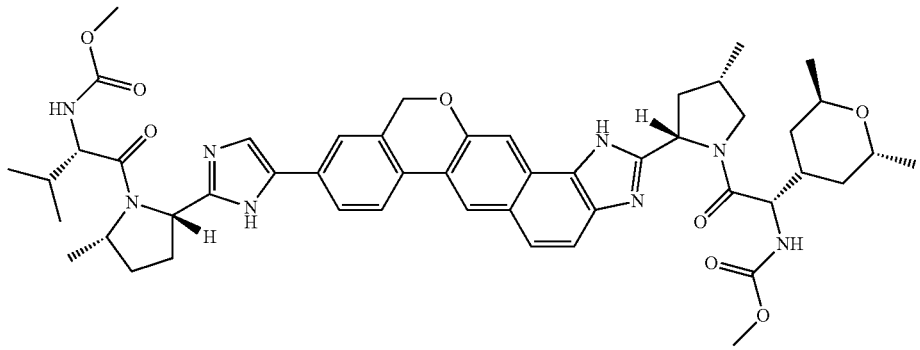

methyl {(2S)-1-[(2S,5S)-2-(5-{2-[(2S,4S)-1-{(2S)-2-[(2R,6R)-2,6-dimethyltetrahydro-2H-pyran-4-yl]-2-[(methoxycarbonyl)amino]acetyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate methyl {(2S)-1-[(2S,5S)-2-(5-{2-[(2S,4S)-1-{(2S)-2-[(2R,6R)-2,6-dimethyltetrahydro-2H- pyran-4-yl]-2-[(methoxycarbonyl)amino]acetyl}-4-methylpyrroli-din-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,4S)-1-{(2S)-2-[(2R,6R)-2,6-dimethyltetrahydro-2H-pyran-4-yl]-2-[(methoxycarbonyl)amino]acetyl}-4-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid, and substituting (2S,5S)-1-(tert-butoxycarbonyl)-5-methylpyrrolidine-2-carboxylic acid with (2S,4S)-1-(tert-butoxycarbonyl)-4-methylpyrrolidine-2-carboxylic acid. $^1$H NMR (400 MHz, Methanol-$d_4$) δ 8.63 (d, 1H), 8.19 (d, 1H), 8.11-7.76 (m, 4H), 7.72-7.57 (m, 1H), 5.44-5.26 (m, 2H), 5.23-5.11 (m, 1H), 5.00-4.71 (m, 5H), 4.47 (t, 1H), 4.16 (dt, 3H), 3.81-3.62 (m, 5H), 3.53 (t, 1H), 2.83-2.67 (m, 1H), 2.53 (dd, 2H), 2.33 (dd, 2H), 2.04 (dd, 4H), 1.54 (dd, 2H), 1.52-1.38 (m, 3H), 1.28 (d, 3H), 1.20 (s, 1H), 1.15 (s, 2H), 1.11-0.95 (m, 6H), 0.87 (t, 2H). LCMS-ESI+ calc'd for C49H61N8O8: 890.05. Found: 889.23.

Example AW

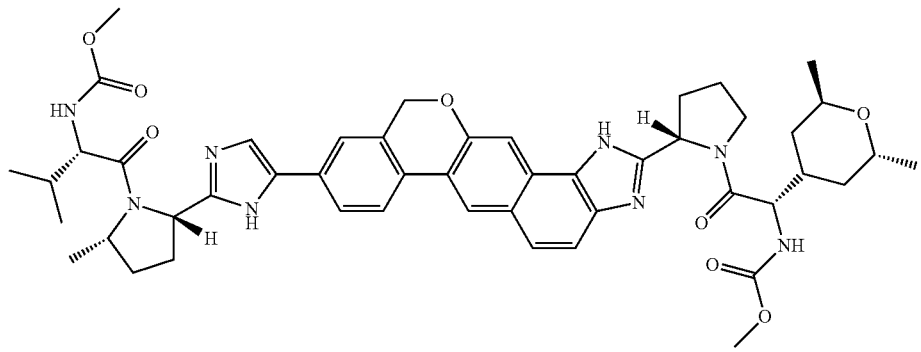

methyl {(2S)-1-[(2S,5S)-2-(5-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate

141 methyl {(2S)-1-[(2S,5S)-2-(5-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid, and substituting (2S,5S)-1-(tert-butoxycarbonyl)-5-methylpyrrolidine-2-carboxylic acid with (S)-1-(tert-butoxycarbonyl)pyrrolidine-2-carboxylic acid. 1H NMR (400 MHz, Methanol-d4) δ 8.65 (s, 1H), 8.21 (d, 1H), 8.08-7.96 (m, 1H), 7.92 (s, 1H), 7.85 (d, 1H), 7.75-7.59 (m, 2H), 5.45-5.38 (m, 1H), 5.33 (s, 1H), 5.23-5.11 (m, 1H), 4.35-4.06 (m, 4H), 4.01-3.92 (m, 1H), 3.82-3.44 (m, 7H), 2.75-2.48 (m, 3H), 2.46-2.09 (m, 6H), 2.07-1.91 (m, 2H), 1.56 (d, 3H), 1.49-1.36 (m, 2H), 1.32-1.21 (m, 2H), 1.15 (d, 3H), 1.10-0.93 (m, 6H), 0.88 (d, 2H). LCMS-ESI+ calc'd for C48H59N8O8: 875.45. Found: 875.29.

Example AX

142 methyl {(2S)-1-[(2S,5S)-2-(5-{2-[(2S,3aS,6aS)-1-{(2S)-2-[(2R,6R)-2,6-dimethyltetrahydro-2H-pyran-4-yl]-2-[(methoxycarbonyl)amino]acetyl}octahydrocyclopenta[b]pyrrol-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate Methyl {(2S)-1-[(2S,5S)-2-(5-{2-[(2S,3aS,6aS)-1-{(2S)-2-[(2R,6R)-2,6-dimethyltetrahydro-2H-pyran-4-yl]-2-[(methoxycarbonyl)amino]acetyl}octahydrocyclopenta[b]pyrrol-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-((S)-2-(methoxycarbonylamino)-3-methylbutanoyl)-5-methylpyrrolidine-2-carboxylic acid, and substituting (2S,5S)-1-(tert-butoxycarbonyl)-5-methylpyrrolidine-2-carboxylic acid with (2S,3aS,6aS)-1-(tert-butoxycarbonyl)octahydrocyclopenta[b]pyrrole-2-carboxylic acid. 1H NMR (400 MHz, Methanol-d4) δ 8.66 (s, 1H), 8.21 (d, 1H), 8.12-7.97 (m, 2H), 7.94 (s, 1H), 7.91-7.78 (m, 1H), 7.74-7.62 (m, 2H), 5.81-5.71 (m, 1H), 5.39-5.26 (m, 3H), 5.23-5.11 (m, 1H), 4.84-4.76 (m, 2H), 4.25 (d, 1H), 4.21-4.06 (m, 2H), 3.81 (s, 1H), 3.74 (s, 1H), 3.67 (d, 4H), 3.63-3.52 (m, 1H), 3.16-3.04 (m, 1H), 2.76-2.64 (m, 1H), 2.61-2.48 (m, 1H), 2.44-2.29 (m, 3H), 2.23 (q, 2H), 2.18-2.08 (m, 2H), 2.07-1.85 (m, 4H), 1.84-1.66 (m, 2H), 1.57 (d, 3H), 1.49-1.36 (m, 2H), 1.29 (t, 1H), 1.27-1.18 (m, 1H), 1.15 (d, 3H), 1.12-1.01 (m, 4H), 0.98 (d, 3H), 0.88 (d, 2H). LCMS-ESI+ calc'd for C51H63N8O8: 915.48. Found: 915.29.

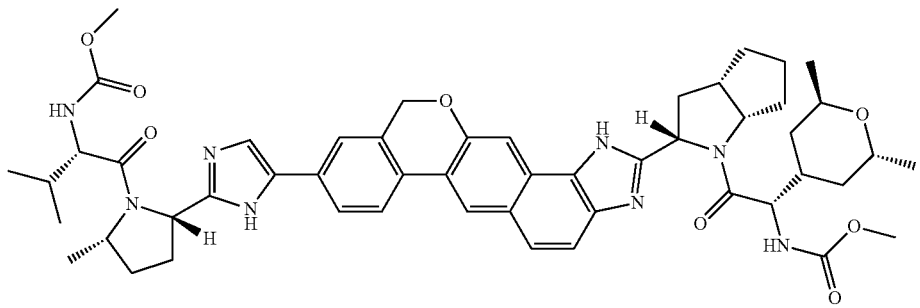

methyl {(2S)-1-[(2S,5S)-2-(5-{2-[(2S,3aS,6aS)-1-{(2S)-2-[(2R,6R)-2,6-dimethyltetrahydro-2H-pyran-4-yl]-2-[(methoxycarbonyl)amino]acetyl}octahydrocyclopenta[b]pyrrol-2-yl]-1,11-dihydroisochromeno[4',3':6,7]naphtho[1,2-d]imidazol-9-yl}-1H-imidazol-2-yl)-5-methylpyrrolidin-1-yl]-3-methyl-1-oxobutan-2-yl}carbamate

Example AY

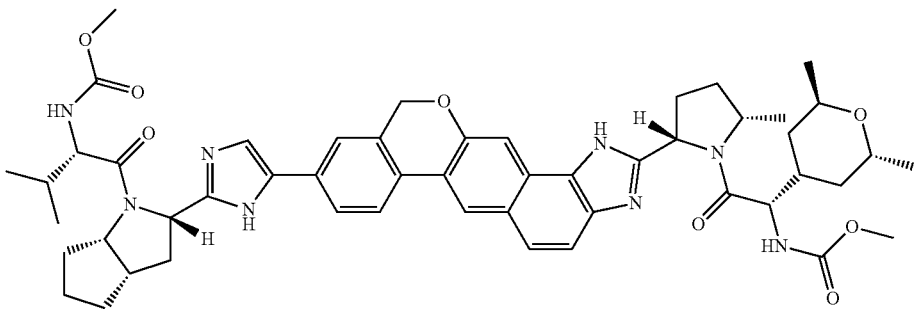

methyl {(2S)-1-[(2S,3aS,6aS)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)hexahydrocyclopenta[b]-pyrrol-1(2H)-yl]-3-methyl-1-oxobutan-2-yl}carbamate methyl {(2S)-1-[(2S,3aS,6aS)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)hexahydrocyclopenta[b]pyrrol-1(2H)-yl]-3-methyl-1-oxobutan-2-yl}carbamate Methyl {(2S)-1-[(2S,3aS,6aS)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)hexahydrocyclopenta[b]pyrrol-1(2H)-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,3aS,6aS)-1-((S)-2-(methoxycarbonylamino)-3-methylbutanoyl)octahydrocyclopenta[b]pyrrole-2-carboxylic acid. 1H NMR (400 MHz, Methanol-d4) δ 8.66 (s, 1H), 8.29-8.18 (m, 1H), 8.10-8.03 (m, 1H), 7.94 (d, 1H), 7.84 (d, 1H), 7.73-7.64 (m, 1H), 5.32 (d, 2H), 5.24-5.13 (m, 1H), 4.18 (dd, 2H), 3.86-3.72 (m, 2H), 3.67 (d, 3H), 3.52 (d, 1H), 3.11-2.97 (m, 1H), 2.72-2.57 (m, 2H), 2.54-2.21 (m, 3H), 2.20-1.80 (m, 7H), 1.79-1.70 (m, 1H), 1.65 (d, 2H), 1.61-1.52 (m, 1H), 1.50-1.36 (m, 1H), 1.36-1.23 (m, 2H), 1.14 (d, 3H), 1.10-1.02 (m, 1H), 1.02-0.88 (m, 6H). LCMS-ESI+ calc'd for C51H63N8O8: 915.48. Found: 915.379.

Examples AZ, BA, BB, BC

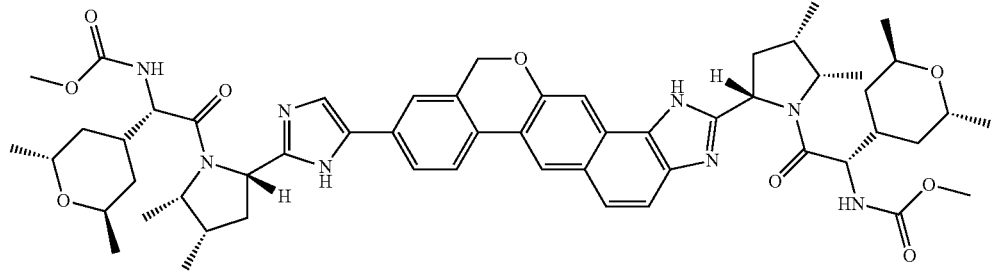

methyl {(1S)-1-[(2R,6R)-2,6-dimethyltetrahydro-2H-pyran-4-yl]-2-[(2S,3S,5S)-5-(5-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazol-9-yl}-1H-imidazol-2-yl)-2,3-dimethylpyrrolidin-1-yl]-2-oxoethyl}carbamate

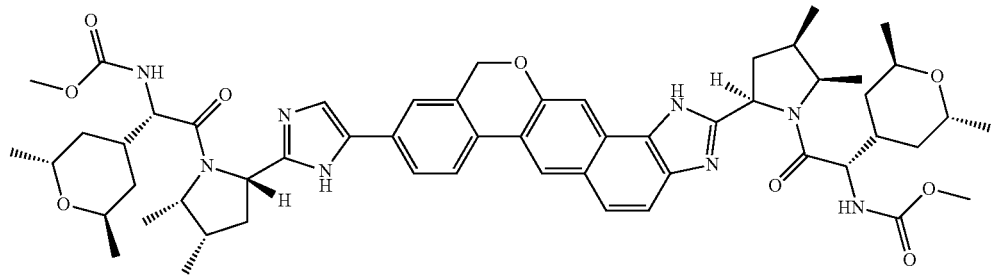

methyl {(1S)-1-[(2R,6R)-2,6-dimethyltetrahydro-2H-pyran-4-yl]-2-[(2R,3R,5R)-5-(9-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1H-imidazol-5-yl}-1,11-dihydroisochromeno[4',3':6,7]naphtho[1,2-d]imidazol-2-yl)-2,3-dimethylpyrrolidin-1-yl]-2-oxoethyl}carbamate -continued

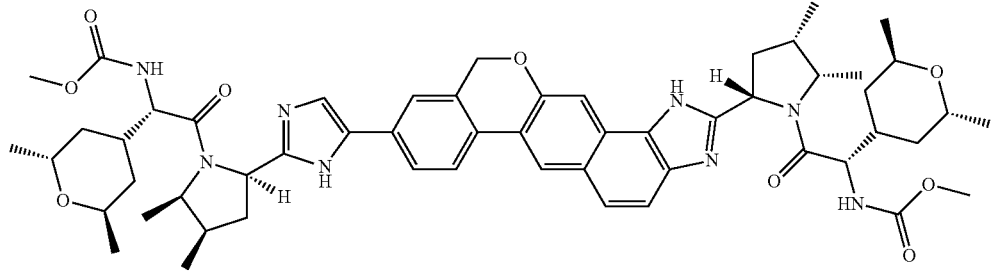

methyl {(1S)-1-[(2R,6R)-2,6-dimethyltetrahydro-2H-pyran-4-yl]-2-[(2R,3R,5R)-
5-(5-{2-[(2S,4S,5S)-1-{(2S)-2-[(2R,6R)-2,6-dimethyltetrahydro-2H-pyran-4-yl]-
2-[(methoxycarbonyl)amino]acetyl}-4,5-dimethylpyrrolidin-2-yl]-1,11-
dihydroisochromeno[4',3':6,7]naphtho[1,2-d]imidazol-9-yl}-1H-imidazol-2-yl)-
2,3-dimethylpyrrolidin-1-yl]-2-oxoethyl}carbamate

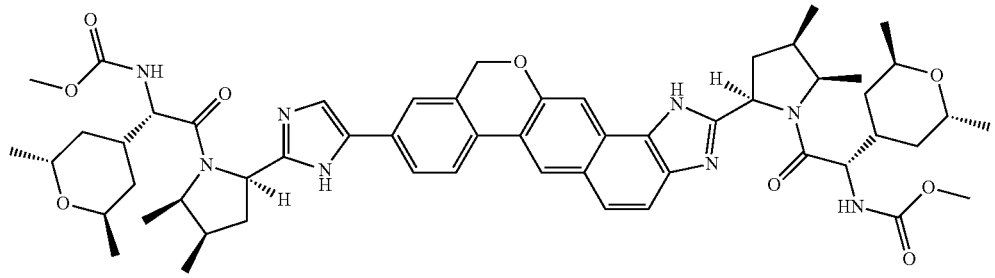

methyl {(1S)-1-[(2R,6R)-2,6-dimethyltetrahydro-2H-pyran-4-yl]-2-[(2R,3R,5R)-
5-(5-{2-[(2R,4R,5R)-1-{(2S)-2-[(2R,6R)-2,6-dimethyltetrahydro-2H-pyran-4-yl]-
2-[(methoxycarbonyl)amino]acetyl}-4,5-dimethylpyrrolidin-2-yl]-1,11-
dihydroisochromeno[4',3':6,7]naphtho[1,2-d]imidazol-9-yl}-1H-imidazol-2-yl)-
2,3-dimethylpyrrolidin-1-yl]-2-oxoethyl}carbamate methyl {(1S)-1-[(2R,6R)-2,6-dimethyltetrahydro-2H-pyran-4-yl]-2-[(2S,3S,5S)-5-(5-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazol-9-yl}-1H-imidazol-2-yl)-2,3-dimethylpyrrolidin-1-yl]-2-oxoethyl}carbamate methyl {(1S)-1-[(2R,6R)-2,6-dimethyltetrahydro-2H-pyran-4-yl]-2-[(2R,3R,5R)-5-(9-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1H-imidazol-5-yl}-1,11-dihydroisochromeno[4',3':6,7]naphtho[1,2-d]imidazol-2-yl)-2,3-dimethylpyrrolidin-1-yl]-2-oxoethyl}carbamate methyl {(1S)-1-[(2R,6R)-2,6-dimethyltetrahydro-2H-pyran-4-yl]-2-[(2R,3R,5R)-5-(5-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazol-9-yl}-1H-imidazol-2-yl)-2,3-dimethylpyrrolidin-1-yl]-2-oxoethyl}carbamate methyl {(1S)-1-[(2R,6R)-2,6-dimethyltetrahydro-2H-pyran-4-yl]-2-[(2R,3R,5R)-5-(5-{2-[(2R,4R,5R)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazol-9-yl}-1H-imidazol-2-yl)-2,3-dimethylpyrrolidin-1-yl]-2-oxoethyl}carbamate Following Example AA, substituting rel-(2S,4S,5S)-1-(tert-butoxycarbonyl)-4,5-dimethylpyrrolidine-2-carboxylic acid for (2S,5S)-1-((2S,3S)-2-(methoxycarbonylamino)-3-methylpentanoyl)-5-methylpyrrolidine-2-carboxylic acid and (2S,5S)-1-(tert-butoxycarbonyl)-5-methylpyrrolidine-2-carboxylic acid, and using two equivalents of (S)-2-((2R,6R)-2,6-dimethyltetrahydro-2H-pyran-4-yl)-2-(methoxycarbonylamino)acetic acid, provided a mixture of four diastereomers. The diastereomers were separated by reverse phase HPLC (Gemini column, 10-45% MeCN/H2O/0.1% TFA).

Example AZ

Methyl {(1S)-1-[(2R,6R)-2,6-dimethyltetrahydro-2H-pyran-4-yl]-2-[(2S,3S,5S)-5-(5-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazol-9-yl}-1H-imidazol-2-yl)-2,3-dimethylpyrrolidin-1-yl]-2-oxoethyl}carbamate. RT=3.757 min (Gemini column, 2-95% MeCN/H2O/0.1% TFA over 8 min). LCMS-ESI+: calc'd for $C_{55}H_{70}N_8O_9$: 986.53 (M+). Found: 987.88 (M+H+). $^1$H NMR (400 MHz, Methanol-$d_4$) δ 8.25 (s, 1H), 7.96-7.78 (m, 1H), 7.76-7.34 (m, 8H), 7.27 (s, 1H), 5.22-5.06 (m, 4H), 5.00 (t, 1H), 4.65-4.44 (m, 2H), 4.17-3.95 (m, 4H), 3.57 (s, 6H), 3.55-3.46 (m, 1H), 3.45-3.33 (m, 1H), 2.50-1.97 (m, 9H), 1.55 (t, 2H), 1.41 (d, 3H), 1.37-1.26 (m, 5H), 1.24-1.13 (m, 1H), 1.13-1.01 (m, 12H), 1.01-0.93 (m, 1H), 0.86 (d, 3H), 0.83-0.74 (m, 5H).

Example BA

Methyl {(1S)-1-[(2R,6R)-2,6-dimethyltetrahydro-2H-pyran-4-yl]-2-[(2R,3R,5R)-5-(9-{2-[(2S,4S,5S)-1-{(2S)-2-

[(2R,6R)-2,6-dimethyltetrahydro-2H-pyran-4-yl]-2-[(methoxycarbonyl)amino]acetyl}-4,5-dimethylpyrrolidin-2-yl]-1H-imidazol-5-yl}-1,11-dihydroisochromeno[4',3': 6,7]naphtho[1,2-d]imidazol-2-yl)-2,3-dimethylpyrrolidin-1-yl]-2-oxoethyl}carbamate. RT=3.899 min (Gemini column, 2-95% MeCN/H2O/0.1% TFA over 8 min). LCMS-ESI+: calc'd for C55H70N8O9: 986.53 (M+). Found: 987.95 (M+H+). ¹H NMR (400 MHz, Methanol-d4) δ 8.43-8.28 (m, 1H), 8.05-7.88 (m, 1H), 7.88-7.42 (m, 6H), 7.39-7.25 (m, 1H), 5.31-5.01 (m, 4H), 4.70-4.55 (m, 1H), 4.46-4.18 (m, 2H), 4.18-4.05 (m, 2H), 4.04-3.94 (m, 0H), 3.85-3.71 (m, 1H), 3.65 (s, 5H), 3.52-3.38 (m, 1H), 2.63-1.98 (m, 9H), 1.75-1.50 (m, 3H), 1.47 (d, 3H), 1.44-1.21 (m, 6H), 1.18-0.99 (m, 16H), 0.96-0.87 (m, 4H), 0.87-0.82 (m, 3H), 0.65 (d, J=6.1 Hz, 1H).

9-yl}-1H-imidazol-2-yl)-2,3-dimethylpyrrolidin-1-yl]-2-oxoethyl}carbamate. RT=4.076 min (Gemini column, 2-95% MeCN/H2O/0.1% TFA over 8 min). LCMS-ESI+: calc'd for C55H70N8O9: 986.53 (M+). Found: 987.91 (M+H+). ¹H NMR (400 MHz, Methanol-d₄) δ 8.22-8.08 (m, 1H), 7.81-7.67 (m, 1H), 7.65-7.17 (m, 5H), 7.10 (s, 1H), 5.19-5.05 (m, 1H), 5.04-4.80 (m, 3H), 4.30-3.90 (m, 6H), 3.63-3.46 (m, 4H), 3.40 (s, 5H), 2.55-1.60 (m, 10H), 1.55-1.25 (m, 4H), 1.21-0.95 (m, 12H), 0.95-0.74 (m, 14H), 0.56 (d, 2H), 0.49-0.34 (m, 1H), 0.05-0.04 (m, 1H).

Example BD

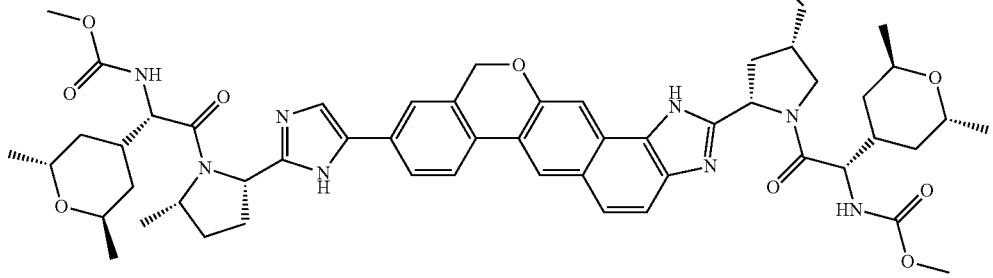

methyl {(1S)-1-[(2R,6R)-2,6-dimethyltetrahydro-2H-pyran-4-yl]-2-[(2S,5S)-2-(5-{2-[(2S,4S)-1-{(2S)-2-[(2R,6R)-2,6-dimethyltetrahydro-2H-pyran-4-yl]-2-[(methoxycarbonyl)amino]acetyl}-4-methylmethylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate

Example BB

Methyl {(1S)-1-[(2R,6R)-2,6-dimethyltetrahydro-2H-pyran-4-yl]-2-[(2R,3R,5R)-5-(5-{2-[(2S,4S,5S)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazol-9-yl}-1H-imidazol-2-yl)-2,3-dimethylpyrrolidin-1-yl]-2-oxoethyl}carbamate. RT=3.940 min (Gemini column, 2-95% MeCN/H2O/0.1% TFA over 8 min). LCMS-ESI+: calc'd for C55H70N8O9: 986.53 (M+). Found: 987.86 (M+H+). ¹H NMR (400 MHz, Methanol-d₄) δ 8.23-8.03 (m, 1H), 7.79-7.64 (m, 2H), 7.59-7.20 (m, 6H), 7.15-7.02 (m, 1H), 5.04-4.87 (m, 3H), 4.83 (t, 1H), 4.43-4.27 (m, 1H), 4.27-3.76 (m, 5H), 3.63-3.46 (m, 3H), 3.45-3.36 (m, 5H), 2.55-1.68 (m, 10H), 1.56-1.27 (m, 3H), 1.23 (d, J=6.8 Hz, 1H), 1.20-1.11 (m, 5H), 1.08 (t, J=7.1 Hz, 1H), 1.04-0.73 (m, 18H), 0.73-0.51 (m, 5H), 0.01 (d, J=6.0 Hz, 1H).

Example BC

Methyl {(1S)-1-[(2R,6R)-2,6-dimethyltetrahydro-2H-pyran-4-yl]-2-[(2R,3R,5R)-5-(5-{2-[(2R,4R,5R)-1-{(2S)-2-[(2R,6R)-2,6-dimethyltetrahydro-2H-pyran-4-yl]-2-[(methoxycarbonyl)amino]acetyl}-4,5-dimethylpyrrolidin-2-yl]-1,11-dihydroisochromeno[4',3':6,7]naphtho[1,2-d]imidazolmethyl {(1S)-1-[(2R,6R)-2,6-dimethyltetrahydro-2H-pyran-4-yl]-2-[(2S,5S)-2-(5-{2-[(2S,4S)-1-{(2S)-2-[(2R,6R)-2,6-dimethyltetrahydro-2H-pyran-4-yl]-2-[(methoxycarbonyl)amino]acetyl}-4-methoxymethylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate Methyl {(1S)-1-[(2R,6R)-2,6-dimethyltetrahydro-2H-pyran-4-yl]-2-[(2S,5S)-2-(5-{2-[(2S,4S)-1-{(2S)-2-[(2R,6R)-2,6-dimethyltetrahydro-2H-pyran-4-yl]-2-[(methoxycarbonyl)amino]acetyl}-4-methoxymethylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid and (2S,5S)-1-(tert-butoxycarbonyl)-5-methylpyrrolidine-2-carboxylic acid with (2S,4S)-1-(tert-butoxycarbonyl)-4-(methoxymethyl)pyrrolidine-2-carboxylic acid ¹H NMR (400 MHz, dmso) δ 8.71 (s, 1H), 8.18 (m, 1H), 7.95 (m, 4H), 7.80-7.54 (m, 3H), 7.45 (m, 1H), 5.34-5.14 (m, 3H), 5.05-4.92 (m, 1H), 4.62 (s, 1H), 4.35-3.03 (m, 13H), 2.66 (s, 2H), 2.50 (m, 2H), 2.39-1.72 (m, 9H), 1.55-0.67 (m, 28H). MS (ESI) m/z 989.41 [M+H]⁺.

Example BE

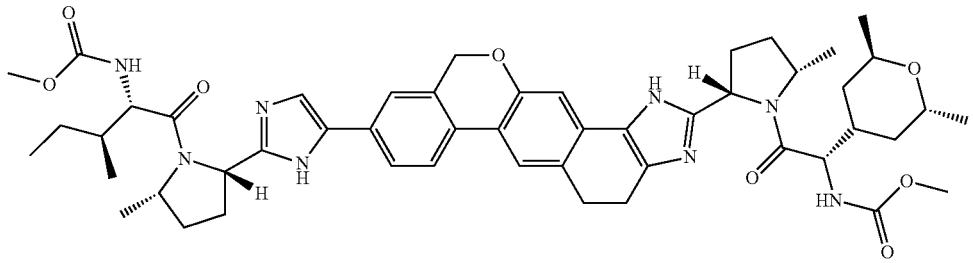

methyl {(2S,3S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,4,5,11-tetrahydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate methyl {(2S,3S)-1-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,4,5,11-tetrahydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate Methyl {(2S,3S)-1-[(2S,5S)-2-(5-{24(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,4,5,11-tetrahydroisochromeno[4',3':6,7]naphtho[1,2-d]imidazol-9-yl}-1H-imidazol-2-yl)-5-methylpyrrolidin-1-yl]-3-methyl-1-oxopentan-2-yl}carbamate was synthesized in a similar manner as example AA omitting the oxidation with MnO$_2$. $^1$H NMR (400 MHz, dmso) δ 7.84 (m, 4H), 7.62 (m, 2H), 7.53 (m, 1H), 7.25 (s, 1H), 5.15 (s, 2H), 5.02-4.88 (m, 2H), 4.62 (s, 2H), 4.14-3.24 (m, 16H), 3.06 (s, 2H), 2.88 (s, 2H), 2.21 (m, 8H), 1.82 (s, 2H), 1.67 (s, 1H), 1.44 (m, 8H), 1.30-0.95 (m, 8H), 0.91 (m, 3H), 0.78 (m, 5H), 0.64 (m, 3H). MS (ESI) m/z 905.78 [M+H]$^+$.

methyl {(1S)-1-[(2R,6R)-2,6-dimethyltetrahydro-2H-pyran-4-yl]-2-[(2S,5S)-2-(9-[2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidin-1-yl]-2-oxoethyl}carbamate Methyl {(1S)-1-[(2R,6R)-2,6-dimethyltetrahydro-2H-pyran-4-yl]-2-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidin-1-yl]-2-oxoethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,4S)-1-(tert-butoxycarbonyl)-5-methylpyrrolidine-2-carboxylic acid and omitting the oxidation with MnO$_2$. $^1$H NMR (400 MHz, dmso) δ 8.05-7.75 (m, 4H), 7.73-7.47 (m, 3H), 7.31 (m, 1H), 5.15 (s, 2H), 4.96 (m, 2H), 4.61 (s, 2H), 4.15-3.15 (m, 18H), 3.06 (s, 2H), 2.99-2.75 (m, 3H), 2.17 (m, 8H), 1.82 (m, 2H), 1.53-1.32 (m, 6H), 1.30-1.17 (m, 2H), 1.14-0.87 (m, 11H), 0.85-0.69 (m, 2H). MS (ESI) m/z 961.54 [M+H]$^+$.

Example BF

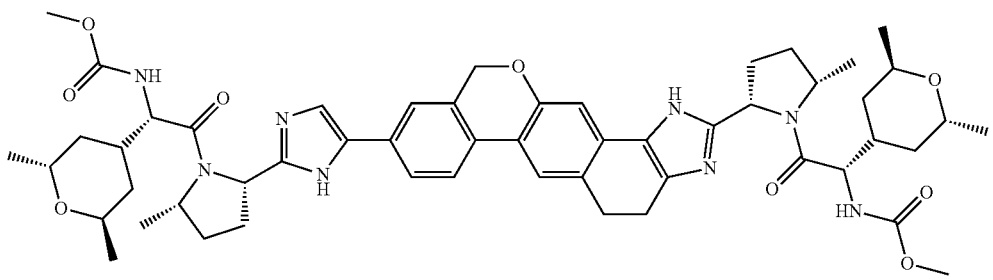

methyl {(1S)-1-[(2R,6R)-2,6-dimethyltetrahydro-2H-pyran-4-yl]-2-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,4,5,11-tetrahydroisochromeno[4',3':6,7]naphtho[1,2-d]imidazol-2-yl)-5-methylpyrrolidin-1-yl]-2-oxoethyl}carbamate

Example BG

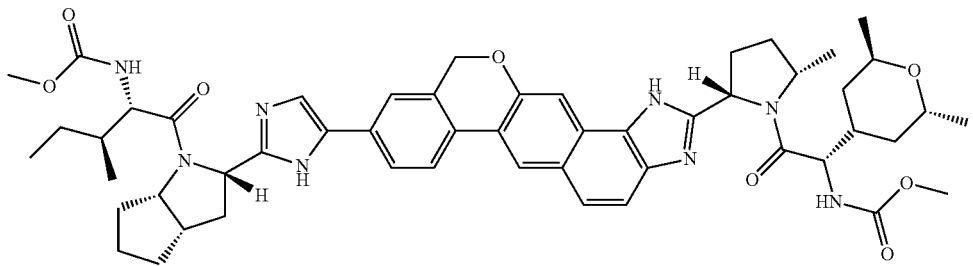

methyl {(2S,3S)-1-[(2S,3aS,6aS)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)hexahydrocyclopenta[b]pyrrol-1(2H)-yl]-3-methyl-1-oxopentan-2-yl}carbamate methyl {(2S,3S)-1-[(2S,3aS,6aS)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)hexahydrocyclopenta[b]pyrrol-1(2H)-yl]-3-methyl-1-oxopentan-2-yl}carbamate Methyl {(2S,3S)-1-[(2S,3aS,6aS)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)hexahydrocyclopenta[b]pyrrol-1(2H)-yl]-3-methyl-1-oxopentan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,3aS,6aS)-1-((2S,3S)-2-(methoxycarbonylamino)-3-methylpentanoyl)octahydrocyclopenta[b]pyrrole-2-carboxylic acid. $^1$H NMR (400 MHz, dmso) δ 8.62 (s, 1H), 8.18 (s, 2H), 7.90-7.64 (m, 3H), 7.63-7.39 (m, 2H), 5.24 (s, 2H), 5.13 (s, 1H), 5.02 (s, 1H), 4.69 (s, 2H), 4.13-3.85 (m, 3H), 3.47 (m, 10H), 2.87 (s, 2H), 2.42 (m, 2H), 2.10 (s, 5H), 1.75 (m, 5H), 1.51 (m, 7H), 1.31-0.94 (m, 7H), 0.92-0.64 (m, 9H). MS (ESI) m/z 929.46 [M+H]$^+$.

Example BH methyl {(1S)-1-[(2R,6R)-2,6-dimethyltetrahydro-2H-pyran-4-yl]-2-[(2S,5S)-2-(9-{2-[(2S,4S)-1-{(2S)-2-[(2R,6R)-2,6-dimethyltetrahydro-2H-pyran-4-yl]-2-[(methoxycarbonyl)amino]acetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-2-oxoethyl}carbamate Methyl {(1S)-1-[(2R,6R)-2,6-dimethyltetrahydro-2H-pyran-4-yl]-2-[(2S,5S)-2-(9-{2-[(2S,4S)-1-{(2S)-2-[(2R,6R)-2,6-dimethyltetrahydro-2H-pyran-4-yl]-2-[(methoxycarbonyl)amino]acetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-2-oxoethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,4S)-1-(tert-butoxycarbonyl)-4-(methoxymethyl)pyrrolidine-2-carboxylic acid. $^1$H NMR (400 MHz, cdcl$_3$) δ 8.69 (s, 1H), 8.28-8.09 (m, 2H), 8.00-7.75 (m, 3H), 7.62 m, 2H), 7.50 (m, 1H), 5.27 (s, 2H), 5.14 (1H), 4.73 (s, 1H), 4.33-3.25 (m, 20H), 2.66 (s, 1H), 2.58-2.28 (m, 8H), 2.25-1.79 (m, 4H), 1.65-0.66 (m, 21H). MS (ESI) m/z 989.65 [M+H]$^+$.

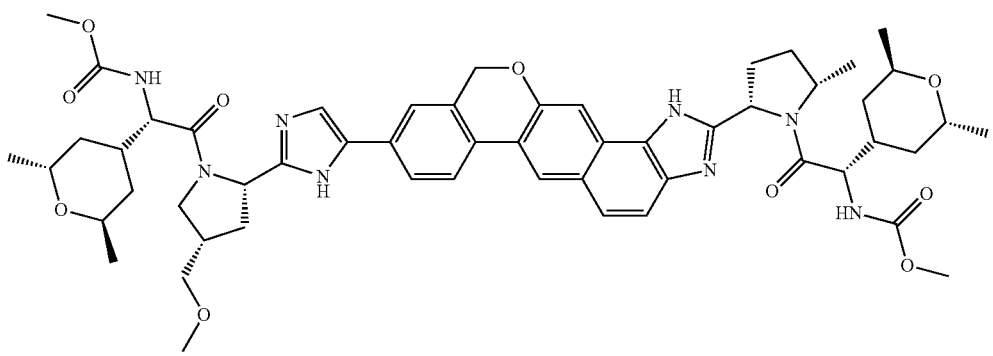

methyl {(1S)-1-[(2R,6R)-2,6-dimethyltetrahydro-2H-pyran-4-yl]-2-[(2S,5S)-2-(9-{2-[(2S,4S)-1-{(2S)-2-[(2R,6R)-2,6-dimethyltetrahydro-2H-pyran-4-yl]-2-[(methoxycarbonyl)amino]acetyl}-4-(methoxymethyl)pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-2-oxoethyl}carbamate

Example BI

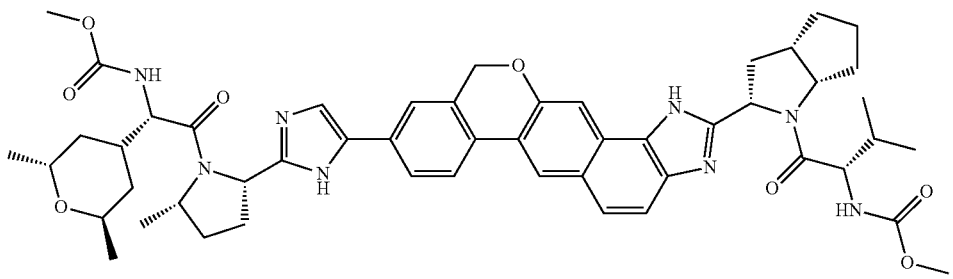

methyl {(2S)-1-[(2S,3aS,6aS)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)hexahydrocyclopenta[b]pyrrol-1(2H)-yl]-3-methyl-1-oxobutan-2-yl}carbamate methyl {(2S)-1-[(2S,3aS,6aS)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)hexahydrocyclopenta[b]pyrrol-1(2H)-yl]-3-methyl-1-oxobutan-2-yl}carbamate Methyl {(2S)-1-[(2S,3aS,6aS)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)hexahydrocyclopenta[b]pyrrol-1(2H)-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid and (2S,5S)-1-(tert-butoxycarbonyl)-5-methylpyrrolidine-2-carboxylic acid with (2S,3aS,6aS)-1-((S)-2-(methoxycarbonylamino)-3 methylbutanoyl) octahydrocyclopenta[b]pyrrole-2-carboxylic acid. $^1$H NMR (400 MHz, dmso) δ 8.67 (s, 1H), 7.72 (m, 8H), 5.33-5.17 (m, 3H), 5.00 (m, 1H), 4.77 (s, 1H), 4.62 (s, 1H), 4.17-3.86 (m, 5H), 3.49 (m, 10H), 2.89 (s, 1H), 2.56-1.70 (m, 7H), 1.47 (m, 6H), 1.30-0.97 (m, 6H), 0.90 (s, 4H), 0.81 (m, 8H). MS (ESI) m/z 915.37 [M+H]$^+$.

methyl {(2S)-1-[(2S,5S)-2-(9-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate Methyl {(2S)-1-[(2S,5S)-2-(9-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (2S,5S)-1-(tert-butoxycarbonyl)-5-methylpyrrolidine-2-carboxylic acid and (2S,5S)-1-(tert-butoxycarbonyl)-5-methylpyrrolidine-2-carboxylic acid with (2S,5S)-1-(S)-2-(methoxycarbonylamino)-3-methylbutanoyl)-5-methylpyrrolidine-2-carboxylic acid $^1$H NMR (400 MHz, dmso) δ 8.67 (s, 1H), 8.19 (m, 1H), 8.03 (m, 2H), 7.91-7.68 (m, 3H), 7.68-7.38 (m, 3H), 5.26 (s, 2H), 5.14 (m, 2H), 4.70 (s, 1H), 4.20-3.23 (m, 14H), 2.37 (s, 2H), 2.22-1.71 (m, 6H), 1.49 (m, 3H), 1.41-0.97 (m, 7H), 0.97-0.78 (m, 8H), 0.72 (m, 3H). MS (ESI) m/z 875.30 [M+H]$^+$.

Example BJ

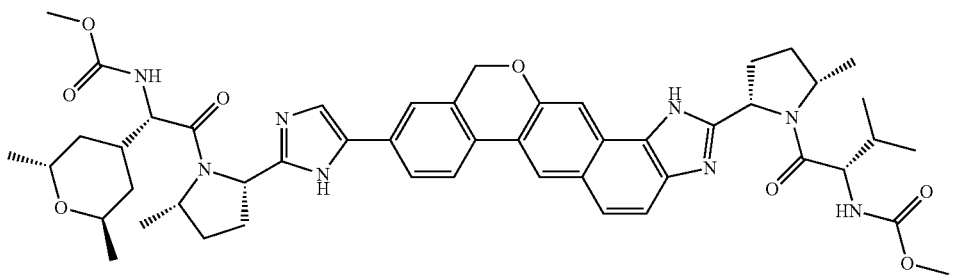

methyl {(2S)-1-[(2S,5S)-2-(9-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxobutan-2-yl}carbamate

Example BK

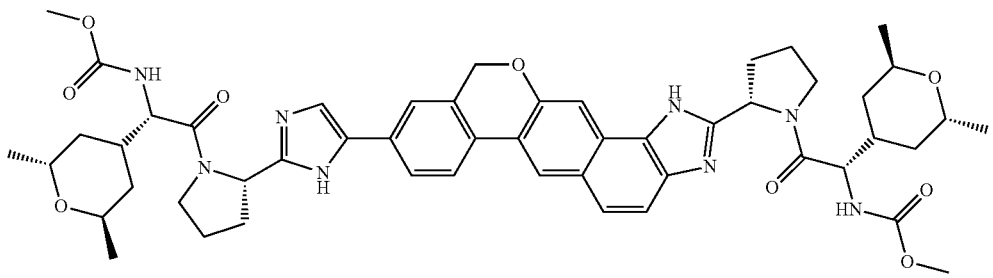

methyl {(1S)-1-[(2R,6R)-2,6-dimethyltetrahydro-2H-pyran-4-yl]-2-[(2S)-2-(5-{2-[(2S)-1-{(2S)-2-[(2R,6R)-2,6-dimethyltetrahydro-2H-pyran-4-yl]-2-[(methoxycarbonyl)amino]acetyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxoethyl}carbamate methyl {(1S)-1-[(2R,6R)-2,6-dimethyltetrahydro-2H-pyran-4-yl]-2-[(2S)-2-(5-{2-[(2S)-1-{(2S)-2-[(2R,6R)-2,6-dimethyltetrahydro-2H-pyran-4-yl]-2-[(methoxy carbonyl)amino]acetyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxoethyl}carbamate Methyl {(1S)-1-[(2R,6R)-2,6-dimethyltetrahydro-2H-pyran-4-yl]-2-[(2S)-2-(5-{2-[(2S)-1-{(2S)-2-[(2R,6R)-2,6-dimethyltetrahydro-2H-pyran-4-yl]-2-[(methoxy carbonyl)amino]acetyl}pyrrolidin-2-yl]-1,11-dihydroisochromeno[4',3':6,7]naphtho[1,2-d]imidazol-9-yl}-1H-imidazol-2-yl)pyrrolidin-1-yl]-2-oxoethyl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with (S)-1-(tert-butoxycarbonyl)pyrrolidine-2-carboxylic acid and (2S,5S)-1-(tert-butoxycarbonyl)-5-methylpyrrolidine-2-carboxylic acid with (S)-1-(tert-butoxycarbonyl)pyrrolidine-2-carboxylic acid. ¹H NMR (400 MHz, dmso) δ 8.69 (s, 1H), 8.19 (m, 1H), 8.08 (s, 1H), 7.86 (m, 3H), 7.73 (s, 1H), 7.62 (m, 1H), 7.47 (m, 1H), 5.26 (s, 3H), 5.10 (m, 1H), 4.12-3.24 (m, 18H), 2.37 (s, 2H), 2.31-1.89 (m, 8H), 1.31 (m, 6H), 1.06 (m, 7H), 0.96-0.76 (m, 8H). MS (ESI) m/z 931.86 [M+H]⁺.

methyl {(2S,3S)-1-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxopentan-2-yl}carbamate Methyl {(2S,3S)-1-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxopentan-2-yl}carbamate was synthesized in a similar manner as example AA substituting (2S,5S)-1-((2S,3S)-2-(methoxycarbonylamino)-3-methylpentanoyl)-5-methylpyrrolidine-2-carboxylic acid with ((2S,5S)-1-(tert-butoxycarbonyl)-5-methylpyrrolidine-2-carboxylic acid and (2S,5S)-1-(tert-butoxycarbonyl)-5-methylpyrrolidine-2-carboxylic acid with (2S,5S)-1-((2S,3S)-2-(methoxycarbonylamino)-3-methylpentanoyl)-5-methylpyrrolidine-2-carboxylic acid. ¹H NMR (400 MHz, dmso) δ 8.66 (s, 1H), 8.18 (m, 1H), 8.12-7.71 (m, 5H), 7.58 (m, 2H), 5.27 (s, 2H), 5.15 (m, 1H), 5.06-4.93 (m, 1H), 4.67 (m, 2H), 4.22-3.29 (m, 11H), 2.23 (m, 7H), 1.83 (s, 2H), 1.65 (s, 1H), 1.47 (m, 8H), 1.29-0.98 (m, 7H), 0.95-0.70 (m, 8H), 0.66 (m, 3H). MS (ESI) m/z 903.87 [M+H]⁺.

Example BL

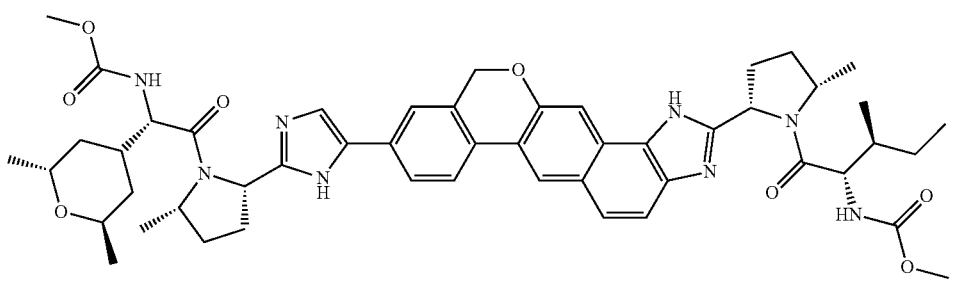

methyl {(2S,3S)-1-[(2S,5S)-2-(9-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1H-imidazol-5-yl}-1,11-dihydroisochromeno[4',3':6,7]naphtho[1,2-d]imidazol-2-yl)-5-methylpyrrolidin-1-yl]-3-methyl-1-oxopentan-2-yl}carbamate

Example BM

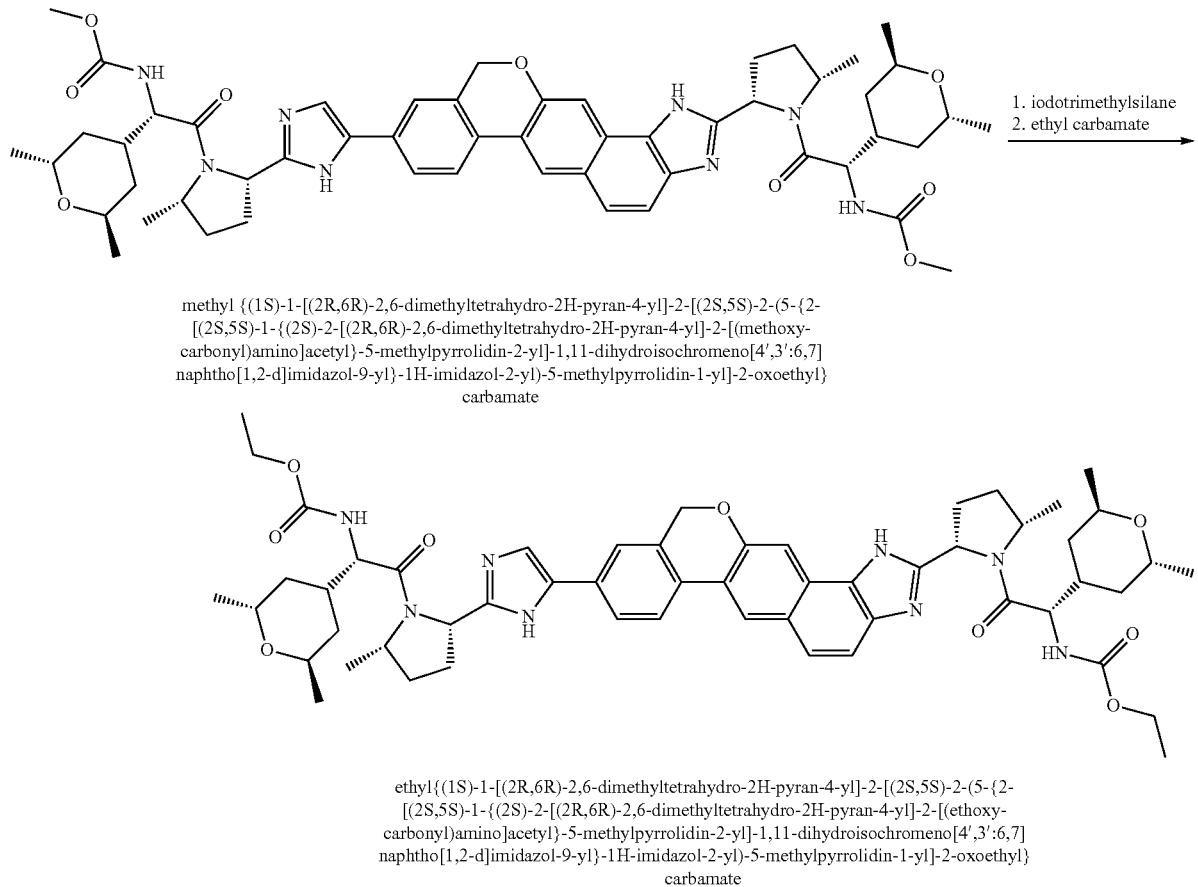

methyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(methoxy-carbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl} carbamate ethyl{(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(ethoxy-carbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl} carbamate Ethyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(ethoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate Iodotrimethylsilane (1.14 ml, 8.03 mmol) is added to a solution of methyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(methoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate (770 mg, 0.8 mmol) in Dichloromethane (10 ml), and the mixture is then refluxed for 3 hours. After cooling to room temperature the mixture was concentrated; dissolved in ethyl acetate and extracted with 2×7 ml of 1N hydrochloric acid solution. The aqueous phases are combined, cooled and then basified by addition of 5N sodium hydroxide. The basic aqueous phase is extracted with ethyl acetate 3×10 ml. The organic phases were combined, dried over $Na_2SO_4$ and concentrated under vacuum, the product 667 mg (98.5%) was treated with sodium hydroxide (66.25 mg, 1.66 mmol) in Water (7 ml). The mixture was cooled in an ice bath and ethyl chloroformate (0.16 ml, 1.66 mmol) was added, the reaction mixture was stirred at 0° C. for 30 min, extracted with 2×10 ml ethyl acetate. The combined organic layers were dried over $Na_2SO_4$ and concentrated. The residue was purified by reverse phase HPLC (Gemini column, 10-46% $MeCN/H_2O/0.1\%$ TFA). The desired fractions were combined, lyophilized to provide ethyl {(1S)-1-[(2R,6R)-2,6-dimethyltetrahydro-2H-pyran-4-yl]-2-[(2S,5S)-2-(5-{2-[(2S,5S)-1-{(2S)-2-[(2R,6R)-2,6-dimethyltetrahydro-2H-pyran-4-yl]-2-[(ethoxycarbonyl)amino]acetyl}-5-methylpyrrolidin-2-yl]-1,11-dihydroisochromeno[4',3':6,7]naphtho[1,2-d]imidazol-9-yl}-1H-imidazol-2-yl)-5-methylpyrrolidin-1-yl]-2-oxoethyl}carbamate. $^1H$ NMR (400 MHz, dmso) δ 8.62 (s, 1H), 8.26-7.33 (m, 9H), 5.24 (s, 2H), 5.13 (s, 1H), 4.98 (s, 1H), 4.80-4.55 (m, 2H), 4.30-3.23 (m, 9H), 2.19 (m, 9H), 1.83 (s, 2H), 1.48 (m, 10H), 1.32-0.69 (m, 24H). MS (ESI) m/z 987.89 [M+H]$^+$.

Biological Assays

Effect of Serum Proteins on Replicon Potency:

Replicon assays are conducted in normal cell culture medium (DMEM+10% FBS) supplemented with physiologic concentrations of human serum albumin (40 mg/mL) or α-acid glycoprotein (1 mg/mL). $EC_{50}$s in the presence of human serum proteins are compared to the $EC_{50}$ in normal medium to determine the fold shift in potency.

MT-4 Cell Cytotoxicity:

MT4 cells are treated with serial dilutions of compounds for a five day period. Cell viability is measured at the end of the treatment period using the Promega CellTiter-Glo assay and non-linear regression is performed to calculate $CC_{50}$.

Compound Concentration Associated with Cells at $EC_{50}$:

Huh-luc cultures are incubated with compound at concentrations equal to $EC_{50}$. At multiple time points (0-72 hours), cells are washed 2× with cold medium and extracted with 85% acetonitrile; a sample of the media at each time-point will also be extracted. Cell and media extracts are analyzed by LC/MS/MS to determine the Molar concentration of compounds in each fraction. Representative compounds of the disclosure have shown activity.

Solubility and Stability:

Solubility is determined by taking an aliquot of 10 mM DMSO stock solution and preparing the compound at a final concentration of 100 μM in the test media solutions (PBS, pH 7.4 and 0.1 N HCl, pH 1.5) with a total DMSO concentration of 1%. The test media solutions are incubated at room temperature with shaking for 1 hr. The solutions will then be centrifuged and the recovered supernatants are assayed on the HPLC/UV. Solubility will be calculated by comparing the amount of compound detected in the defined test solution compared to the amount detected in DMSO at the same concentration. Stability of compounds after an 1 hour incubation with PBS at 37° C. will also be determined.

Stability in Cryopreserved Human, Dog, and Rat Hepatocytes:

Each compound is incubated for up to 1 hour in hepatocyte suspensions (100 μl, 80,000° Cells per well) at 37° C. Cryopreserved hepatocytes are reconstituted in the serum-free incubation medium. The suspension is transferred into 96-well plates (50 μL/well). The compounds are diluted to 2 μM in incubation medium and then are added to hepatocyte suspensions to start the incubation. Samples are taken at 0, 10, 30 and 60 minutes after the start of incubation and reaction will be quenched with a mixture consisting of 0.3% formic acid in 90% acetonitrile/10% water. The concentration of the compound in each sample is analyzed using LC/MS/MS. The disappearance half-life of the compound in hepatocyte suspension is determined by fitting the concentration-time data with a monophasic exponential equation. The data will also be scaled up to represent intrinsic hepatic clearance and/or total hepatic clearance.

Stability in Hepatic S9 Fraction from Human, Dog, and Rat:

Each compound is incubated for up to 1 hour in S9 suspension (500 μA, 3 mg protein/mL) at 37° C. (n=3). The compounds are added to the S9 suspension to start the incubation. Samples are taken at 0, 10, 30, and 60 minutes after the start of incubation. The concentration of the compound in each sample is analyzed using LC/MS/MS. The disappearance half-life of the compound in S9 suspension is determined by fitting the concentration-time data with a monophasic exponential equation.

Caco-2 Permeability:

Compounds are assayed via a contract service (Absorption Systems, Exton, Pa.). Compounds are provided to the contractor in a blinded manner. Both forward (A-to-B) and reverse (B-to-A) permeability will be measured. Caco-2 monolayers are grown to confluence on collagen-coated, microporous, polycarbonate membranes in 12-well Costar TRANSWELL® plates. The compounds are dosed on the apical side for forward permeability (A-to-B), and are dosed on the basolateral side for reverse permeability (B-to-A). The cells are incubated at 37° C. with 5% $CO_2$ in a humidified incubator. At the beginning of incubation and at 1 hr and 2 hr after incubation, a 200-μL aliquot is taken from the receiver chamber and replaced with fresh assay buffer. The concentration of the compound in each sample is determined with LC/MS/MS. The apparent permeability, Papp, is calculated.

Plasma Protein Binding:

Plasma protein binding is measured by equilibrium dialysis. Each compound is spiked into blank plasma at a final concentration of 2 μM. The spiked plasma and phosphate buffer is placed into opposite sides of the assembled dialysis cells, which will then be rotated slowly in a 37° C. water bath. At the end of the incubation, the concentration of the compound in plasma and phosphate buffer is determined. The percent unbound is calculated using the following equation:

$$\% \text{ Unbound} = 100 \cdot \left(\frac{C_f}{C_b + C_f}\right)$$

Where $C_f$ and $C_b$ are free and bound concentrations determined as the post-dialysis buffer and plasma concentrations, respectively.

CYP450 Profiling:

Each compound is incubated with each of 5 recombinant human CYP450 enzymes, including CYP1A2, CYP2C9, CYP3A4, CYP2D6 and CYP2C19 in the presence and absence of NADPH. Serial samples will be taken from the incubation mixture at the beginning of the incubation and at 5, 15, 30, 45 and 60 minutes after the start of the incubation. The concentration of the compound in the incubation mixture is determined by LC/MS/MS. The percentage of the compound remaining after incubation at each time point is calculated by comparing with the sampling at the start of incubation.

Stability in Rat, Dog, Monkey and Human Plasma:

Compounds will be incubated for up to 2 hours in plasma (rat, dog, monkey, or human) at 37° C. Compounds are added to the plasma at final concentrations of 1 and 10 μg/mL. Aliquots are taken at 0, 5, 15, 30, 60, and 120 minutes after adding the compound. Concentration of compounds and major metabolites at each time point are measured by LC/MS/MS.

Evaluation of Cell-Based Anti-HCV Activity:

Antiviral potency ($EC_{50}$) was determined using a *Renilla luciferase* (RLuc)-based HCV replicon reporter assay. To perform the assay for genotype 1 and 2a JFH-1, stable HCV 1a RLuc replicon cells (harboring a dicistronic genotype 1a H77 replicon that encodes a RLuc reporter), stable HCV 1b RLuc replicon cells (harboring a dicistronic genotype 1b Con1 replicon that encodes a RLuc reporter), or stable HCV 2a JFH-1 Rluc replicon cells (harboring a dicistronic genotype 2a JFH-1 replicon that encodes a RLuc reporter; with L31 present in NS5A) were dispensed into 384-well plates for $EC_{50}$ assays. To perform the assay for genotype 2a (with M31 present in NS5A) or 2b, NS5A chimeric genotype 2a JFH-1 replicons that encodes a RLuc-Neo reporter and either genotype 2a J6 strain NS5A gene or genotype 2b MD2b-1 strain NS5A gene (both with M31 present) respectively, were either transiently transfected (t) into Huh-Lunet cells or were established as stably replicating replicon cells (s) is provided. Either cells were dispensed into 384-well plates for $EC_{50}$ assays. To perform the assay for genotype 3 and 4, NS5A chimeric genotype 1b Con1 replicons that encodes a Pi-RLuc reporter and either genotype 3a S52 strain NS5A gene or genotype 4a ED43 strain NS5A gene respectively, were transiently transfected (t) into Huh-Lunet cells, which were subsequently dispensed into 384-well plates. Compounds were dissolved in DMSO at a concentration of 10 mM and diluted in DMSO either manually or using an automated pipeting instrument. Serially 3-fold diluted compounds were either manually mixed with cell culture media and added to the seeded cells or directly added to the cells using an automated instrument. DMSO was used as a negative (solvent; no inhibition) control, and the protease inhibitor ITMN-191 was included at a concentration >100×$EC_{50}$ as a positive control. 72 hours later, cells were lysed and *Renilla luciferase* activity quantified as recommended by the manufacturer (Promega-Madison, Wis.). Non-linear regression was performed to calculate $EC_{50}$ values.

To determine the antiviral potency ($EC_{50}$) against resistance mutants, resistance mutations, including M28T, Q30R, Q30H, Q30E, L31M, Y93C, Y93H, and Y93N in genotype 1a NS5A, Y93H and L31V/Y93H in genotype 1b NS5A, and Y93H for in genotype 3a NS5A, were introduced individually into either 1a Pi-Rluc or 1b Pi-Rluc replicons by site directed mutagenesis. Replicon RNA of each resistant mutant was transiently transfected into Huh-7-derived cured-51 cells and antiviral potency was determined on these transfected cells as described above.

IV and PO Single Dose Pharmacokinetic Studies in SD Rats:

The pharmacokinetics of selected compounds was characterized in male Sprague-Dawley (SD) rats (250-300 g). In this study, two groups of naïve purebred SD rats (N=3 per group, fasted over night) received the selected compound either as an intravenous (IV) infusion (1 mg/kg over 30 minutes) via the jugular vein or by oral gavage (2 mg/kg). The intravenous (IV) dosing vehicle was 5% ethanol, 35% polyethylene glycol 400 (PEG 400) and 60% water pH 2.0. The oral dosing vehicle was 5% ethanol, 55% PEG 400 and 40% citrate buffer pH 2.2.

Serial blood samples (approximately 0.3 mL each) were collected from jugular vein or other suitable vein at specified time points. For the IV infusion group, the blood samples were collected predose and at 0.25, 0.48, 0.58, 0.75, 1.5, 3, 6, 8, 12 and 24 hours after the start of infusion. For the oral group, the blood samples were collected predose and at 0.25, 0.50, 1, 2, 4, 6, 8, 12 and 24 hours after dosing. The blood samples were collected into Vacutainer™ tubes containing EDTA-$K_3$ as the anti-coagulant and were centrifuged at approximately 4° C. to obtain plasma. The plasma samples were stored at −20° C. until analysis by LC/MS/MS.

A bioanalytical method utilizing high performance liquid chromatography coupled to tandem mass spectrometry (LC/MS/MS) was developed for analysis of the selected compound in rat plasma. Detection was performed using selected reaction monitoring (SRM); Ions representing the precursor $(M+H)^+$ species was selected in quadrupole 1 (Q1) and collided with argon gas in the collision cell (Q2) to generate specific product ion, which was subsequently monitored by quadrupole 3 (Q3). Standard curve and quality control samples were prepared in male rat plasma and processed in the same way as the test samples to generate quantitative data.

Pharmacokinetic parameters were generated using non-compartmental pharmacokinetic analysis (Phoenix WinNonlin, version 6.3). Values below the lower limit of quantification (LLOQ) were assigned a value of zero if predose and treated as missing thereafter. Area under the curve (AUC) was calculated using the linear trapezoidal rule. The oral bioavailability (% F) was determined by comparison of the area under the curve (AUC) of the compound and/or a metabolite generated in plasma following oral administration to that generated following intravenous administration.

Comparative examples (Comp 1-14) as shown in Tables 2A and 2B below were prepared according to the synthetic protocols described herein using the appropriate starting materials.

TABLE 1

| Ex. No. | 1b (nM) | 1a (nM) | 2a JFH (nM) | 2a J6 (t) (nM) | 2b (t) (nM) | 2b (s) (nM) | 3a (nM) | 4a (s) (nM) | Rat % F | 1b L31V/Y93H (nM) | 1a Q30R (nM) | 1a Q30E (nM) | 1a Y93H (nM) | 1a Y93N (nM) | 3a Y93H (nM) |
|---|---|---|---|---|---|---|---|---|---|---|---|---|---|---|---|
| AE | 0.022 | 0.024 | 0.012 | 0.042 | 0.038 |  | 0.027 | 0.011 |  |  |  |  | 0.230 | 1.121 | 6.933 |
| AF | 0.037 | 0.022 | 0.012 | 0.003 | 0.014 |  | 0.016 | 0.005 |  | 0.180 |  | 0.097 | 0.268 | 0.899 | 4.586 |
| AU | 0.039 | 0.029 | 0.013 | 0.008 | 0.017 | 0.023 | 0.029 | 0.017 | 16.4 | 0.059 |  | 0.042 | 0.026 | 0.089 | 0.130 |
| AC | 0.03 | 0.025 | 0.016 | 0.003 | 0.020 |  | 0.019 | 0.005 |  | 1.332 |  | 0.312 | 0.832 | 1.634 | 14.495 |
| AB | 0.046 | 0.026 | 0.011 | 0.028 | 0.024 |  | 0.025 | 0.006 |  | 0.668 |  | 0.082 | 0.163 | 0.418 | 8.769 |
| AA | 0.017 | 0.016 | 0.011 | 0.006 | 0.014 | 0.029 | 0.014 | 0.008 | 28.1 | 0.498 |  | 0.145 | 0.322 | 0.570 | 0.544 |
| AT |  |  |  |  |  |  |  |  |  |  |  |  |  |  |  |
| AR | 0.09 | 8.983 | 2.106 | 5.137 |  | 15.804 | 8.304 | 4.191 |  |  |  |  |  |  |  |
| AS | 0.045 | 0.026 | 0.028 | 0.015 | 0.026 | 0.064 | 0.051 | 0.024 | 17.4 | 2.033 |  | 0.115 | 0.148 | 0.325 | 0.732 |
| AQ | 0.029 | 0.019 | 0.016 | 0.011 | 0.016 | 0.032 | 0.017 | 0.012 | 22.9 | 0.908 |  | 0.074 | 0.206 | 0.337 | 0.703 |
| AP | 0.038 | 1.518 | 1.101 | 4.444 |  | 4.444 | 4.444 | 1.188 |  |  |  |  |  |  |  |
| AO | 0.015 | 0.012 | 0.008 | 0.017 | 0.015 | 0.045 | 0.021 | 0.018 | 50.3 | 17.471 |  | 1.784 |  | 9.034 | 9.057 |
| AN | 0.049 | 4.444 | 0.852 | 4.444 |  | 4.444 | 4.444 | 0.935 |  |  |  |  |  |  |  |
| AM | 0.014 | 0.009 | 0.005 | 0.008 | 0.008 | 0.023 | 0.011 | 0.01 | 21.9 | 11.641 |  | 1.213 |  | 4.651 | 8.060 |
| AJ | 0.021 | 0.016 | 0.019 | 0.059 |  | 0.057 | 0.035 | 0.018 |  | 44.000 | 0.160 | 2.700 |  | 4.303 | 3.732 |
| AI | 0.018 | 0.014 | 0.017 | 0.041 |  | 0.058 | 0.028 | 0.012 |  | 21.424 | 0.208 | 2.106 |  | 4.054 | 2.838 |
| AD | 0.031 | 0.021 | 0.027 | 1.017 |  | 0.351 | 0.074 | 0.018 |  |  |  |  |  |  |  |
| AH | 0.021 | 0.026 | 0.031 | 0.172 |  | 0.104 | 0.154 | 0.017 |  |  |  |  |  |  |  |
| AG | 0.026 | 0.023 | 0.025 | 0.121 |  | 0.092 | 0.137 | 0.014 | 27.8 |  |  |  |  |  |  |
| AL | 0.03 | 0.02 | 0.026 | 0.776 |  | 0.713 | 0.086 | 0.028 |  |  |  |  |  |  |  |
| BC | 2.474 | 10.138 | 8.039 |  |  | 23.058 | 23.3 | 6.235 |  |  |  |  |  |  |  |
| BB | 0.205 | 3.855 | 2.958 |  |  | 10.555 | 10.35 | 2.537 |  |  |  |  | 20.223 | 29.566 |  |
| BA | 0.061 | 0.169 | 0.086 |  |  | 0.202 | 0.231 | 0.108 |  |  |  |  | 0.359 | 0.496 | 40.645 |
| AZ | 0.031 | 0.021 | 0.01 |  |  | 0.024 | 0.025 | 0.013 |  |  |  |  | 0.025 | 0.059 | 4.516 |
| BD | 0.096 | 0.06 | 0.017 |  |  | 0.026 | 0.072 | 0.029 |  |  |  |  | 0.088 | 0.104 | 0.814 |
| BE | 0.019 | 0.017 | 0.011 |  |  | 0.029 | 0.022 | 0.011 |  |  |  |  | 0.755 | 1.423 | 2.253 |
| BF | 0.049 | 0.048 | 0.021 | 0.035 |  | 0.042 | 0.065 | 0.025 |  |  |  |  | 0.035 | 0.125 | 0.365 |
| BG | 0.018 | 0.02 | 0.017 | 0.045 |  | 0.039 | 0.028 | 0.017 |  |  |  |  | 0.364 | 0.883 | 5.583 |
| AX | 0.022 | 0.017 | 0.012 | 0.046 |  | 0.027 | 0.015 | 0.01 |  |  |  |  | 0.480 | 0.885 | 4.966 |
| BH | 0.118 | 0.053 | 0.013 | 0.055 |  | 0.027 | 0.056 | 0.024 | 2.7 |  |  |  | 0.040 | 0.082 | 0.612 |
| BI | 0.024 | 0.012 | 0.011 | 0.022 |  | 0.033 | 0.017 | 0.011 |  |  |  |  | 0.184 | 0.466 | 3.451 |
| AY | 0.028 | 0.027 | 0.018 | 0.013 | 0.030 |  | 0.023 | 0.011 |  |  |  |  | 0.531 | 1.180 | 8.484 |
| AV | 0.036 | 0.036 | 0.011 | 0.008 | 0.015 |  | 0.029 | 0.013 |  |  |  |  | 0.140 | 1.053 | 2.388 |

TABLE 1-continued
| Ex. No. | 1b (nM) | 1a (nM) | 2a JFH (nM) | 2a J6 (t) (nM) | 2b (t) (nM) | 2b (s) (nM) | 3a (nM) | 4a (s) (nM) | Rat % F | 1b L31V/Y93H (nM) | 1a Q30R (nM) | 1a Q30E (nM) | 1a Y93H (nM) | 1a Y93N (nM) | 3a Y93H (nM) |
|---|---|---|---|---|---|---|---|---|---|---|---|---|---|---|---|
| BJ | 0.022 | 0.027 | 0.009 | 0.066 | 0.029 | | 0.025 | 0.011 | | | | | 0.506 | 1.490 | 1.269 |
| AW | 0.07 | 0.029 | 0.011 | 0.021 | 0.029 | | 0.015 | 0.008 | | | | | 0.704 | 1.473 | 1.506 |
| BK | 0.496 | 0.171 | 0.02 | 0.033 | 0.048 | | 0.08 | 0.021 | 3.2 | | | | 0.100 | 0.251 | 0.263 |
| BL | 0.024 | 0.018 | 0.009 | 0.022 | 0.021 | | 0.014 | 0.006 | | | | | 0.228 | 0.531 | 1.047 |
| BM | 0.053 | 0.034 | 0.023 | | | | 0.143 | 0.039 | | | | | | | |
TABLE 2A
| Structure | Example No. | 1b (nM) | 1a (nM) | 2a JFH (nM) | 2a J6 (t) (nM) | 2b (t) (nM) | 2b (s) (nM) | 3a (nM) |
|---|---|---|---|---|---|---|---|---|
| 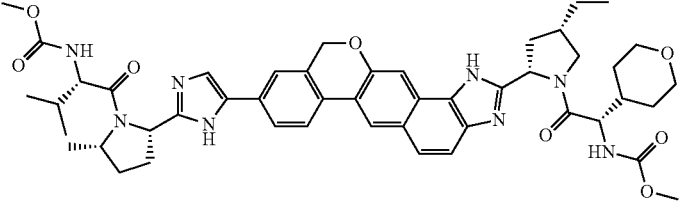 | Comp 1 | 0.027 | 0.018 | 0.008 | 0.012 | | 0.112 | 0.042 |
| 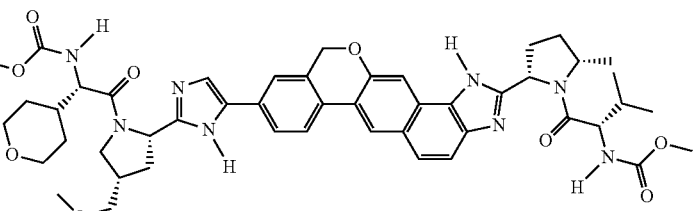 | Comp 2 | 0.064 | 0.055 | 0.025 | 0.083 | | 0.193 | 0.126 |
| 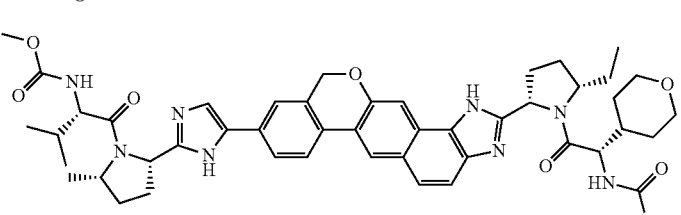 | Comp 3 | 0.026 | 0.021 | 0.019 | 0.061 | 0.038 | 0.095 | 0.065 |
| 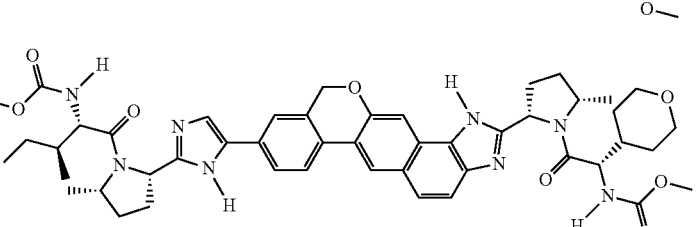 | Comp 4 | 0.028 | 0.023 | 0.018 | 0.026 | 0.044 | 0.074 | 0.043 |
| 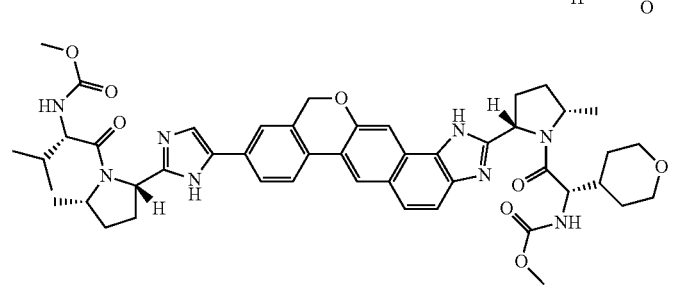 | Comp 5 | 0.029 | 0.022 | 0.013 | 0.012 | 0.024 | 0.054 | 0.041 |

TABLE 2A-continued

| Structure | Example No. | 1b (nM) | 1a (nM) | 2a JFH (nM) | 2a J6 (t) (nM) | 2b (t) (nM) | 2b (s) (nM) | 3a (nM) |
|---|---|---|---|---|---|---|---|---|
| 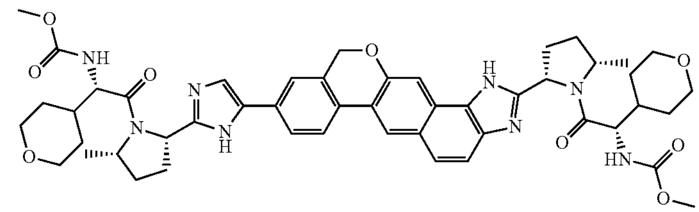 | Comp 6 | 0.051 | 0.024 | 0.012 | 0.012 | 0.092 | 0.038 | 0.075 |
| 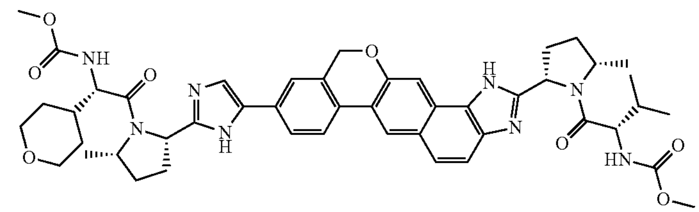 | Comp 7 | 0.028 | 0.018 | 0.015 | 0.035 | 0.037 | 0.088 | 0.035 |
| 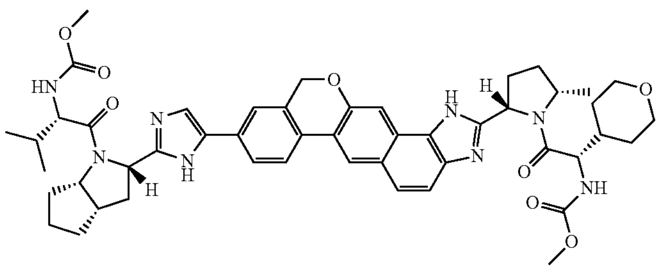 [SMILES: COC(=O)N[C@H](C(=O)N1[C@H](c2ncc(-c3ccc4c(c3)COc3cc5c(ccc6nc([C@@H]7CC[C@H](C)N7C(=O)[C@@H](NC(=O)OC)C7CCOCC7)[nH]c65)cc3-4)[nH]2)C[C@@H]2CCC[C@@H]21)C(C)C] | Comp 8 | 0.04 | 0.028 | 0.012 | | | 0.113 | 0.071 |
| 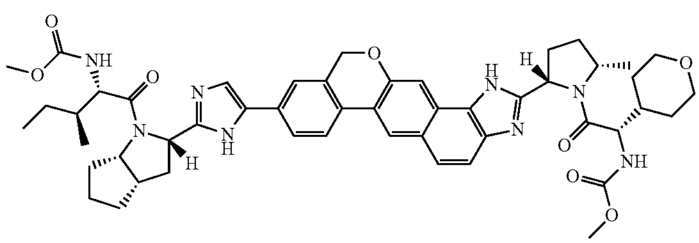 [SMILES: CC[C@H](C)[C@H](NC(=O)OC)C(=O)N1[C@H](c2ncc(-c3ccc4c(c3)COc3cc5c(ccc6nc([C@@H]7CC[C@H](C)N7C(=O)[C@@H](NC(=O)OC)C7CCOCC7)[nH]c65)cc3-4)[nH]2)C[C@@H]2CCC[C@@H]21] | Comp 9 | 0.034 | 0.028 | 0.019 | | 0.025 | 0.143 | 0.083 |
| 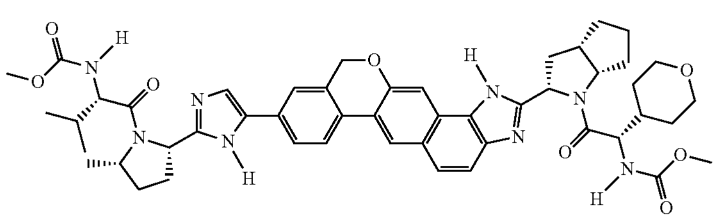 | Comp 10 | 0.024 | 0.015 | 0.021 | 0.024 | 0.033 | 0.062 | 0.052 |
| 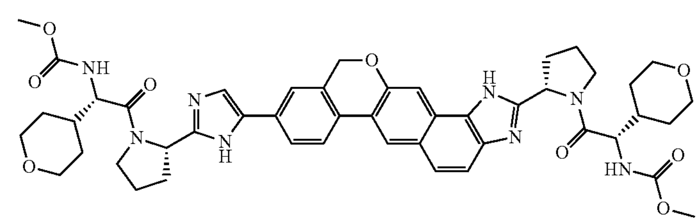 | Comp 11 | 0.416 | 0.203 | 0.041 | 0.2 | | 0.203 | 0.447 |

TABLE 2A-continued

| Structure | Example No. | 1b (nM) | 1a (nM) | 2a JFH (nM) | 2a J6 (t) (nM) | 2b (t) (nM) | 2b (s) (nM) | 3a (nM) |
|---|---|---|---|---|---|---|---|---|
| 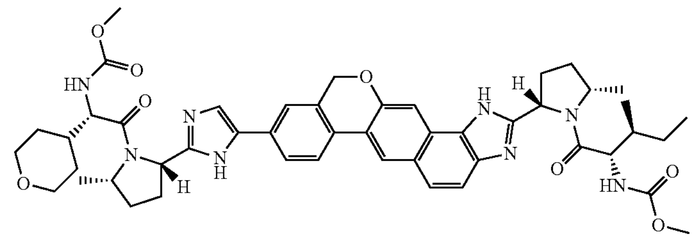 [SMILES: CC[C@H](C)[C@H](NC(=O)OC)C(=O)N1[C@@H](C)CC[C@H]1c1nc2ccc3cc4c(cc3c2[nH]1)OCc1cc(-c2cnc([C@@H]3CC[C@H](C)N3C(=O)[C@@H](NC(=O)OC)C3CCOCC3)[nH]2)ccc1-4] | Comp 12 | 0.022 | 0.013 | 0.009 | 0.032 | | 0.07 | 0.026 |
| 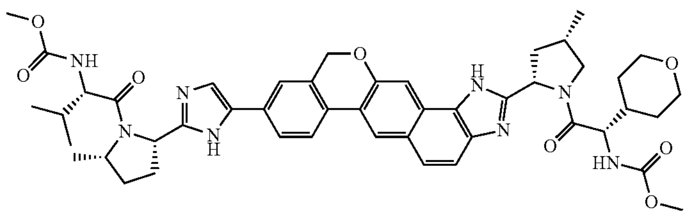 | Comp 13 | 0.048 | 0.025 | 0.033 | 0.022 | | 0.048 | 0.077 |
| 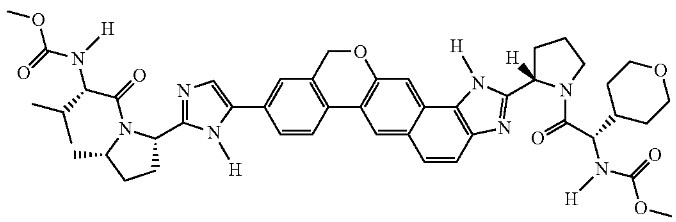 | Comp 14 | 0.025 | 0.025 | 0.01 | 0.053 | 0.036 | | |

TABLE 2B

| Example No. | Structure | 4a (s) (nM) | Rat % F | 1b L31V/ Y93H (nM) | 1a Q30R (nM) | 1a Q30E (nM) | 1a Y93H (nM) | 1a Y93N (nM) | 3a Y93H (nM) |
|---|---|---|---|---|---|---|---|---|---|
| Comp 1 | 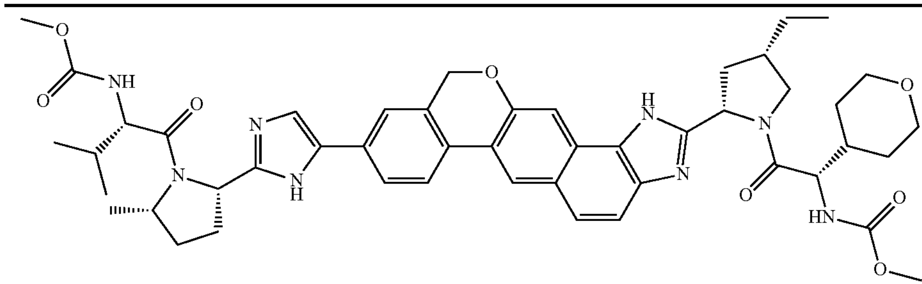 | 0.016 | 9.9 | 0.971 | 0.061 | 0.319 | | 2.047 | 8.073 |
| Comp 2 | 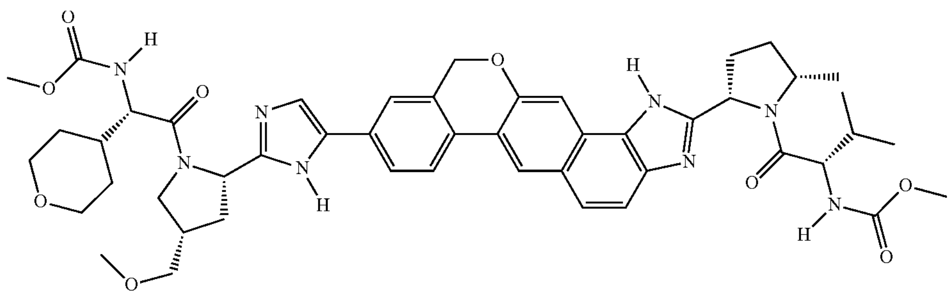 | 0.022 | | | | | | | |
| Comp 3 | 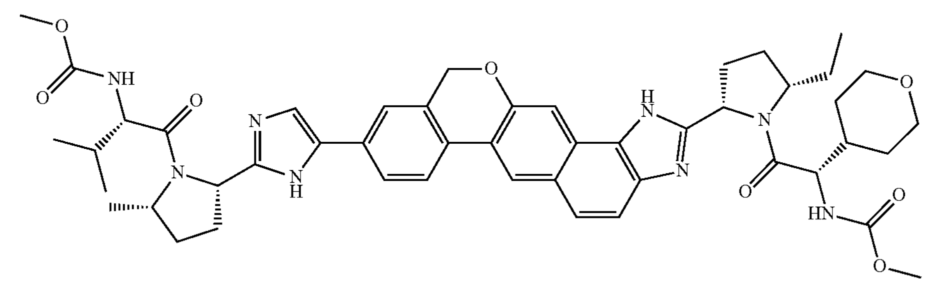 | 0.014 | 46.6 | | 0.052 | 0.526 | 2.537 | | 14.074 |

TABLE 2B-continued

| Example No. | Structure | 4a (s) (nM) | Rat % F | 1b L31V/ Y93H (nM) | 1a Q30R (nM) | 1a Q30E (nM) | 1a Y93H (nM) | 1a Y93N (nM) | 3a Y93H (nM) |
|---|---|---|---|---|---|---|---|---|---|
| Comp 4 | 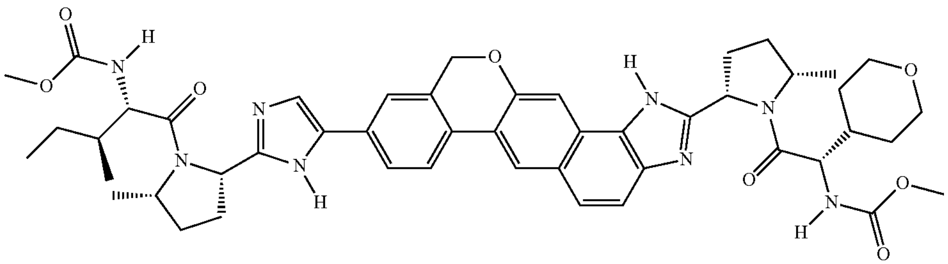 | 0.021 | 22.1 | | 0.032 | 0.432 | 0.978 | 1.062 | 0.695 |
| Comp 5 | 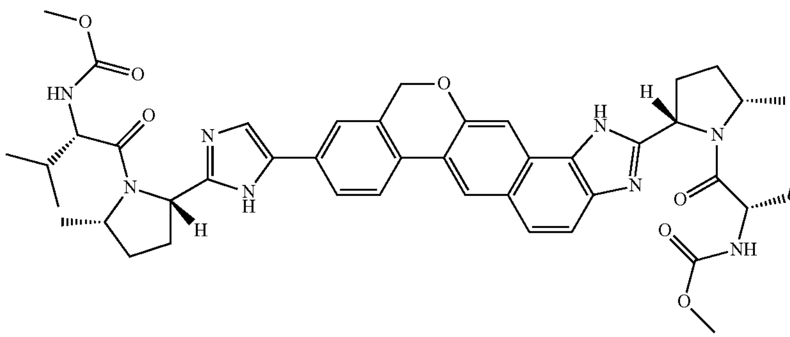 | 0.021 | 22 | | 0.031 | 0.297 | 0.466 | | 0.549 |
| Comp 6 | 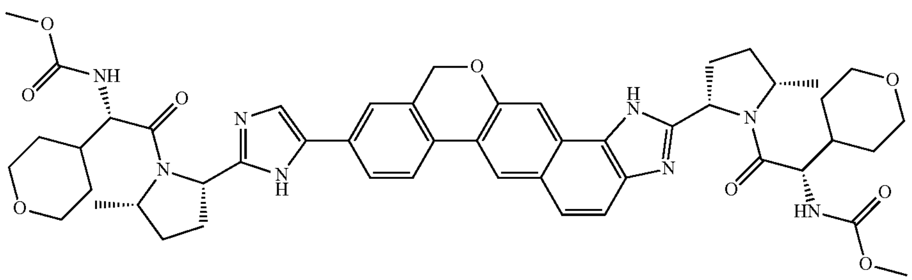 | 0.014 | | | 0.042 | 0.101 | 0.442 | | 0.252 |

TABLE 2B-continued

| Example No. | 4a (s) (nM) | Rat % F | 1b L31V/ Y93H (nM) | 1a Q30R (nM) | 1a Q30E (nM) | 1a Y93H (nM) | 1a Y93N (nM) | 3a Y93H (nM) |
|---|---|---|---|---|---|---|---|---|
| Comp 7 | 0.019 | 10.2 | | | | | | |
| Comp 8 | | | | | 0.979 | 1.901 | 4.576 | |
| Comp 9 | 40.9 | 0.571 | | 0.260 | | 3.495 | 10.580 | 40.9 |

TABLE 2B-continued

| Example No. | Structure | 4a (s) (nM) | Rat % F | 1b L31V/ Y93H (nM) | 1a Q30R (nM) | 1a Q30E (nM) | 1a Y93H (nM) | 1a Y93N (nM) | 3a Y93H (nM) |
|---|---|---|---|---|---|---|---|---|---|
| Comp 10 | 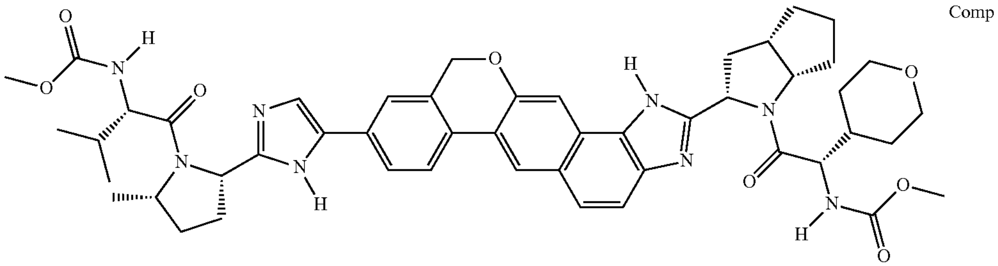 | 21.8 | | 0.024 | 0.123 | 0.716 | | 3.739 | 21.8 |
| Comp 11 | 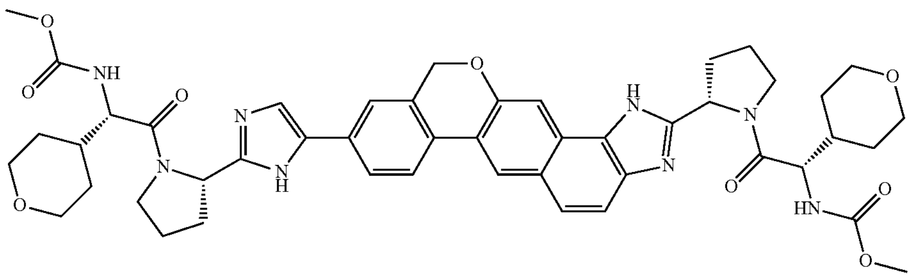 | | | | | | | | |
| Comp 12 | 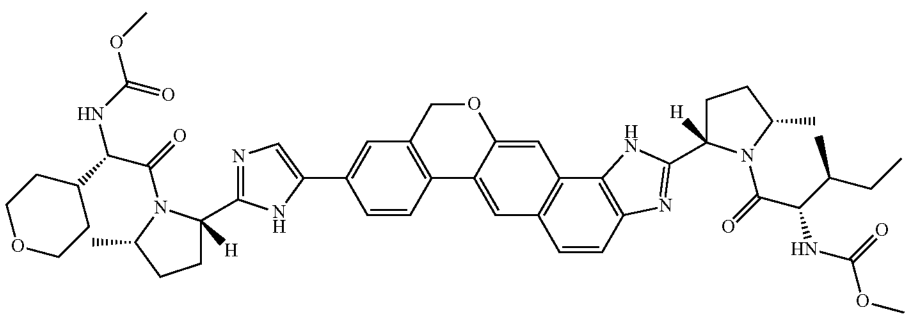 [SMILES: CC[C@H](C)[C@H](NC(=O)OC)C(=O)N1[C@@H](C)CC[C@H]1c1nc2ccc3cc4c(cc3c2[nH]1)OCc1cc(-c2cnc([C@@H]3CC[C@H](C)N3C(=O)[C@@H](NC(=O)OC)C3CCOCC3)[nH]2)ccc1-4] | 17.7 | 5.643 | 0.097 | 1.283 | | 1.244 | 1.379 | 17.7 |

TABLE 2B-continued

| Example No. | Structure | 4a (s) (nM) | Rat % F | 1b L31V/ Y93H (nM) | 1a Q30R (nM) | 1a Q30E (nM) | 1a Y93H (nM) | 1a Y93N (nM) | 3a Y93H (nM) |
|---|---|---|---|---|---|---|---|---|---|
| Comp 13 | 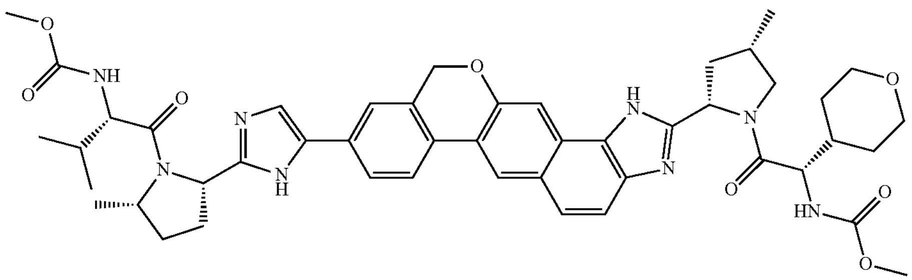 | 4.4 | | | | 0.371 | 1.074 | 2.128 | 4.4 |
| Comp 14 | 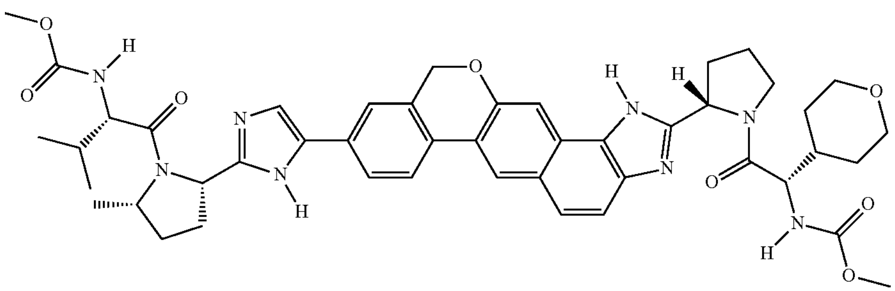 | | 6.882 | 0.130 | 1.195 | | 3.664 | 1.746 | |

The invention claimed is:
1. A compound of formula:

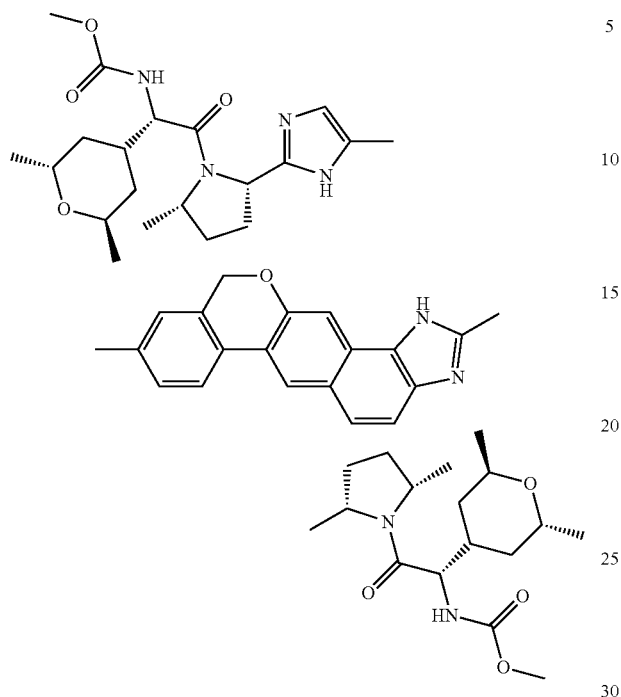

or a pharmaceutically acceptable salt thereof.

2. A pharmaceutical composition comprising the compound of claim 1 or a pharmaceutically acceptable salt thereof; and at least one pharmaceutically acceptable carrier.

3. The pharmaceutical composition of claim 2 in the form of a sterile injectable preparation.

4. The pharmaceutical composition of claim 2 in the form of a sterile injectable aqueous or oleaginous suspension.

5. The pharmaceutical composition of claim 4 in the form of sterile injectable aqueous suspension.

6. A compound of formula:

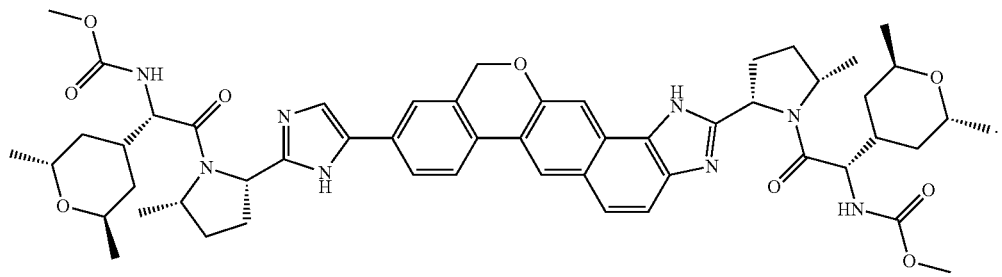

* * * * *